(12) United States Patent
Minskoff et al.

(10) Patent No.: US 9,743,691 B2
(45) Date of Patent: Aug. 29, 2017

(54) VAPORIZER CONFIGURATION, CONTROL, AND REPORTING

(71) Applicant: R.J. Reynolds Tobacco Company, Winston-Salem, NC (US)

(72) Inventors: Noah Mark Minskoff, Palo Alto, CA (US); Nathan Andrew Terry, Lowman, ID (US)

(73) Assignee: RAI Strategic Holdings, Inc., Winston-Salem, NC (US)

(*) Notice: Subject to any disclaimer, the term of this patent is extended or adjusted under 35 U.S.C. 154(b) by 0 days.

(21) Appl. No.: 14/276,894

(22) Filed: May 13, 2014

(65) Prior Publication Data

US 2014/0246035 A1    Sep. 4, 2014

Related U.S. Application Data

(63) Continuation-in-part of application No. 12/780,876, filed on May 15, 2010, now Pat. No. 9,095,175.
(Continued)

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/0025* (2014.02);
(Continued)

(58) Field of Classification Search
CPC .... A24F 47/002; A24F 47/004; A24F 47/006; A24F 47/008; A61M 15/06;
(Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

*Primary Examiner* — Valerie L Woodward
(74) *Attorney, Agent, or Firm* — Brinks Gilson & Lione

(57) ABSTRACT

A personal vapor inhaling unit including a microprocessor, memory, and a wireless communication interface is disclosed. An application may control aspects of the personal vapor via the wireless interface. An electronic flameless vapor inhaler unit that may simulate a cigarette has a cavity that receives a cartridge in the distal end of the inhaler unit. The cartridge brings a substance to be vaporized in contact with a wick. When the unit is activated, and the user provides suction, the substance to be vaporized is drawn out of the cartridge, through the wick, and is atomized by the wick into a cavity containing a heating element. The heating element vaporizes the atomized substance. The vapors then continue to be pulled by the user through a mouthpiece and mouthpiece cover where they may be inhaled.

12 Claims, 31 Drawing Sheets

Related U.S. Application Data

(60) Provisional application No. 61/987,005, filed on May 1, 2014.

(51) Int. Cl.
   *A61M 11/04* (2006.01)
   *A61M 15/00* (2006.01)

(52) U.S. Cl.
   CPC ........ *A61M 15/0035* (2014.02); *A61M 15/06* (2013.01); *A61M 2205/0205* (2013.01); *A61M 2205/0233* (2013.01); *A61M 2205/13* (2013.01); *A61M 2205/3592* (2013.01); *A61M 2205/52* (2013.01); *A61M 2205/59* (2013.01); *A61M 2205/8206* (2013.01); *A61M 2230/005* (2013.01); *A61M 2230/65* (2013.01)

(58) Field of Classification Search
   CPC ...... A61M 15/0065; A61M 2205/8237; A61M 2205/8256; A61M 2205/50; A61M 2205/52; A61M 2205/3553; A61M 16/10; A61M 2016/10; A61M 2016/0068; A61M 2016/008; A61M 11/00; A61M 15/00
   USPC ............. 128/200.11–200.13, 200.14–200.23, 128/202.21, 203.12, 203.16, 203.17, 128/203.23, 203.26, 203.27, 204.13, 128/204.14, 205.23; 131/273
   See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 3,751,969 A | 8/1973 | Schrock |
| 4,219,032 A | 8/1980 | Tabatznik et al. |
| 4,259,970 A | 4/1981 | Green, Jr. |
| 4,284,089 A | 8/1981 | Ray |
| 4,303,083 A | 12/1981 | Burruss, Jr. |
| 4,429,703 A | 2/1984 | Haber |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,776,353 A | 10/1988 | Lilja et al. |
| 4,793,365 A | 12/1988 | Sensabaugh, Jr. et al. |
| 4,819,665 A | 4/1989 | Roberts et al. |
| 4,848,374 A | 7/1989 | Chard et al. |
| 4,848,376 A | 7/1989 | Lilja et al. |
| 4,907,606 A | 3/1990 | Lilja et al. |
| 4,913,168 A | 4/1990 | Potter et al. |
| 4,917,119 A | 4/1990 | Potter et al. |
| 4,922,901 A | 5/1990 | Brooks et al. |
| 4,938,236 A | 7/1990 | Banerjee et al. |
| 4,941,483 A | 7/1990 | Ridings et al. |
| 4,945,931 A | 8/1990 | Gori |
| 4,947,874 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,095,921 A | 3/1992 | Losee et al. |
| 5,097,850 A | 3/1992 | Braunshteyn et al. |
| 5,144,962 A | 9/1992 | Counts et al. |
| 5,159,940 A | 11/1992 | Hayward et al. |
| 5,179,966 A | 1/1993 | Losee et al. |
| 5,211,684 A | 5/1993 | Shannon et al. |
| 5,224,498 A | 7/1993 | Deevi et al. |
| 5,228,460 A | 7/1993 | Sprinkel, Jr. et al. |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,322,075 A | 6/1994 | Deevi et al. |
| 5,345,951 A | 9/1994 | Serrano et al. |
| 5,353,813 A | 10/1994 | Deevi et al. |
| 5,366,122 A | 11/1994 | Guentert et al. |
| 5,369,723 A | 11/1994 | Counts et al. |
| 5,372,148 A | 12/1994 | McCafferty et al. |
| 5,388,574 A | 2/1995 | Ingebrethsen |
| 5,388,594 A | 2/1995 | Counts et al. |
| 5,408,574 A | 4/1995 | Deevi et al. |
| 5,468,936 A | 11/1995 | Deevi et al. |
| 5,479,948 A | 1/1996 | Counts et al. |
| 5,498,850 A | 3/1996 | Das |
| 5,498,855 A | 3/1996 | Deevi et al. |
| 5,499,636 A | 3/1996 | Baggett, Jr. et al. |
| 5,505,214 A | 4/1996 | Collins et al. |
| 5,515,842 A | 5/1996 | Ramseyer et al. |
| 5,530,225 A | 6/1996 | Hajaligol |
| 5,551,451 A | 9/1996 | Riggs et al. |
| 5,564,442 A | 10/1996 | MacDonald et al. |
| 5,573,692 A | 11/1996 | Das et al. |
| 5,591,368 A | 1/1997 | Fleischhauer et al. |
| 5,595,706 A | 1/1997 | Sikk et al. |
| 5,611,360 A | 3/1997 | Tang |
| 5,613,504 A | 3/1997 | Collins et al. |
| 5,613,505 A | 3/1997 | Campbell et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,687,746 A | 11/1997 | Rose et al. |
| 5,692,525 A | 12/1997 | Counts et al. |
| 5,692,526 A | 12/1997 | Adams et al. |
| 5,708,258 A | 1/1998 | Counts et al. |
| 5,709,202 A | 1/1998 | Lloyd et al. |
| 5,726,421 A | 3/1998 | Fleischhauer et al. |
| 5,730,158 A | 3/1998 | Collins et al. |
| 5,743,251 A | 4/1998 | Howell et al. |
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,893,371 A | 4/1999 | Rose et al. |
| 5,894,841 A | 4/1999 | Voges |
| 5,915,387 A | 6/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,866 A | 10/2000 | Nichols et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,349,728 B1 | 2/2002 | Pham |
| 6,418,938 B1 | 7/2002 | Fleischhauer et al. |
| 6,443,146 B1 * | 9/2002 | Voges ..................... 128/200.14 |
| 6,446,426 B1 | 9/2002 | Sweeney et al. |
| 6,557,552 B1 | 5/2003 | Cox et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,637,430 B1 * | 10/2003 | Voges et al. ............. 128/200.14 |
| 6,681,769 B2 | 1/2004 | Sprinkel, Jr. et al. |
| 6,688,313 B2 | 2/2004 | Wrenn et al. |
| 6,715,494 B1 | 4/2004 | McCoy |

(56) References Cited

U.S. PATENT DOCUMENTS

| | | |
|---|---|---|
| 6,766,220 B2 | 7/2004 | McRae et al. |
| 6,772,756 B2 | 8/2004 | Shayan |
| 6,772,757 B2 | 8/2004 | Sprinkel, Jr. et al. |
| 6,803,545 B2 | 10/2004 | Blake et al. |
| 6,803,550 B2 | 10/2004 | Sharpe et al. |
| 6,804,458 B2 | 10/2004 | Sherwood et al. |
| 6,810,883 B2 | 11/2004 | Felter et al. |
| 6,854,461 B2 | 2/2005 | Nichols et al. |
| 6,854,470 B1 | 2/2005 | Pa |
| 6,923,179 B2 | 8/2005 | Gupta et al. |
| 6,994,096 B2 | 2/2006 | Rostami et al. |
| 7,040,314 B2 | 5/2006 | Nguyen et al. |
| 7,041,941 B2 * | 5/2006 | Faries et al. ............... 219/413 |
| 7,117,867 B2 | 10/2006 | Cox et al. |
| 7,147,170 B2 | 12/2006 | Nguyen et al. |
| 7,163,015 B2 | 1/2007 | Moffitt |
| 7,167,776 B2 | 1/2007 | Maharajh et al. |
| 7,173,222 B2 | 2/2007 | Cox et al. |
| 7,185,659 B2 | 3/2007 | Sharpe et al. |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,400,940 B2 | 7/2008 | McRae et al. |
| 7,500,479 B2 | 3/2009 | Nichols et al. |
| D590,988 S | 4/2009 | Hon |
| D590,989 S | 4/2009 | Hon |
| D590,990 S | 4/2009 | Hon |
| D590,991 S | 4/2009 | Hon |
| 7,607,431 B1 * | 10/2009 | Cruitt et al. ............. 128/200.14 |
| 7,645,442 B2 | 1/2010 | Hale et al. |
| D614,346 S | 4/2010 | Lik |
| 7,690,385 B2 | 4/2010 | Moffitt |
| 7,692,123 B2 | 4/2010 | Baba et al. |
| 7,726,320 B2 | 6/2010 | Robinson et al. |
| 7,810,505 B2 | 10/2010 | Yang |
| 7,832,410 B2 | 11/2010 | Hon |
| 7,845,359 B2 | 12/2010 | Montaser |
| 7,983,113 B2 | 7/2011 | Krueger et al. |
| D644,375 S | 8/2011 | Zhou |
| 7,997,280 B2 | 8/2011 | Rosenthal |
| 8,003,080 B2 | 8/2011 | Rabinowitz et al. |
| 8,042,550 B2 | 10/2011 | Urtsev et al. |
| D649,708 S | 11/2011 | O'Neil |
| 8,079,371 B2 | 12/2011 | Robinson et al. |
| 8,091,558 B2 | 1/2012 | Martzel |
| D653,803 S | 2/2012 | Timmermans |
| D655,036 S | 2/2012 | Zhou |
| 8,127,772 B2 | 3/2012 | Montaser |
| D657,047 S | 4/2012 | Minskoff et al. |
| 8,156,944 B2 | 4/2012 | Hon |
| D662,257 S | 6/2012 | Alelov |
| 8,191,555 B2 | 6/2012 | Herbrich |
| 8,205,622 B2 | 6/2012 | Pan |
| D666,355 S | 8/2012 | Alelov |
| 8,291,918 B2 | 10/2012 | Magnon |
| 8,314,591 B2 | 11/2012 | Terry et al. |
| 8,322,350 B2 | 12/2012 | Lipowicz |
| 8,342,184 B2 | 1/2013 | Inagaki et al. |
| D675,777 S | 2/2013 | Wu |
| D677,000 S | 2/2013 | Liu |
| D677,001 S | 2/2013 | Liu |
| 8,365,742 B2 | 2/2013 | Hon |
| 8,371,310 B2 | 2/2013 | Brenneise |
| 8,375,957 B2 | 2/2013 | Hon |
| 8,393,331 B2 | 3/2013 | Hon |
| 8,402,976 B2 | 3/2013 | Fernando et al. |
| D681,268 S | 4/2013 | Wu |
| D681,269 S | 4/2013 | Wu |
| 8,430,106 B2 | 4/2013 | Potter et al. |
| D682,090 S | 5/2013 | Scatterday |
| D682,465 S | 5/2013 | Yeom |
| 8,434,478 B2 | 5/2013 | Yamada et al. |
| D683,897 S | 6/2013 | Liu |
| D683,898 S | 6/2013 | Liu |
| D683,899 S | 6/2013 | Liu |
| D684,311 S | 6/2013 | Liu |
| 8,459,271 B2 | 6/2013 | Inagaki |
| D685,522 S | 7/2013 | Potter et al. |
| 8,479,747 B2 | 7/2013 | O'Connell |
| 8,490,628 B2 | 7/2013 | Hon |
| 8,495,998 B2 | 7/2013 | Schennum |
| D687,999 S | 8/2013 | Liu |
| D688,415 S | 8/2013 | Kim |
| D688,416 S | 8/2013 | Liu |
| D688,418 S | 8/2013 | Liu |
| 8,499,766 B1 | 8/2013 | Newton |
| 8,505,548 B2 | 8/2013 | Hearn |
| 8,511,318 B2 | 8/2013 | Hon |
| 8,517,032 B2 | 8/2013 | Urtsev et al. |
| 8,528,569 B1 | 9/2013 | Newton |
| 8,539,959 B1 | 9/2013 | Scatterday |
| D691,324 S | 10/2013 | Saliman |
| D692,612 S | 10/2013 | Lowenthal et al. |
| D692,614 S | 10/2013 | Robinson |
| D692,615 S | 10/2013 | Verleur |
| 8,550,068 B2 | 10/2013 | Terry et al. |
| 8,550,069 B2 | 10/2013 | Alelov |
| 8,558,147 B2 | 10/2013 | Greim et al. |
| D693,054 S | 11/2013 | Verleur |
| D693,055 S | 11/2013 | Manca |
| 8,578,942 B2 | 11/2013 | Schennum |
| D696,051 S | 12/2013 | Scatterday |
| D696,455 S | 12/2013 | Abroff |
| D696,815 S | 12/2013 | Abroff |
| 8,596,460 B2 | 12/2013 | Scatterday |
| 8,602,037 B2 | 12/2013 | Inagaki |
| D697,482 S | 1/2014 | Cheng |
| 8,634,709 B2 | 1/2014 | Maharajh et al. |
| D699,391 S | 2/2014 | Abroff et al. |
| D700,397 S | 2/2014 | Manca et al. |
| D700,738 S | 3/2014 | Rennick et al. |
| D700,739 S | 3/2014 | Manca et al. |
| D700,994 S | 3/2014 | Alarcon et al. |
| 8,678,012 B2 | 3/2014 | Li et al. |
| D702,876 S | 4/2014 | Liu |
| 8,689,786 B2 | 4/2014 | Schennum et al. |
| 8,689,804 B2 | 4/2014 | Fernando et al. |
| 8,689,805 B2 | 4/2014 | Hon |
| 8,695,794 B2 | 4/2014 | Scatterday |
| 8,707,965 B2 | 4/2014 | Newton |
| D704,549 S | 5/2014 | Liu |
| D704,629 S | 5/2014 | Liu |
| D704,630 S | 5/2014 | Liu |
| D705,814 S | 5/2014 | Liberti et al. |
| 8,714,161 B2 | 5/2014 | Liu |
| 8,733,345 B2 | 5/2014 | Siller |
| 8,733,346 B2 | 5/2014 | Rinker |
| D706,976 S | 6/2014 | Wu |
| D707,389 S | 6/2014 | Liu |
| 8,746,240 B2 | 6/2014 | Terry et al. |
| 8,752,557 B2 | 6/2014 | Lipowicz |
| 8,757,169 B2 | 6/2014 | Gysland |
| 8,833,364 B2 * | 9/2014 | Buchberger ............. 128/202.21 |
| 8,893,726 B2 | 11/2014 | Hon |
| 2002/0136886 A1 | 9/2002 | He et al. |
| 2004/0020500 A1 | 2/2004 | Wrenn et al. |
| 2004/0055613 A1 | 3/2004 | Horian |
| 2004/0084044 A1 | 5/2004 | Childers et al. |
| 2004/0089314 A1 | 5/2004 | Felter et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2005/0133027 A1 * | 6/2005 | Elaz et al. ............... 128/200.24 |
| 2005/0172976 A1 | 8/2005 | Newman et al. |
| 2006/0016453 A1 | 1/2006 | Kim |
| 2006/0021614 A1 | 2/2006 | Wermeling et al. |
| 2006/0070633 A1 | 4/2006 | Rostami et al. |
| 2006/0185687 A1 | 8/2006 | Hearn et al. |
| 2006/0196518 A1 | 9/2006 | Hon |
| 2006/0283468 A1 | 12/2006 | Lipowiez |
| 2007/0074734 A1 | 4/2007 | Braunshteyn et al. |

(56) References Cited

U.S. PATENT DOCUMENTS

| | | |
|---|---|---|
| 2007/0102013 A1 | 5/2007 | Adams et al. |
| 2007/0186923 A1* | 8/2007 | Poutiatine et al. ...... 128/200.14 |
| 2007/0240711 A1 | 10/2007 | Hamano |
| 2007/0267031 A1 | 11/2007 | Hon |
| 2007/0283972 A1 | 12/2007 | Monsees et al. |
| 2008/0056691 A1 | 3/2008 | Wingo et al. |
| 2008/0099011 A1 | 5/2008 | Gonda et al. |
| 2008/0149118 A1 | 6/2008 | Oglesby et al. |
| 2008/0257367 A1 | 10/2008 | Paterno et al. |
| 2008/0302374 A1 | 12/2008 | Wengert et al. |
| 2009/0065010 A1 | 3/2009 | Shands |
| 2009/0095311 A1* | 4/2009 | Han .............................. 131/194 |
| 2009/0114737 A1 | 5/2009 | Yu et al. |
| 2009/0126745 A1 | 5/2009 | Hon |
| 2009/0151717 A1 | 6/2009 | Bowen et al. |
| 2009/0151718 A1* | 6/2009 | Hunter et al. ........... 128/203.12 |
| 2009/0178672 A1 | 7/2009 | Mullinger et al. |
| 2009/0188490 A1 | 7/2009 | Han |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1* | 11/2009 | Thorens ................ A24F 47/008 128/202.21 |
| 2009/0283103 A1* | 11/2009 | Nielsen .................... A24F 1/30 131/273 |
| 2009/0293892 A1 | 12/2009 | Williams et al. |
| 2010/0024834 A1 | 2/2010 | Oglesby et al. |
| 2010/0031968 A1 | 2/2010 | Sheikh et al. |
| 2010/0059073 A1 | 3/2010 | Hoffmann et al. |
| 2010/0083959 A1 | 4/2010 | Siller |
| 2010/0126505 A1 | 5/2010 | Rinker |
| 2010/0163063 A1 | 7/2010 | Fernando et al. |
| 2010/0242975 A1 | 9/2010 | Hearn |
| 2010/0242976 A1 | 9/2010 | Katayama et al. |
| 2010/0300467 A1 | 12/2010 | Kuistila et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0147486 A1 | 6/2011 | Greim et al. |
| 2011/0155153 A1 | 6/2011 | Thorens et al. |
| 2011/0162663 A1 | 7/2011 | Bryman |
| 2011/0226236 A1* | 9/2011 | Buchberger ............. 128/200.23 |
| 2011/0232654 A1 | 9/2011 | Mass |
| 2011/0265806 A1 | 11/2011 | Alarcon et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0290244 A1 | 12/2011 | Schennum |
| 2011/0290248 A1 | 12/2011 | Schennum |
| 2011/0290266 A1 | 12/2011 | Köller |
| 2011/0290267 A1 | 12/2011 | Yamada et al. |
| 2011/0290269 A1 | 12/2011 | Shimizu et al. |
| 2011/0297166 A1 | 12/2011 | Takeuchi et al. |
| 2011/0304282 A1 | 12/2011 | Li et al. |
| 2011/0309157 A1 | 12/2011 | Yang et al. |
| 2012/0006342 A1 | 1/2012 | Rose et al. |
| 2012/0006343 A1 | 1/2012 | Renaud et al. |
| 2012/0111346 A1 | 5/2012 | Rinker |
| 2012/0111347 A1 | 5/2012 | Hon |
| 2012/0118301 A1 | 5/2012 | Montaser |
| 2012/0118307 A1 | 5/2012 | Tu |
| 2012/0138052 A1 | 6/2012 | Hearn et al. |
| 2012/0138054 A1 | 6/2012 | Hearn et al. |
| 2012/0145169 A1 | 6/2012 | Wu |
| 2012/0152244 A1 | 6/2012 | Yomtov |
| 2012/0152246 A1 | 6/2012 | Yomtov |
| 2012/0160251 A1 | 6/2012 | Hammel et al. |
| 2012/0167906 A1 | 7/2012 | Gysland |
| 2012/0186594 A1 | 7/2012 | Liu |
| 2012/0199146 A1 | 8/2012 | Marangos |
| 2012/0199663 A1 | 8/2012 | Qiu |
| 2012/0204889 A1 | 8/2012 | Xiu |
| 2012/0211015 A1 | 8/2012 | Hon |
| 2012/0227752 A1 | 9/2012 | Alelov |
| 2012/0234315 A1 | 9/2012 | Hon |
| 2012/0247494 A1 | 10/2012 | Oglesby et al. |
| 2012/0255567 A1 | 10/2012 | Rose |
| 2012/0260926 A1 | 10/2012 | Tu |
| 2012/0260927 A1 | 10/2012 | Liu |
| 2012/0273589 A1 | 11/2012 | Hon |
| 2012/0285475 A1 | 11/2012 | Liu |
| 2012/0298123 A1 | 11/2012 | Woodcock et al. |
| 2012/0312313 A1 | 12/2012 | Frija |
| 2012/0318882 A1 | 12/2012 | Abehasera |
| 2012/0325227 A1 | 12/2012 | Robinson et al. |
| 2012/0325228 A1 | 12/2012 | Williams |
| 2013/0008457 A1 | 1/2013 | Zheng et al. |
| 2013/0019862 A1 | 1/2013 | Yamada et al. |
| 2013/0019887 A1 | 1/2013 | Liu |
| 2013/0025609 A1 | 1/2013 | Liu |
| 2013/0037041 A1 | 2/2013 | Worm et al. |
| 2013/0037042 A1 | 2/2013 | Hearn et al. |
| 2013/0042865 A1 | 2/2013 | Monsees et al. |
| 2013/0056012 A1 | 3/2013 | Hearn et al. |
| 2013/0056013 A1 | 3/2013 | Terry et al. |
| 2013/0061861 A1 | 3/2013 | Hearn |
| 2013/0068239 A1 | 3/2013 | Youn |
| 2013/0074854 A1 | 3/2013 | Lipowicz |
| 2013/0074857 A1 | 3/2013 | Buchberger |
| 2013/0081623 A1 | 4/2013 | Buchberger |
| 2013/0081642 A1 | 4/2013 | Safari |
| 2013/0087160 A1 | 4/2013 | Gherghe |
| 2013/0104916 A1 | 5/2013 | Bellinger et al. |
| 2013/0125906 A1 | 5/2013 | Hon |
| 2013/0139833 A1 | 6/2013 | Hon |
| 2013/0140200 A1 | 6/2013 | Scatterday |
| 2013/0146489 A1 | 6/2013 | Scatterday |
| 2013/0152954 A1 | 6/2013 | Youn |
| 2013/0160764 A1 | 6/2013 | Liu |
| 2013/0160765 A1 | 6/2013 | Liu |
| 2013/0167853 A1 | 7/2013 | Liu |
| 2013/0167854 A1 | 7/2013 | Shin |
| 2013/0169230 A1 | 7/2013 | Li et al. |
| 2013/0180533 A1 | 7/2013 | Kim et al. |
| 2013/0192615 A1 | 8/2013 | Tucker et al. |
| 2013/0192616 A1 | 8/2013 | Tucker et al. |
| 2013/0192617 A1 | 8/2013 | Thompson |
| 2013/0192618 A1 | 8/2013 | Li |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0199528 A1 | 8/2013 | Goodman et al. |
| 2013/0206154 A1 | 8/2013 | Fernando et al. |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |
| 2013/0220316 A1 | 8/2013 | Oglesby et al. |
| 2013/0228190 A1 | 9/2013 | Weiss et al. |
| 2013/0243410 A1 | 9/2013 | Nichols et al. |
| 2013/0247924 A1 | 9/2013 | Scatterday et al. |
| 2013/0248385 A1 | 9/2013 | Scatterday et al. |
| 2013/0255675 A1 | 10/2013 | Liu |
| 2013/0263869 A1 | 10/2013 | Zhu |
| 2013/0276798 A1 | 10/2013 | Hon |
| 2013/0276799 A1 | 10/2013 | Davidson et al. |
| 2013/0276802 A1 | 10/2013 | Scatterday |
| 2013/0276804 A1 | 10/2013 | Hon |
| 2013/0284190 A1 | 10/2013 | Scatterday |
| 2013/0284191 A1 | 10/2013 | Scatterday |
| 2013/0284192 A1 | 10/2013 | Peleg et al. |
| 2013/0284194 A1 | 10/2013 | Newton |
| 2013/0298905 A1 | 11/2013 | Levin et al. |
| 2013/0298922 A1 | 11/2013 | Xiang |
| 2013/0300350 A1 | 11/2013 | Xiang |
| 2013/0306064 A1 | 11/2013 | Thorens et al. |

(56) References Cited

U.S. PATENT DOCUMENTS

| | | |
|---|---|---|
| 2013/0306065 A1 | 11/2013 | Thorens et al. |
| 2013/0306084 A1 | 11/2013 | Flick |
| 2013/0306692 A1 | 11/2013 | Mangum et al. |
| 2013/0312739 A1 | 11/2013 | Rome et al. |
| 2013/0312742 A1 | 11/2013 | Monsees |
| 2013/0313139 A1 | 11/2013 | Scatterday |
| 2013/0319404 A1 | 12/2013 | Feriani et al. |
| 2013/0319407 A1 | 12/2013 | Liu |
| 2013/0319431 A1 | 12/2013 | Cyphert et al. |
| 2013/0319435 A1 | 12/2013 | Flick |
| 2013/0319436 A1 | 12/2013 | Liu |
| 2013/0319438 A1 | 12/2013 | Liu |
| 2013/0319439 A1 | 12/2013 | Gorelick et al. |
| 2013/0319440 A1 | 12/2013 | Capuano |
| 2013/0319989 A1 | 12/2013 | Liu |
| 2013/0319999 A1 | 12/2013 | Plojoux et al. |
| 2013/0333700 A1 | 12/2013 | Buchberger |
| 2013/0333711 A1 | 12/2013 | Liu |
| 2013/0333712 A1 | 12/2013 | Scatterday |
| 2013/0336358 A1 | 12/2013 | Liu |
| 2013/0340750 A1 | 12/2013 | Thorens et al. |
| 2013/0340775 A1 | 12/2013 | Juster et al. |
| 2013/0340778 A1 | 12/2013 | Liu |
| 2013/0340779 A1 | 12/2013 | Liu |
| 2013/0341218 A1 | 12/2013 | Liu |
| 2013/0342157 A1 | 12/2013 | Liu |
| 2014/0000636 A1 | 1/2014 | O'Connell |
| 2014/0000637 A1 | 1/2014 | O'Connell |
| 2014/0000638 A1 | 1/2014 | Sebastian et al. |
| 2014/0007891 A1 | 1/2014 | Liu |
| 2014/0007892 A1 | 1/2014 | Liu |
| 2014/0014124 A1 | 1/2014 | Glasberg et al. |
| 2014/0014125 A1 | 1/2014 | Fernando et al. |
| 2014/0014126 A1 | 1/2014 | Peleg et al. |
| 2014/0020693 A1 | 1/2014 | Thorens et al. |
| 2014/0020696 A1 | 1/2014 | Liu |
| 2014/0020697 A1 | 1/2014 | Liu |
| 2014/0034070 A1 | 2/2014 | Schennum |
| 2014/0034071 A1 | 2/2014 | Levitz et al. |
| 2014/0041655 A1 | 2/2014 | Barron et al. |
| 2014/0044857 A1 | 2/2014 | Hua |
| 2014/0048086 A1 | 2/2014 | Zhanghua |
| 2014/0048444 A1 | 2/2014 | Scatterday |
| 2014/0053856 A1 | 2/2014 | Liu |
| 2014/0053857 A1 | 2/2014 | Liu |
| 2014/0053858 A1 | 2/2014 | Liu |
| 2014/0060524 A1 | 3/2014 | Liu |
| 2014/0060527 A1 | 3/2014 | Liu |
| 2014/0060528 A1 | 3/2014 | Liu |
| 2014/0060529 A1 | 3/2014 | Zhang |
| 2014/0060554 A1 | 3/2014 | Collett et al. |
| 2014/0060555 A1 | 3/2014 | Chang et al. |
| 2014/0060556 A1 | 3/2014 | Liu |
| 2014/0062417 A1 | 3/2014 | Li |
| 2014/0069424 A1 | 3/2014 | Poston et al. |
| 2014/0069425 A1 | 3/2014 | Zhang |
| 2014/0069444 A1 | 3/2014 | Cyphert et al. |
| 2014/0076310 A1 | 3/2014 | Newton |
| 2014/0083442 A1 | 3/2014 | Scatterday |
| 2014/0083443 A1 | 3/2014 | Liu |
| 2014/0096781 A1 | 4/2014 | Sears et al. |
| 2014/0096782 A1 | 4/2014 | Ampolini et al. |
| 2014/0102463 A1 | 4/2014 | Jones |
| 2014/0103020 A1 | 4/2014 | Al-Qaffas |
| 2014/0107815 A1 | 4/2014 | Lamothe |
| 2014/0109898 A1 | 4/2014 | Li |
| 2014/0109905 A1 | 4/2014 | Yamada et al. |
| 2014/0109921 A1 | 4/2014 | Chen |
| 2014/0116455 A1 | 5/2014 | Youn |
| 2014/0123989 A1 | 5/2014 | Lamothe |
| 2014/0123990 A1 | 5/2014 | Timmermans |
| 2014/0130796 A1 | 5/2014 | Liu |
| 2014/0130797 A1 | 5/2014 | Liu |
| 2014/0130816 A1 | 5/2014 | Liu |
| 2014/0130817 A1 | 5/2014 | Li |
| 2014/0144453 A1 | 5/2014 | Capuano et al. |
| 2014/0150783 A1 | 6/2014 | Liu |
| 2014/0150784 A1 | 6/2014 | Liu |
| 2014/0150785 A1 | 6/2014 | Malik et al. |
| 2014/0150810 A1 | 6/2014 | Hon |
| 2014/0157583 A1 | 6/2014 | Ward et al. |
| 2014/0166027 A1 | 6/2014 | Fuisz et al. |
| 2014/0166028 A1 | 6/2014 | Fuisz et al. |
| 2014/0166029 A1 | 6/2014 | Weigensberg et al. |
| 2014/0166030 A1 | 6/2014 | Li |
| 2014/0174459 A1 | 6/2014 | Burstyn |
| 2014/0174968 A1 | 6/2014 | Scatterday |
| 2014/0182608 A1 | 7/2014 | Egoyants et al. |
| 2014/0182610 A1 | 7/2014 | Liu |
| 2014/0182611 A1 | 7/2014 | Liu |
| 2014/0182612 A1 | 7/2014 | Chen |
| 2014/0186015 A1 | 7/2014 | Breiwa, III |
| 2014/0196736 A1 | 7/2014 | Fernando et al. |
| 2014/0246034 A1* | 9/2014 | Terry et al. ................. 131/329 |
| 2014/0299125 A1 | 10/2014 | Buchberger |
| 2014/0305453 A1 | 10/2014 | Hon |
| 2014/0318560 A1 | 10/2014 | Hon |
| 2015/0122252 A1* | 5/2015 | Frija ..................... 128/203.23 |

FOREIGN PATENT DOCUMENTS

| | | |
|---|---|---|
| CN | 200997909 | 1/2008 |
| CN | 101116542 | 2/2008 |
| CN | 101176805 | 5/2008 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 97/48293 | 12/1997 |
| WO | WO 2007/078273 | 7/2007 |
| WO | WO 2007/131449 | 11/2007 |
| WO | WO 2010/003480 | 1/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

* cited by examiner

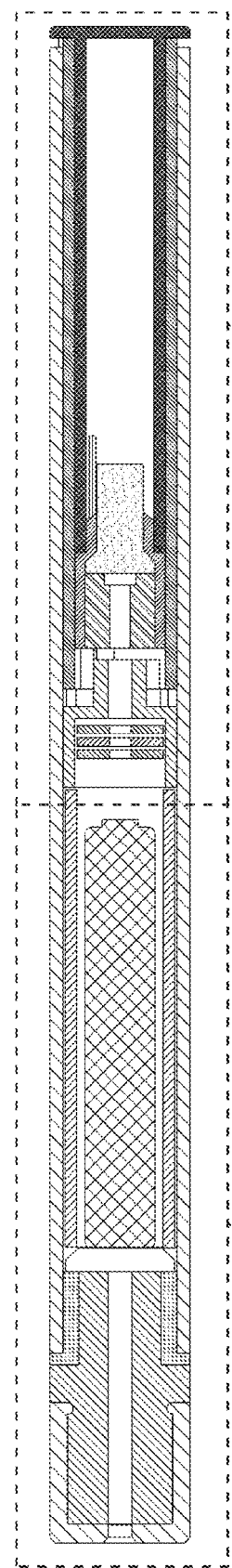

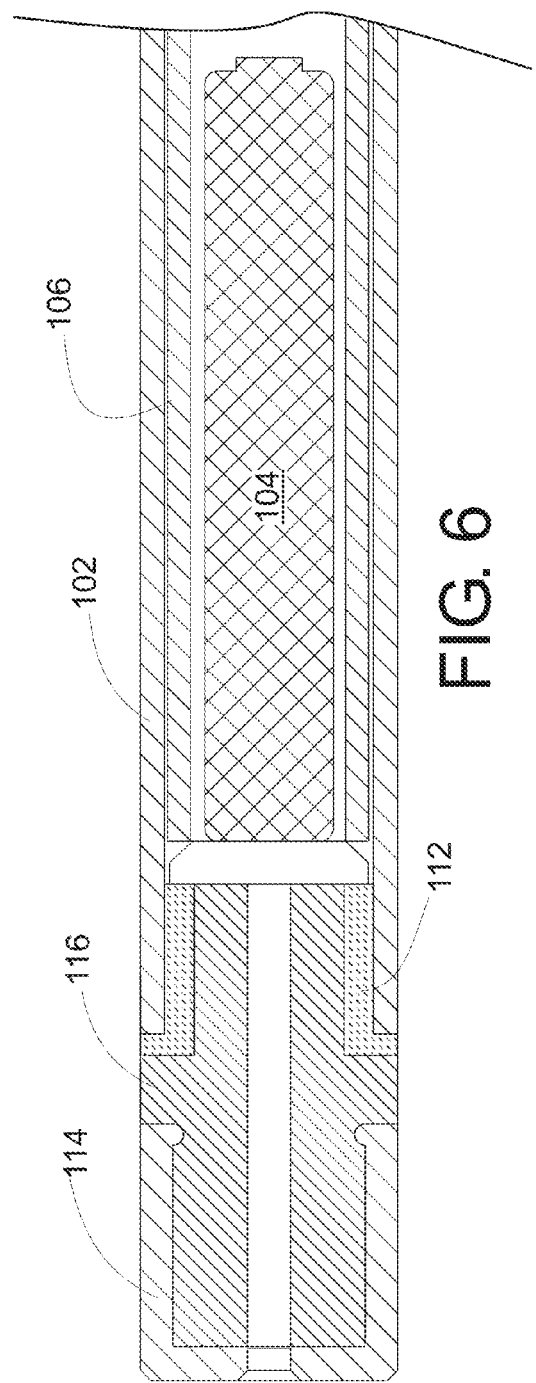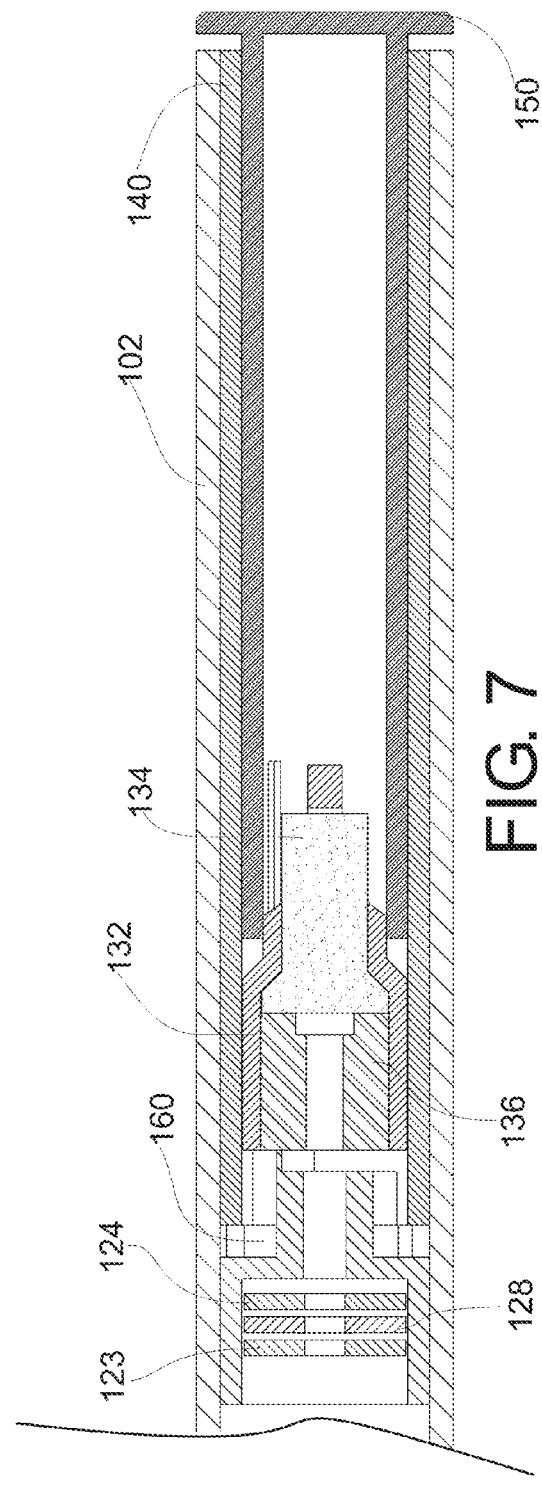

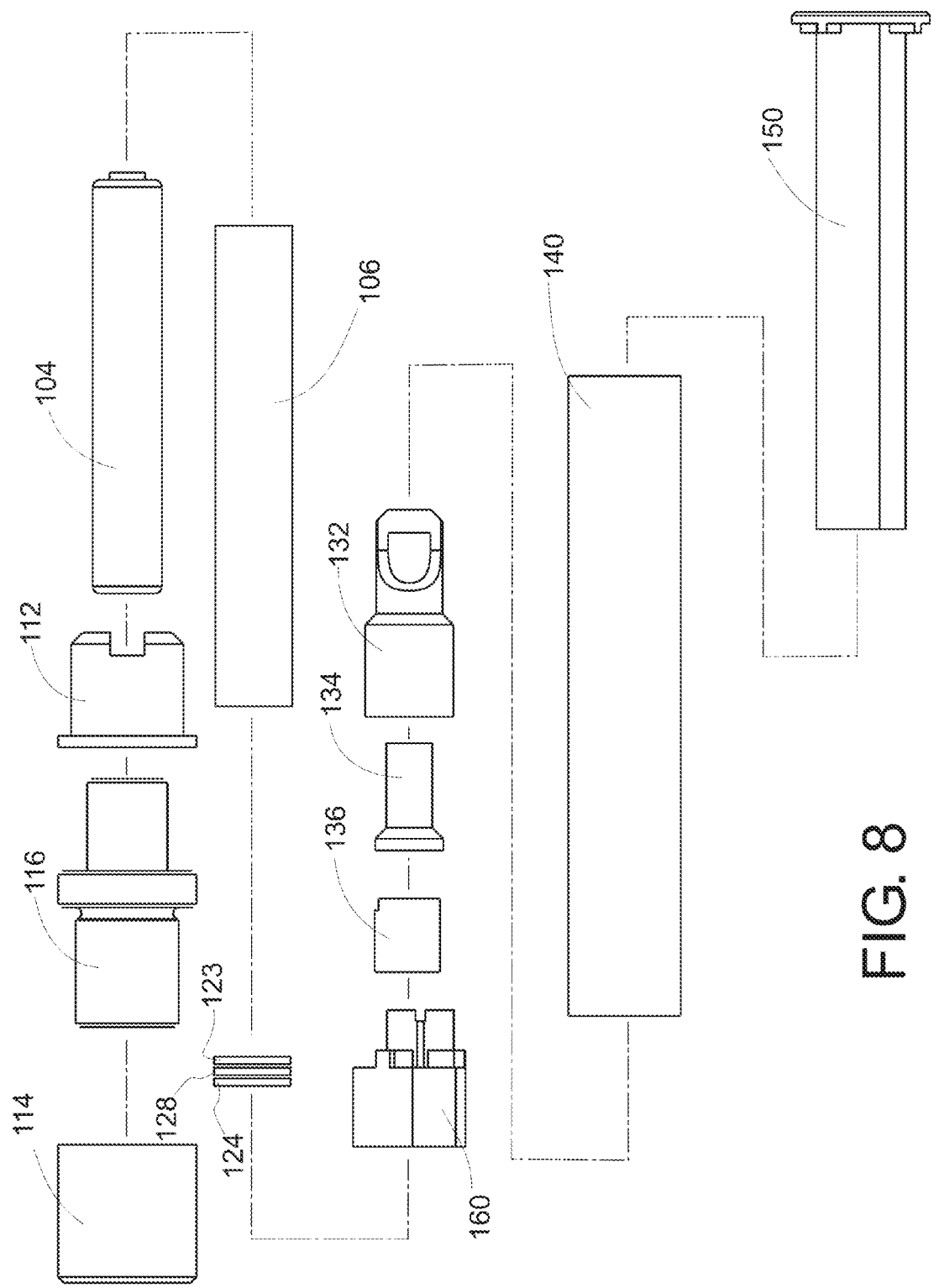

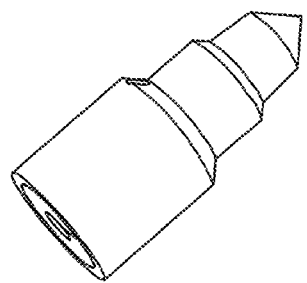
FIG. 54
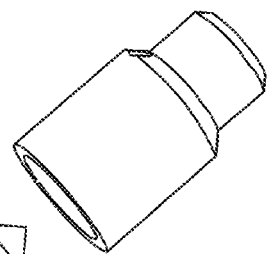
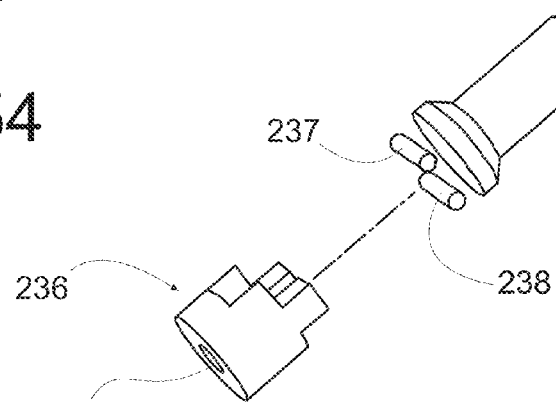
FIG. 55
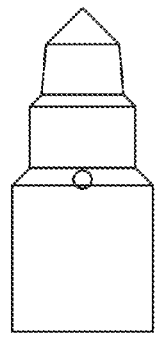
FIG. 56
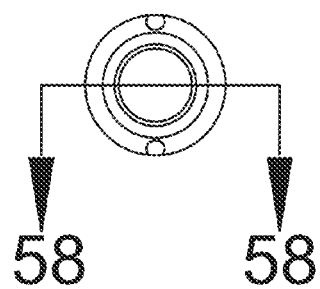
FIG. 57
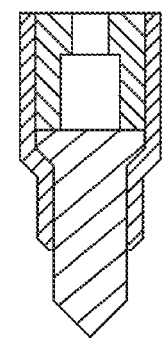
FIG. 58

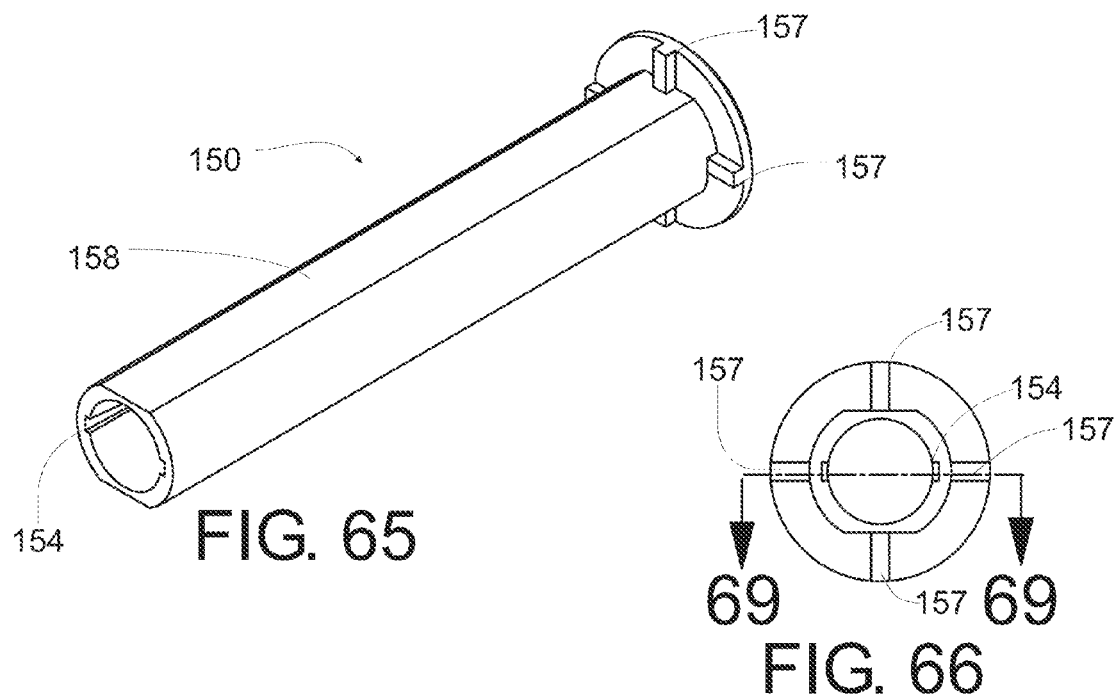
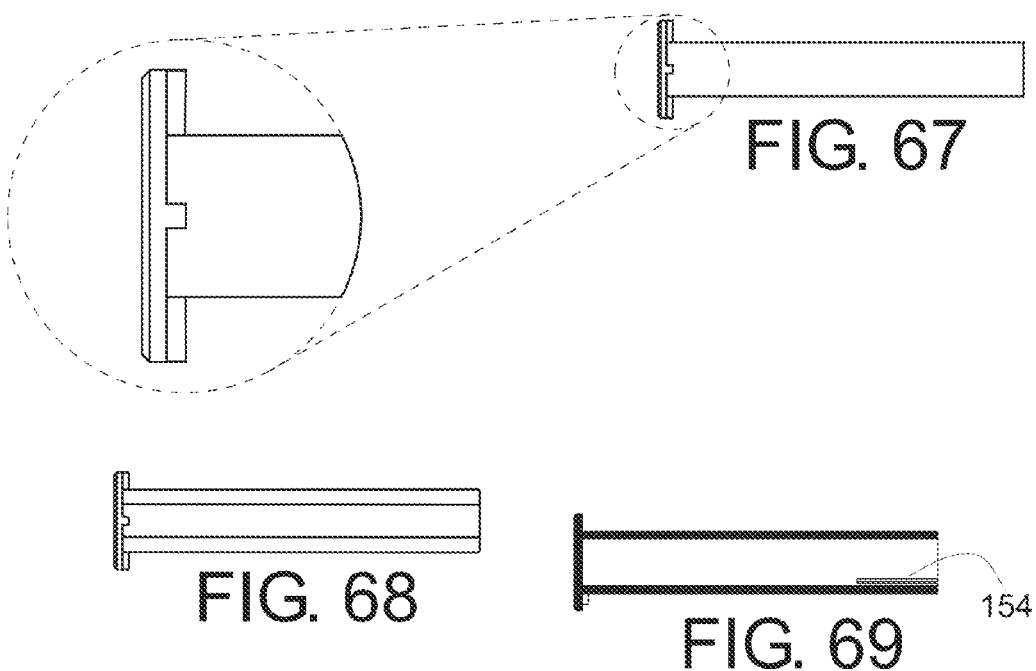

VAPORIZER CONFIGURATION, CONTROL, AND REPORTING

CROSS-REFERENCE TO RELATED APPLICATIONS

The present application claims the benefit of U.S. Provisional Application Ser. No. 61/987,005, filed May 1, 2014, and titled VAPORIZER RELATED SYSTEMS, METHODS, AND APPARATUS, which is hereby incorporated herein by reference for all purposes. The present application is also a continuation-in-part of U.S. patent application Ser. No. 12/780,876, entitled "DATA LOGGING PERSONAL VAPORIZING INHALER", filed May 15, 2010, which is hereby incorporated herein by reference for all purposes. This application is related to the following U.S. applications filed on May 15, 2010: Ser. No. 12/780,871, entitled "PERSONAL VAPORIZING INHALER WITH MOUTHPIECE COVER", Ser. No. 12/780,872, entitled "ACTIVATION TRIGGER FOR A PERSONAL VAPORIZING INHALER", Ser. No. 12/780,873, entitled "PERSONAL VAPORIZING INHALER CARTRIDGE", Ser. No. 12/780,874, entitled "ATOMIZER-VAPORIZER FOR A PERSONAL VAPORIZING INHALER", now U.S. Pat. No. 8,550,068; Ser. No. 12/780,875, entitled "PERSONAL VAPORIZING INHALER WITH INTERNAL LIGHT SOURCE", and, Ser. No. 12/780,877, entitled "PERSONAL VAPORIZING INHALER ACTIVE CASE", now U.S. Pat. No. 8,314,591; whose applications are hereby incorporated herein by reference for all purposes.

TECHNICAL FIELD

This invention relates to personal vapor inhaling units and more particularly to an electronic flameless vapor inhaler unit that stores and outputs data and that may simulate a cigarette or deliver nicotine and other medications to the oral mucosa, pharyngeal mucosa, tracheal, and pulmonary membranes.

BACKGROUND

An alternative to smoked tobacco products, such as cigarettes, cigars, or pipes is a personal vaporizer. Inhaled doses of heated and atomized flavor provide a physical sensation similar to smoking. However, because a personal vaporizer is typically electrically powered, no tobacco, smoke, or combustion is usually involved in its operation. For portability, and to simulate the physical characteristics of a cigarette, cigar, or pipe, a personal vaporizer may be battery powered. In addition, a personal vaporizer may be loaded with a nicotine bearing substance and/or a medication bearing substance. The personal vaporizer may provide an inhaled dose of nicotine and/or medication by way of the heated and atomized substance. Thus, personal vaporizers may also be known as electronic cigarettes, or e-cigarettes. Personal vaporizers may be used to administer flavors, medicines, drugs, or substances that are vaporized and then inhaled.

BRIEF DESCRIPTION OF THE DRAWINGS

FIG. 5 is a figure map of FIGS. 6 and 7.
FIG. 6 is a cross-section of the proximal portion of a personal vaporizer unit along the cut line shown in FIG. 2.
FIG. 7 is a cross-section of the distal portion of a personal vaporizer unit along the cut line shown in FIG. 2.
FIG. 8 is an exploded side view of components of a personal vaporizer unit.

FIG. 54 is a perspective view of an atomizer housing and wicks of a personal vaporizer unit.

FIG. 55 is an exploded view of the atomizer housing, wire guides, and wicks of FIG. 54.

FIG. 56 is a side view of the atomizer housing and wicks of FIG. 54.

FIG. 57 is a distal end view of the atomizer housing and wicks of FIG. 54.

FIG. 58 is a cross-section of the atomizer housing and wicks along the cut line shown in FIG. 57.

FIG. 65 is a perspective view of a cartridge of a personal vaporizer unit.

FIG. 66 is a proximal end view of the cartridge of FIG. 65.

FIG. 67 is a side view of the cartridge of FIG. 65.

FIG. 68 is a top view of the cartridge of FIG. 65.

FIG. 69 is a cross-section of the cartridge along the cut line shown in FIG. 66.

DETAILED DESCRIPTION

Figure 1:
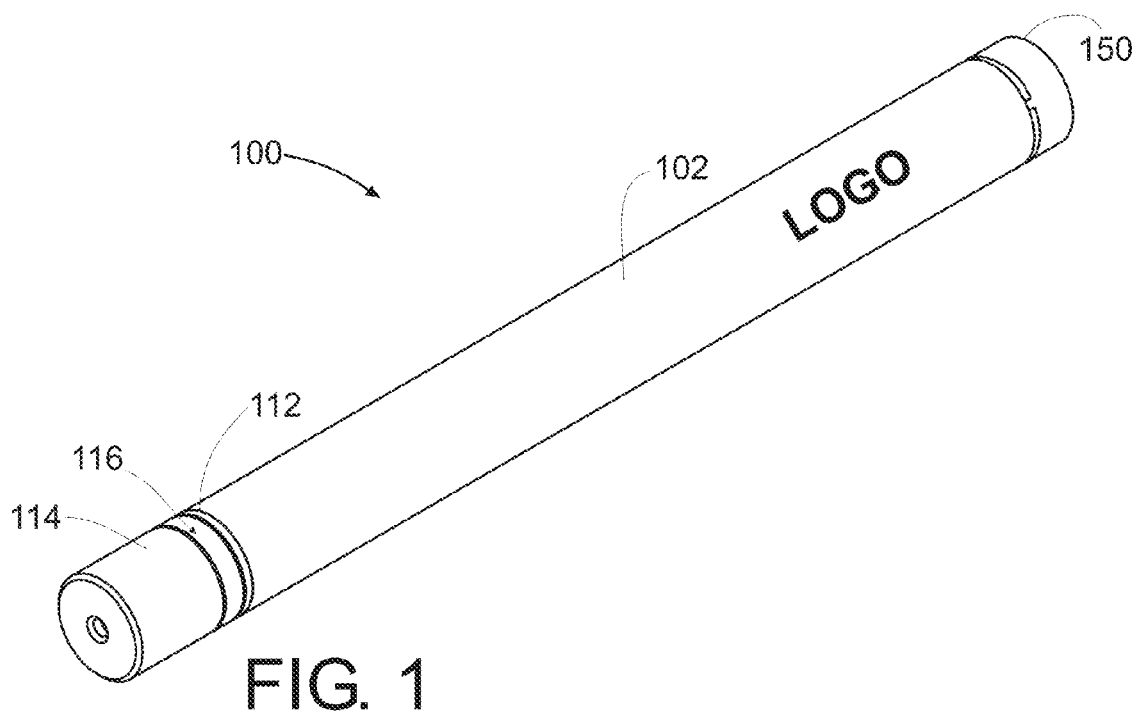
FIG. 1 is a perspective view of a personal vaporizer unit.

In an embodiment a personal vaporizer unit comprises a mouthpiece configured for contact with the mouth of a person. At least part of this mouthpiece has an antimicrobial surface. This mouthpiece may also comprise silicone rubber, thermoplastic elastomer, organosilane, silver impregnated polymer, silver impregnated thermoplastic elastomer, and/or polymer. The mouthpiece may be removed from the personal vaporizing for washing or replacement, without using a tool. The mouthpiece may be provided in different colors. Designs or other patterns may be visible on the outside of the mouthpiece.

In an embodiment, a personal vaporizer unit comprises a first conductive surface configured to contact a first body part of a person holding the personal vaporizer unit, and a second conductive surface, conductively isolated from the first conductive surface, configured to contact a second body part of the person. When the personal vaporizer unit detects a change in conductivity between the first conductive surface and the second conductive surface, a vaporizer is activated to vaporize a substance so that the vapors may be inhaled by the person holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory.

In an embodiment, a personal vaporizer unit comprises a chamber configured to receive a cartridge. The cartridge may hold a substance to be vaporized. The chamber may be configured at the distal end of the personal vaporizer unit. A user may inhale the vaporized substance at the proximal end of the personal vaporizer unit. At least one space between the exterior surface of the cartridge, and an interior surface of the chamber, may define a passage for air to be drawn from outside the personal vaporizer unit, near the distal end, through the personal vaporizer unit to be inhaled by the user along with the vaporized substance. The personal vaporizer unit may also include a puncturing element that breaks a seal on the cartridge to allow a substance in the cartridge to be vaporized. An end surface of the cartridge may be translucent to diffuse light produced internally to the personal vaporizer unit. The translucent end may be etched or embossed with letters, symbols, or other indicia that are illuminated by the light produced internally to the personal vaporizer unit.

In an embodiment, a personal vaporizer unit comprises a first wick element and a second wick element having a porous ceramic. The first wick element is adapted to directly contact a liquid held in a reservoir. The reservoir may be contained by a cartridge that is removable from the personal vaporizer unit. A heating element is disposed through the second wick element. An air gap is defined between the first wick element and the second wick element with the heating element exposed to the air gap. Air enters the first wick element through a hole in a housing holding the first wick element.

In an embodiment, a personal vaporizer unit comprises a light source internal to an opaque cylindrical housing that approximates the appearance of a smoking article. A cylindrical light tube is disposed inside the opaque cylindrical housing to conduct light emitted by the light source to an end of the opaque cylindrical housing. This allows the light to be visible outside of the opaque cylindrical housing of the vaporizer.

In an embodiment, a personal vaporizer unit comprises a microprocessor, memory, and a connector. The connector outputs data stored in the memory. The microprocessor may gather, and store in the memory, information including, but not limited to, the number of cycles the device has been triggered, the duration of the cycles, the number cartridges of fluid that are delivered. The microprocessor may also gather and store times and dates associated with the other information gathered and stored. The microprocessor may detect an empty cartridge by detecting a specific change in resistance between a wick and a housing that is equivalent to a "dry wick", and thus signifies an empty cartridge.

In an embodiment, a case comprises a cradle adapted to hold a personal vaporizer unit. The personal vaporizer unit has dimensions approximating a smoking article. The case includes a battery and at least two contacts. The two contacts may form an electrical contact with the personal vaporizer unit when the personal vaporizer unit is in the cradle. The two contacts may conduct charge from the battery to the personal vaporizer unit to charge the personal vaporizer unit. The case may also download and store data retrieved from the personnel vaporizing unit. The case may download and store this data via the at least two contacts. The case may send this data to a computer via wired or wireless links. The case may have more than one cradle and sets of contacts (e.g., two sets of two contacts in order to hold and charge two personal vaporizer units).

FIG. 1 is a perspective view of a personal vaporizer unit. In FIG. 1, personal vaporizer unit 100 comprises outer main shell 102, mouthpiece cover 114, mouthpiece 116, and mouthpiece insulator 112. The mouthpiece 116 and mouthpiece cover 114 define the proximal end of personal vaporizer unit 100. The opposite end of personal vaporizer unit 100 will be referred to as the distal end. A cartridge 150 may be inserted into the distal end of personal vaporizer unit 100. Cartridge 150 may hold the substance to be vaporized by personal vaporizer unit 100. The substance after vaporizing may be inhaled by a user holding the personal vaporizer unit 100. The substance may be in the form of a liquid or gel.

Figure 2:
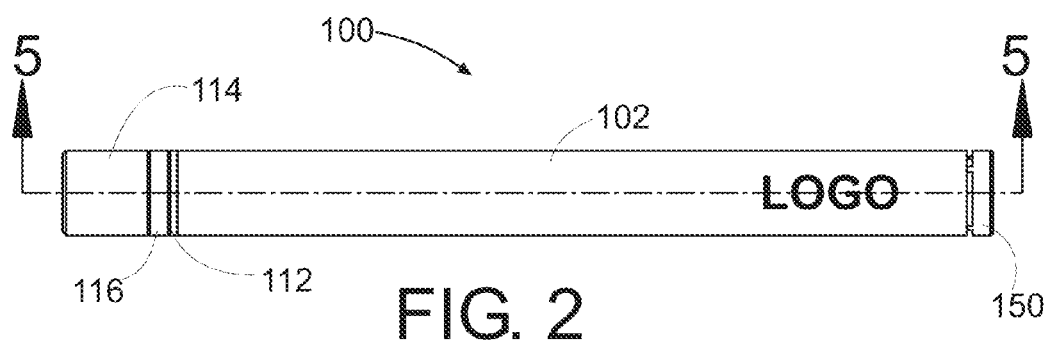
FIG. 2 is a side view of a personal vaporizer unit.

FIG. 2 is a side view of a personal vaporizer unit. FIG. 2 illustrates personal vaporizer unit 100 as viewed from the side. FIG. 2 illustrates personal vaporizer unit 100 comprising outer main shell 102, mouthpiece cover 114, mouthpiece 116, and mouthpiece insulator 112. FIG. 2 also illustrates cartridge 150 inserted into the distal end of personal vaporizer unit 100.

Figure 3:
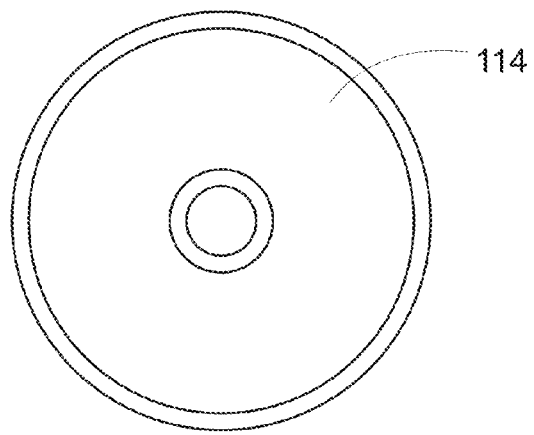
FIG. 3 is an end view of the proximal end of a personal vaporizer unit.
Figure 4A:
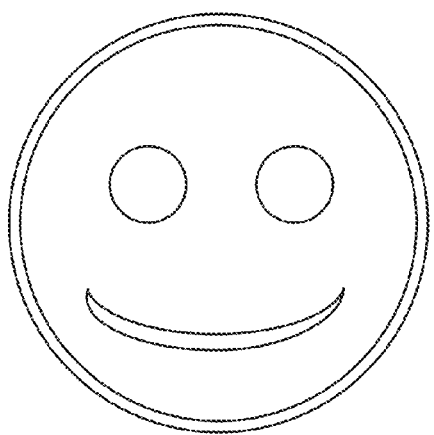
FIG. 4A is an end view of the distal end of a personal vaporizer unit having an embossed cartridge.
Figure 4:
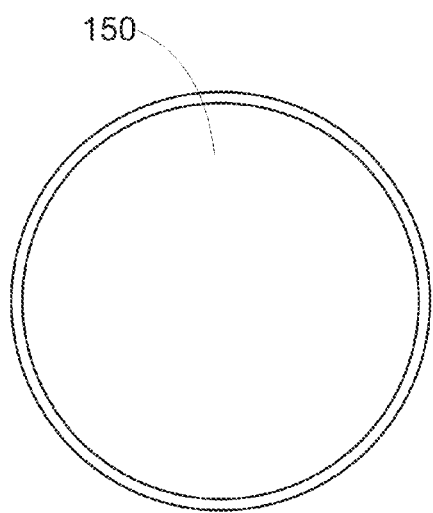
FIG. 4 is an end view of the distal end of a personal vaporizer unit.

FIG. 3 is an end view of the proximal end of a personal vaporizer unit. FIG. 3 shows the proximal end view of personal vaporizer unit 100 comprising mouthpiece cover 114. FIG. 4 is an end view of the distal end of a personal vaporizer unit. FIG. 4 shows the distal end view personal vaporizer unit 100 comprising the visible portion of cartridge 150. FIG. 4A is an alternative end view of personal vaporizer unit 100 comprising a visible portion of cartridge 150 that has visible logos, letters, or other symbols. These visible logos, letters, or other symbols may be illuminated or backlit by a light source internal to the personal vaporizer unit 100. The light source may be activated intermittently under the control of a microprocessor or other electronics internal to personal vaporizer unit 100. The light source may be activated in such a manner as to simulate the glowing ash of a cigar or cigarette.

FIG. 5 is a figure map of FIGS. 6 and 7. FIG. 6 is a cross-section of the proximal portion of a personal vaporizer unit along the cut line shown in FIG. 2. In FIG. 6, the proximal portion of personal vaporizer unit 100 comprises mouthpiece cover 114, mouthpiece 116, mouthpiece insulator 112, outer main shell 102, battery support 106, and battery 104. The mouthpiece cover 114 surrounds and is engaged with the distal end of mouthpiece 116. Mouthpiece 116 and outer main shell 102 are preferably made of an electrically conductive material(s). Mouthpiece 116 is separated from outer main shell 102 by mouthpiece insulator 112. Mouthpiece 116 and outer main shell 102 are thus electrically isolated from each other by mouthpiece insulator 112.

In an embodiment, personal vaporizer unit 100 is configured such that other main shell 102 comprises a first conductive surface configured to contact a first body part of a person holding personal vaporizer unit 100. Mouthpiece 116 comprises a second conductive surface, which is conductively isolated from the first conductive surface. This second conductive surface is configured to contact a second body part of the person. When personal vaporizer unit 100 detects a change in conductivity between the first conductive surface and the second conductive surface, a vaporizer internal to personal vaporizer unit 100 is activated to vaporize a substance in cartridge 150 so that the vapors may be inhaled by the person holding personal vaporizer unit 100. The first body part and the second body part may be a lip or parts of a hand(s). The two conductive surfaces of outer main shell 102 and mouthpiece 116, respectively, may also be used to charge battery 104 contained in the personal vaporizer unit 100. The two conductive surfaces of outer main shell 102 and mouthpiece 116, respectively, may also be used to output (or input) data stored (or to be stored) in a memory (not shown).

Battery support 106 functions to hold battery 104 in a position which is fixed relative to our main shell 102. Battery support 106 is also configured to allow air and vaporized substance to pass from the distal end of personal vaporizer unit 100 past battery 104 along one or more passageways. After air and the vapors of the vaporized substance pass by battery 104, they may pass through openings in mouthpiece 116, mouthpiece cover 114, and mouthpiece insulator 112, to be inhaled by a user.

FIG. 7 is a cross-section of the distal portion of a personal vaporizer unit along the cut line shown in FIG. 2. In FIG. 7, the distal end portion of personal vaporizer unit 100 comprises outer main shell 102, light pipe sleeve 140, and atomizer housing 132, distal wick 134, proximal wick 136, PC board 123, PC board 124, spacer 128, and main housing 160. FIG. 7 also illustrates cartridge 150 inserted into the distal end of personal vaporizer unit 100. As can be seen in FIG. 7, cartridge 150 may hold a substance (e.g., a liquid or gel) in direct contact with distal wick 134. The substance may be drawn through distal wick 134 to be vaporized inside atomizer assembly. The atomizer assembly comprises atomizer housing 132, distal wick 134, proximal wick 136, and a heating element (not shown).

Figure 9:
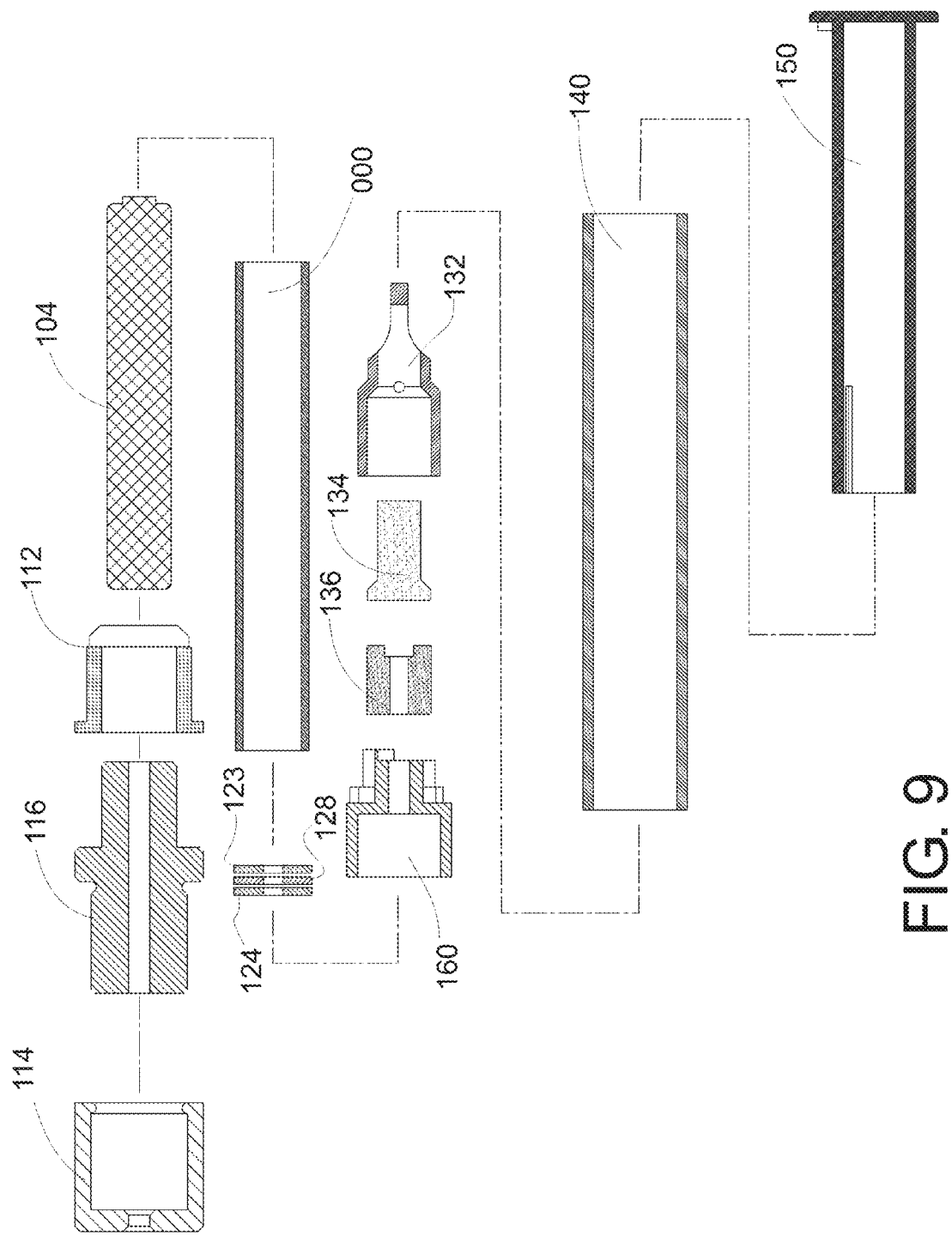
FIG. 9 is an exploded cross-section of components of a personal vaporizer unit along the cut line shown in FIG. 2.

FIG. 8 is an exploded side view of components of a personal vaporizer unit. FIG. 9 is an exploded cross-section of components of a personal vaporizer unit along the cut line shown in FIG. 2.

In FIGS. 8 and 9, personal vaporizer unit 100 comprises (from left to right) mouthpiece cover 114, mouthpiece 116, mouthpiece insulator 112, battery 104, battery support 106, PC board 123, spacer 128, PC board 124, main housing 160, proximal wick 136, distal wick 134, atomizer housing 132, light pipe sleeve 140, and cartridge 150. Mouthpiece cover 114 surrounds and covers the proximal end of mouthpiece 116. The distal end of mouthpiece 116 is inserted into mouthpiece insulator 112. Battery 104 is held in place by battery support 106. PC board 123, spacer 128 and PC board 124 are disposed within main housing 160. Proximal wick 136 and distal wick 134 are disposed within atomizer housing 132.

Atomizer housing 132 (and therefore proximal wick 136, distal wick 134) are disposed inside light pipe sleeve 140 and main shell 102. (Note: for clarity, main shell 102 is not shown in FIGS. 8 and 9.) Light pipe sleeve 140 is disposed within main shell 102. Light pipe sleeve 140 is positioned such that light emitted from a light source mounted on PC board 124 may be conducted via light pipe sleeve 140 to a location where it is visible on the outside of personal vaporizer unit 100.

Cartridge 150 is disposed within light pipe sleeve 140. When assembled, a substance contained within cartridge 150 is held in direct contact with distal wick 134. When cartridge 150 is inserted into personal vaporizer unit 100 atomizer housing 132 or distal wick 134 may puncture a seal or cap that contains the substance to be vaporized within cartridge 150. Once punctured, the substance held within a reservoir of cartridge 150 may come in direct contact with distal wick 134.

Figure 10:
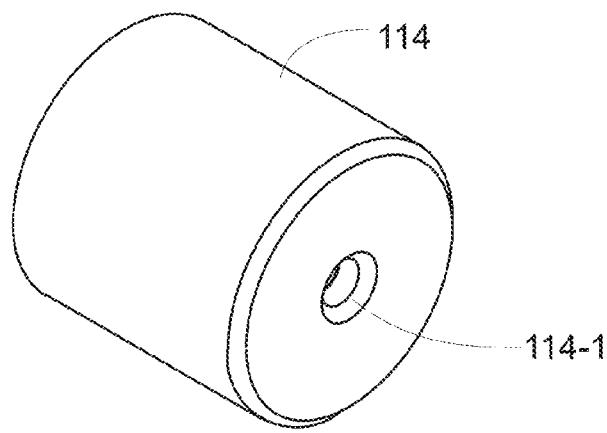
FIG. 10 is a perspective view of a mouthpiece cover of a personal vaporizer unit.
Figure 11:
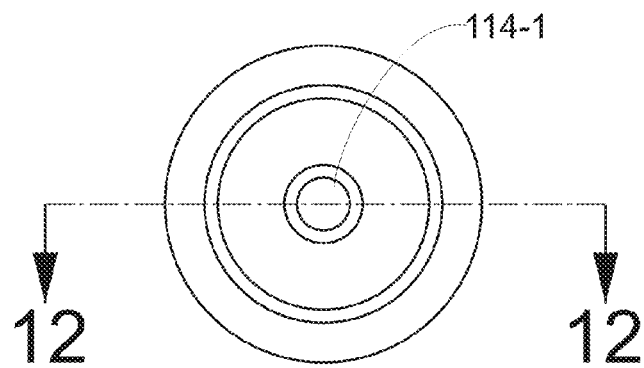
FIG. 11 is a distal end view of the mouthpiece cover of FIG. 10.
Figure 12:
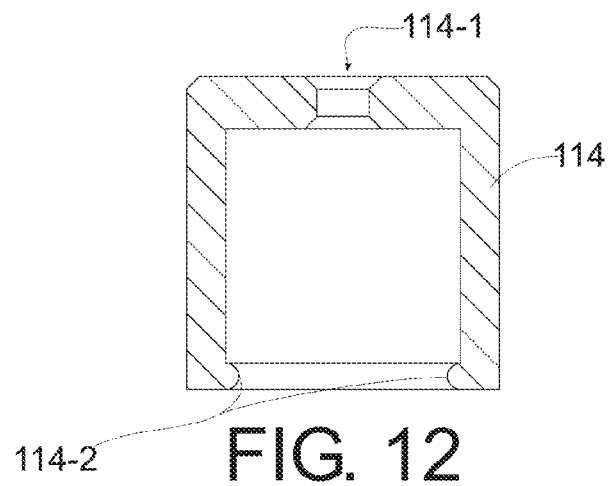
FIG. 12 is a cross-section of the mouthpiece cover along the cut line shown in FIG. 11.

FIG. 10 is a perspective view of a mouthpiece cover of a personal vaporizer unit. FIG. 11 is a distal end view of the mouthpiece cover of FIG. 10. FIG. 12 is a cross-section of the mouthpiece cover along the cut line shown in FIG. 11. As can be seen in FIGS. 10-12, mouthpiece cover 114 has an opening 114-1 that allows air and the vaporized substance to be drawn through mouthpiece cover 114. Mouthpiece cover 114 is configured for contact with the mouth of a person. In an embodiment, at least part of the mouthpiece cover has an antimicrobial surface. This antimicrobial surface of mouthpiece cover 114 may comprise, but is not limited to: silicone rubber, thermoplastic elastomer, organosilane, silver impregnated polymer, silver impregnated thermoplastic elastomer, and/or polymer. Mouthpiece cover 114 is also configured to be removable from personal vaporizer unit 100 by a user without the use of tools. This allows mouthpiece cover 114 to be replaced and/or washed. In an embodiment, mouthpiece cover 114 may be held in place on personal vaporizer unit 100 by annular ridge 114-2 which interfaces with a groove on mouthpiece 116 of personal vaporizer unit 100 to secure mouthpiece cover 114 in place. In another embodiment, mouthpiece cover 114 may be held in place on personal vaporizer unit 100 by a friction fit.

Figure 13:
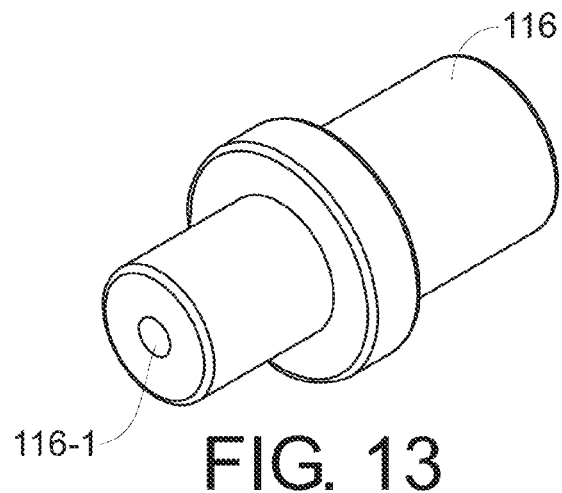
FIG. 13 is a perspective view of a mouthpiece of a personal vaporizer unit.
Figure 14:
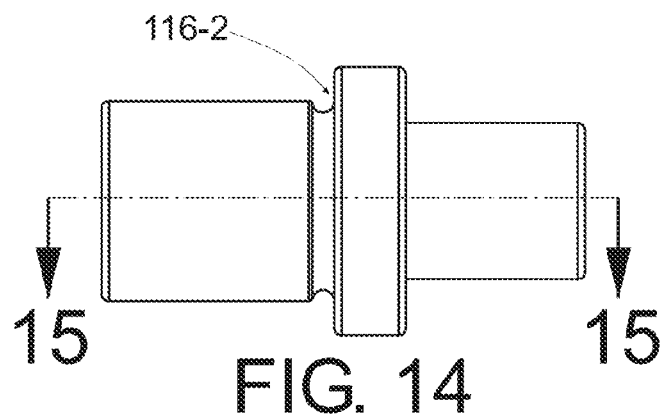
FIG. 14 is a side view of the mouthpiece of FIG. 13.
Figure 15:
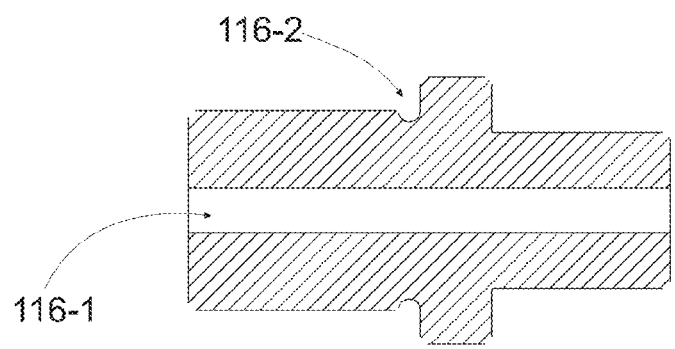
FIG. 15 is a cross-section of the mouthpiece along the cut line shown in FIG. 14.

FIG. 13 is a perspective view of a mouthpiece of a personal vaporizer unit. FIG. 14 is a side view of the mouthpiece of FIG. 13. FIG. 15 is a cross-section of the mouthpiece along the cut line shown in FIG. 14. As can be seen in FIGS. 13-15, mouthpiece 116 has a passageway 116-1 that allows air and the vaporized substance to be drawn through mouthpiece 116. Mouthpiece 116 may comprise a conductive surface or material configured to contact a first body part of a person holding personal vaporizer unit 100. This first body part may be part of a hand, or at least one lip of the person holding personal vaporizer unit 100. In an embodiment, mouthpiece 116 has an annular groove 116-2 around an outside surface. This groove is configured to receive annular ridge 114-2. Thus, annular groove 116-2 helps secure mouthpiece cover 114 to personal vaporizer unit 100.

Figure 16:
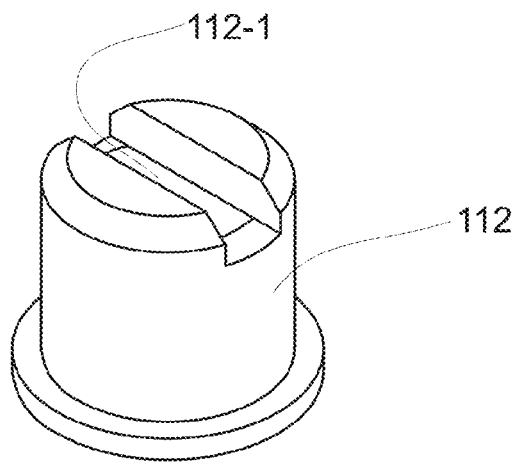
FIG. 16 is a perspective view of a mouthpiece insulator of a personal vaporizer unit.
Figure 17:
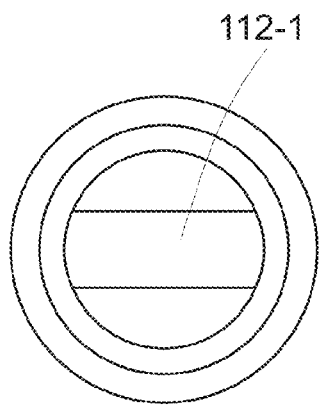
FIG. 17 is a distal end view of the mouthpiece insulator of FIG. 16.
Figure 18:
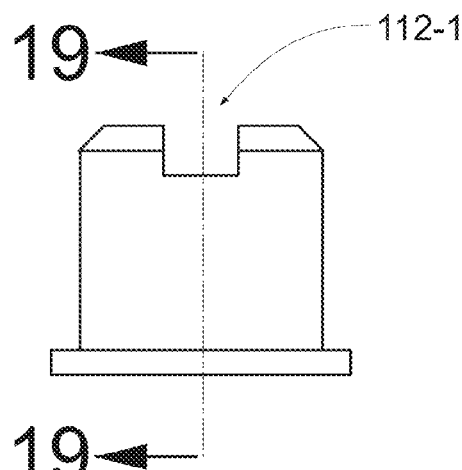
FIG. 18 is a side view of the mouthpiece insulator of FIG. 16.
Figure 19:
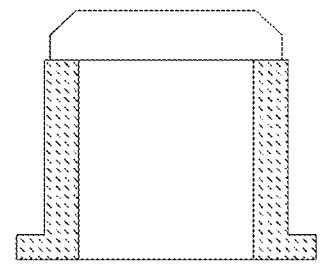
FIG. 19 is a cross-section of the mouthpiece insulator along the cut line shown in FIG. 18.

FIG. 16 is a perspective view of a mouthpiece insulator of a personal vaporizer unit. FIG. 17 is a distal end view of the mouthpiece insulator of FIG. 16. FIG. 18 is a side view of the mouthpiece insulator of FIG. 16. FIG. 19 is a cross-section of the mouthpiece insulator along the cut line shown in FIG. 18. As discussed previously, mouthpiece insulator 112 is disposed between main shell 102 and mouthpiece 116. As can be seen in FIGS. 16-18, mouthpiece insulator 112 has a passageway 112-1 that allows air and the vaporized substance to be drawn through mouthpiece insulator 112. Because mouthpiece insulator 112 is disposed between main shell 102 and mouthpiece 116, mouthpiece insulator 112 can electrically isolate main shell 102 and mouthpiece 116. Thus, in an embodiment, mouthpiece insulator 112 comprises, or is made of, a non-electrically conductive material. This electrical isolation between main shell 102 and mouthpiece 116 allow electrical impedance changes between main shell 102 and mouthpiece 116 to be detected.

For example, a first conductive surface on mouthpiece 116 may be configured to contact a first body part of a person holding personal vaporizer unit 100. A second conductive surface on main shell 102 (which is conductively isolated from said first conductive surface by mouthpiece insulator 112) may be configured to contact a second body part of the person. Personal vaporizer unit 100 may then activate in response to detecting a change in conductivity between the first conductive surface and the second conductive surface. In an embodiment, this change in conductivity may comprise a drop in impedance between the first conductive surface and the second conductive surface. In an embodiment, the change in conductivity may comprise a change in capacitance between the first conductive surface and the second conductive surface. The first body part may be a finger. The second body part may be a lip. The second body part may be a second finger. In an embodiment, the first conductive surface and the second conductive surfaces may be used to pass a charging current to battery 104. The first and second conductive surfaces may also be used to transfer data to or from personal vaporizer unit 100.

Figure 20:
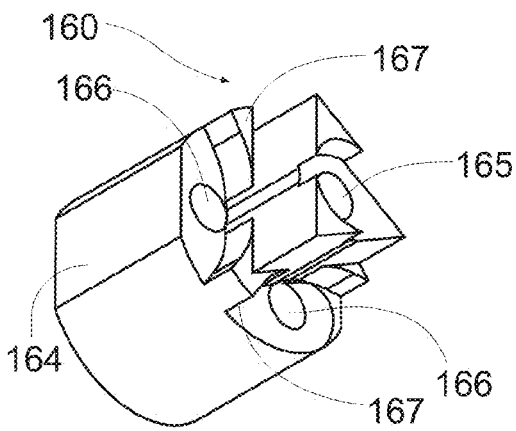
FIG. 20 is a perspective view of a main housing of a personal vaporizer unit.
Figure 21:
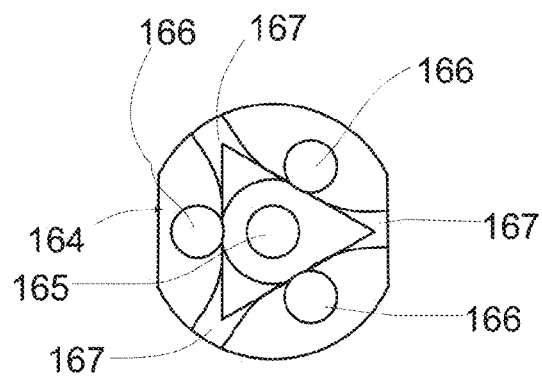
FIG. 21 is a distal end view of the main housing of FIG. 20.
Figure 22:
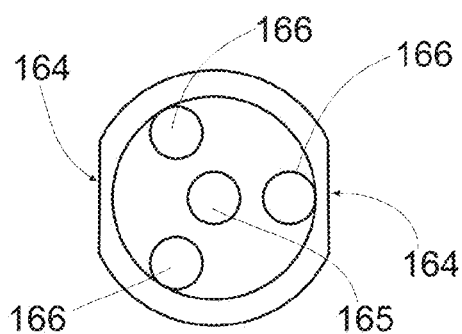
FIG. 22 is a proximal end view of the main housing of FIG. 20.
Figure 23:
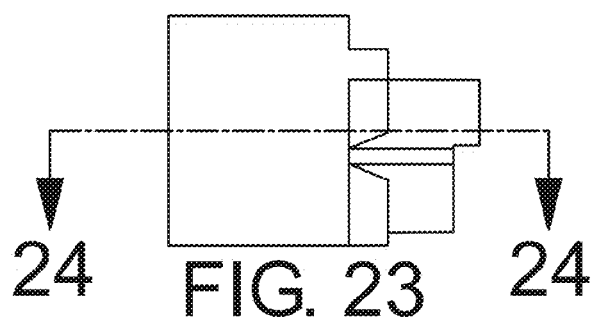
FIG. 23 is a side view of the main housing of FIG. 20.
Figure 24:
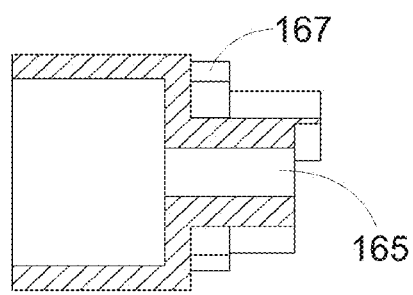
FIG. 24 is a cross-section of the main housing along the cut line shown in FIG. 23.

FIG. 20 is a perspective view of a main housing of a personal vaporizer unit. FIG. 21 is a distal end view of the main housing of FIG. 20. FIG. 22 is a proximal end view of the main housing of FIG. 20. FIG. 23 is a side view of the main housing of FIG. 20. FIG. 24 is a cross-section of the main housing along the cut line shown in FIG. 23. Main housing 160 is configured to hold PC-boards 123 and 124, and spacer 128. Main housing 160 is configured to fit within main shell 102 via a friction fit. Main housing 160 has several holes 166 that allow light generated by a light source(s) on PC-board 124 to pass. Once this light passes through holes 166, it may be coupled into light pipe sleeve 140 where it is conducted to a visible location on the outside of personal vaporizer unit 100.

Main housing 160 also has a hole 165 that allows an electrical conductor (not shown) to run from PC-board 123 or PC-board 124 through main housing 160. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 160 may also have a flat surface 164 (or other geometry) forming a galley that is configured to allow the vaporized substance and air to pass between the main housing 160 and the main shell 102. Once the vaporized substance and air pass by main housing 160, they may travel through passageway 112-1, passageway 116-1, and opening 114-1 to be inhaled by a user of personal vaporizer unit 100. The exterior of main housing 160 may also have one or more standoffs 167 (or other geometries) that are configured to allow air and the vaporized substance to reach the passageway formed by flat surface 164 and main shell 102.

Figure 25:
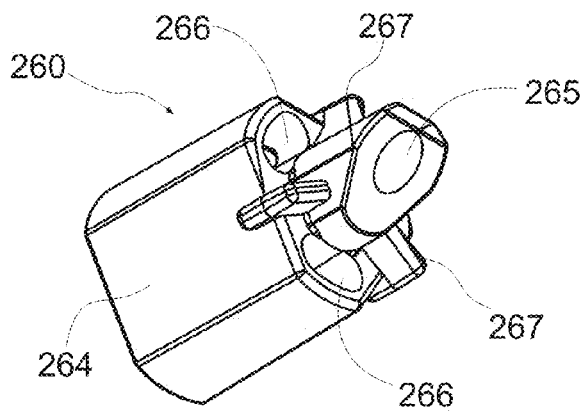
FIG. 25 is a perspective view of a main housing of a personal vaporizer unit.
Figure 26:
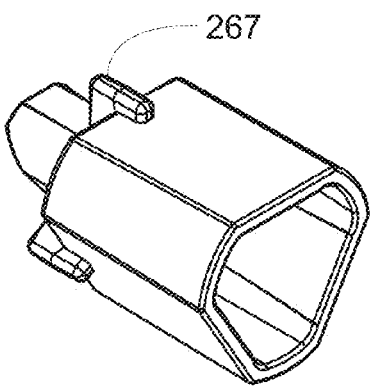
FIG. 26 is a second perspective view of the main housing of FIG. 25.
Figure 27:
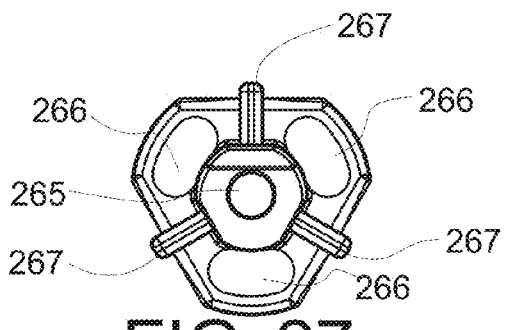
FIG. 27 is a distal end view of the main housing of FIG. 25.
Figure 29:
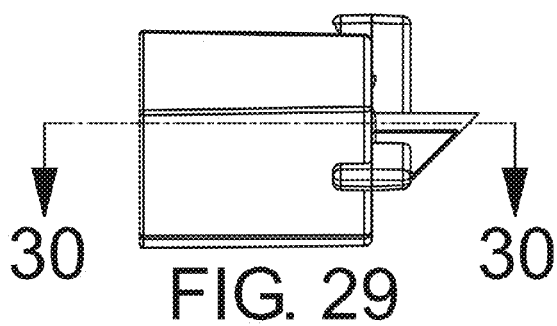
FIG. 29 is a side view of the main housing of FIG. 25.
Figure 28:
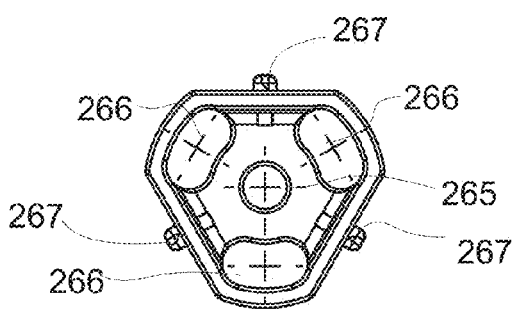
FIG. 28 is a proximal end view of the main housing of FIG. 25.
Figure 30:
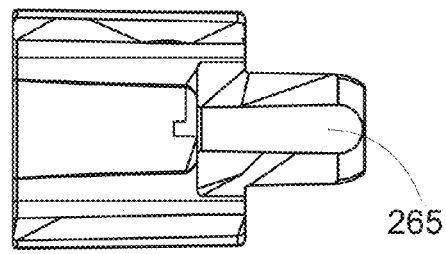
FIG. 30 is a cross-section of the main housing along the cut line shown in FIG. 29.

FIG. 25 is a perspective view of a main housing of a personal vaporizer unit. FIG. 26 is a second perspective view of the main housing of FIG. 25. FIG. 27 is a distal end view of the main housing of FIG. 25. FIG. 28 is a proximal end view of the main housing of FIG. 25. FIG. 29 is a side view of the main housing of FIG. 25. FIG. 30 is a cross-section of the main housing along the cut line shown in FIG. 29. Main housing 260 may be used as an alternative embodiment to main housing 160.

Main housing 260 is configured to hold PC-boards 123 and 124, and spacer 128. Main housing 260 is configured to fit within main shell 102 via a friction fit. Main housing 260 has several holes 266 that allow light generated by a light source(s) on PC-board 124 to pass. Once this light passes through holes 266, it may be coupled into light pipe sleeve 140 where it is conducted to a visible location on the outside of personal vaporizer unit 100.

Main housing 260 also has a hole 265 that allows an electrical conductor (not shown) to run from PC-board 123 or PC-board 124 through main housing 260. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 260 may also have flat surfaces 264 (or other geometry) that form a galley that is configured to allow the vaporized substance and air to pass between the main housing 260 and the main shell 102. Once the vaporized substance and air pass by main housing 260, they may travel through passageway 112-1, passageway 116-1, and opening 114-1 to be inhaled by a user of personal vaporizer unit 100. The exterior of main housing 260 may also have one or more standoffs 267 (or other geometries) that are configured to allow air and the vaporized substance to reach the passageway formed by flat surfaces 264 and main shell 102.

Figure 31:
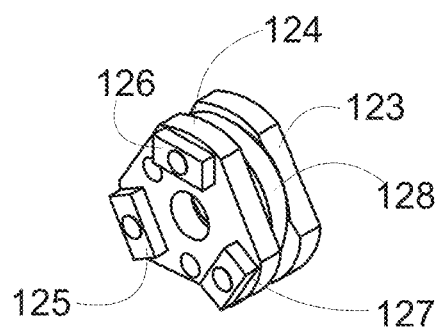
FIG. 31 is a perspective view of a printed circuit board (PCB or PC-board) assembly of a personal vaporizer unit.
Figure 32:
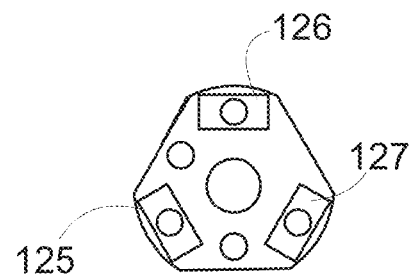
FIG. 32 is a distal end view of the PCB assembly of FIG. 31.
Figure 33:
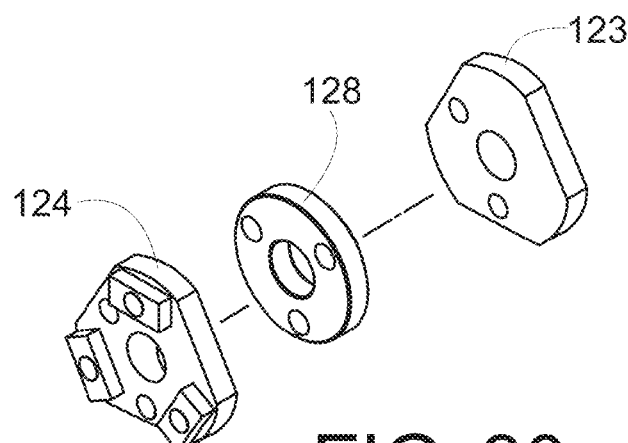
FIG. 33 is a perspective exploded view of the PCB assembly of FIG. 31.
Figure 34:
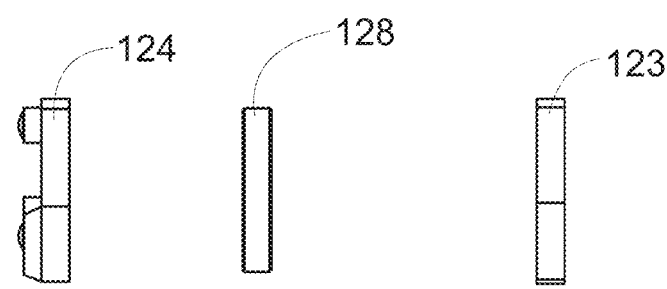
FIG. 34 is a side exploded view of the PCB assembly of FIG. 31.

FIG. 31 is a perspective view of a printed circuit board assembly of a personal vaporizer unit. FIG. 32 is a distal end view of the PCB assembly of FIG. 31. FIG. 33 is a perspective exploded view of the PCB assembly of FIG. 31. FIG. 34 is a side exploded view of the PCB assembly of FIG. 31. As can be seen in FIGS. 31-34, the PCB assembly is comprised of PC-board 123 and PC-board 124 separated by a spacer 128. PC-board 124 may have mounted upon it light emitting diodes (LEDs) 125-127 or other light sources. LEDs 125-127 are configured and positioned such that when they produce light, that light passes through holes 166 or 266 in main housings 160 and 260, respectively. This light may then be conducted by light pipe sleeve 140 to a location where it will be visible exterior to personal vaporizer unit 100.

PC-board 123 may have mounted on it a microprocessor, memory, or other circuitry (not shown) to activate or otherwise control personal vaporizer unit 100. This microprocessor may store data about the operation of personal vaporizer unit 100 in the memory. For example, the microprocessor may determine and store the number of cycles personal vaporizer unit 100 has been triggered. The microprocessor may also store a time and/or date associated with one or more of these cycles. The microprocessor may cause this data to be output via a connector. The connector may be comprised of the first and second conductive surfaces of mouthpiece 116 and/or main shell 102.

In an embodiment, the microprocessor may determine a duration associated with various cycles where personal vaporizer unit 100 has been triggered. These durations (or a number based on these duration, such as an average) may be stored in the memory. The microprocessor may cause these numbers to be output via the connector. The microprocessor may determine an empty cartridge condition and stores a number associated with a number of times said empty cartridge condition occurs. The microprocessor, or other circuitry, may determine an empty cartridge condition determined based on a resistance between atomizer housing 132 or 232 and a wick 134, 234, 136, or 236. The microprocessor may also store a time and/or date associated with one or more of these empty cartridge conditions. The number of times an empty cartridge condition is detected, and or times and/or dates associated with these empty cartridge conditions may be output via the connector.

Battery 104, PC-board 123, PC-board 124, and all electronics internal to personal vaporizer unit 100 may be sealed in a plastic or plastic and epoxy compartment within the device. This compartment may include main housing 160 or 260. All penetrations in this compartment may be sealed. Thus, only wires will protrude from the compartment. The compartment may be filled with epoxy after the assembly of battery 104, PC-board 123, PC-board 124, and LEDs 125-127. The compartment may be ultrasonically welded closed after assembly of battery 104, PC-board 123, PC-board 124, and LEDs 125-127. This sealed compartment is configured such that all vapor within personal vaporizer unit 100 does not come in contact with the electronics on PC-boards 123 or 124.

Figure 35:
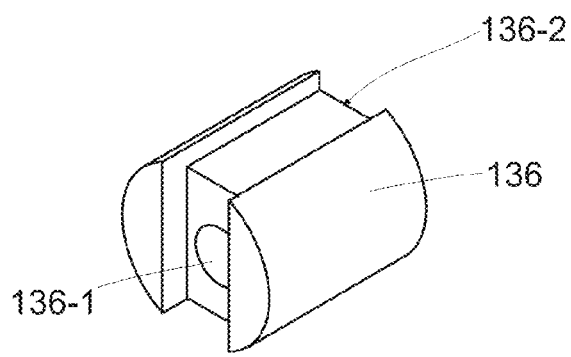
FIG. 35 is a perspective view of a proximal wick element of a personal vaporizer unit.
Figure 35A:
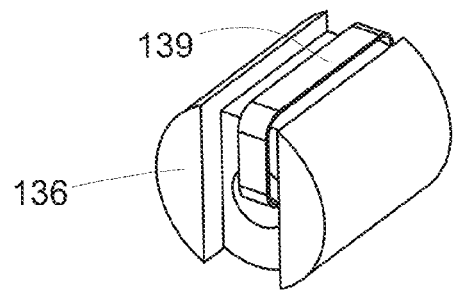
FIG. 35A is a perspective view of a heating element disposed through a proximal wick element of a personal vaporizer unit.
Figure 35B:
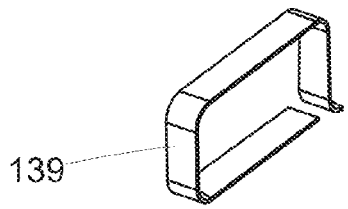
FIG. 35B is a perspective view of a heating element of a personal vaporizer unit.
Figure 36:
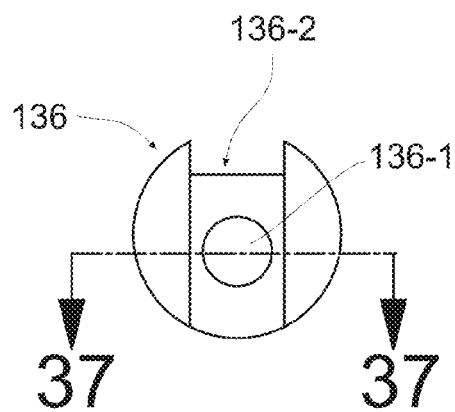
FIG. 36 is a distal end view of the wick element of FIG. 35.
Figure 37:
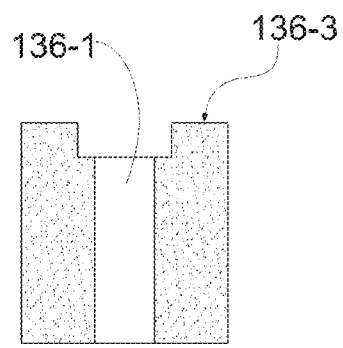
FIG. 37 is a cross-section of the wick element along the cut line shown in FIG. 35.

FIG. 35 is a perspective view of a proximal wick element of a personal vaporizer unit. FIG. 35A is a perspective view of a heating element disposed through a proximal wick element of a personal vaporizer unit. FIG. 35B is a perspective view of a heating element of a personal vaporizer unit. FIG. 36 is a distal end view of the wick element of FIG. 35. FIG. 37 is a cross-section of the wick element along the cut line shown in FIG. 35. Proximal wick 136 is configured to fit within atomizer housing 132. As can be seen in FIGS. 35-37, proximal wick 136 includes internal wire passageway 136-1 and external wire passageway 136-2. These wire passageways allows a conductor or a heating element 139 to be positioned through proximal wick 136 (via internal wire passageway 136-1). This conductor or heating element 139 may also be positioned in external wire passageway 136-2.

Thus, as shown in FIG. 35A, a conductor or heating element 139 may be wrapped around a portion of proximal wick 136 by running the conductor or heating element 139 through internal wire passageway 136-1, around the distal end of proximal wick 136, and through external wire passageway 136-2 to return to approximately its point of origin. The heating element 139 may, when personal vaporizer 100 is activated, heat proximal wick 136 in order to facilitate vaporization of a substance.

Figure 38:
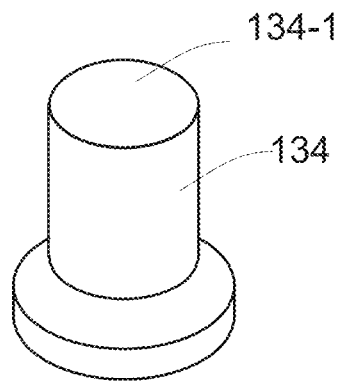
FIG. 38 is a perspective view of a distal wick element of a personal vaporizer unit.
Figure 39:
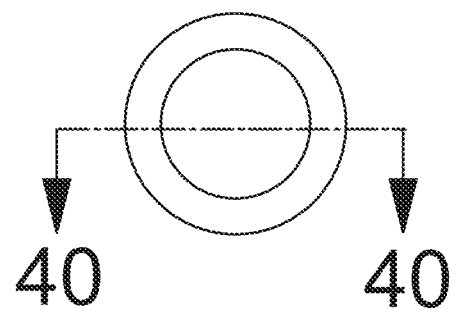
FIG. 39 is a distal end view of the wick element of FIG. 38.
Figure 40:
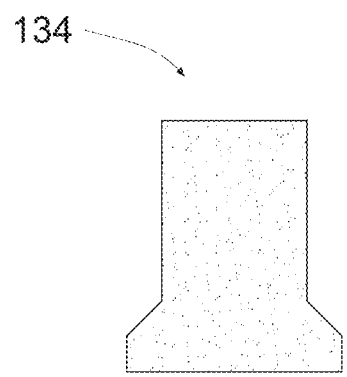
FIG. 40 is a cross-section of the wick element along the cut line shown in FIG. 39.

FIG. 38 is a perspective view of a distal wick element of a personal vaporizer unit. FIG. 39 is a distal end view of the wick element of FIG. 38. FIG. 40 is a cross-section of the wick element along the cut line shown in FIG. 39. Distal wick 134 is configured to fit within atomizer housing 132. As can be seen in FIGS. 38-40, distal wick 134 comprises two cylinders of different diameters. A chamfered surface transitions from the smaller diameter of the distal end of distal wick 134 to a larger diameter at the proximal end of distal wick 134. The cylinder at the distal end terminates with a flat surface end 134-1. This flat surface end 134-1 is the end of distal wick 134 is a surface that is placed in direct contact with a substance to be vaporized when cartridge 150 is inserted into the distal end of personal vaporizer 100. The proximal end of distal wick 134 is typically in contact with proximal wick 136. However, at least a part of proximal wick 136 and distal wick 134 are separated by an air gap. When distal wick 134 and proximal wick 136 are used together, this air gap is formed between distal wick 134 and proximal wick 136 by stand offs 136-3 as shown in FIG. 37.

Figure 41:
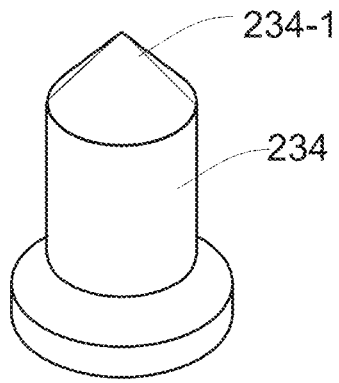
FIG. 41 is a perspective view of a distal wick element of a personal vaporizer unit.
Figure 42:
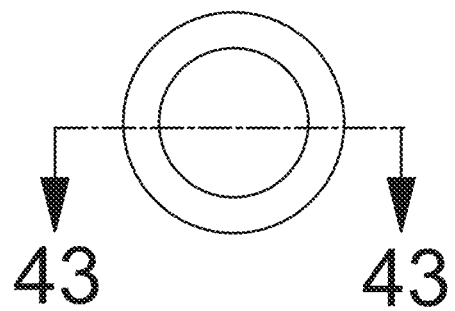
FIG. 42 is a distal end view of the wick element of FIG. 41.
Figure 43:
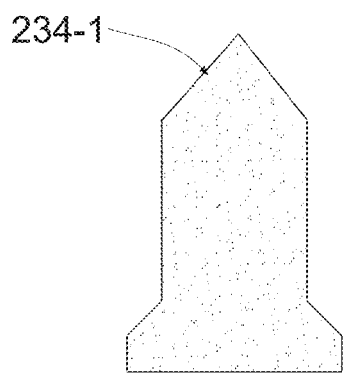
FIG. 43 is a cross-section of the wick element along the cut line shown in FIG. 42.

FIG. 41 is a perspective view of a distal wick element of a personal vaporizer unit. FIG. 42 is a distal end view of the wick element of FIG. 41. FIG. 43 is a cross-section of the wick element along the cut line shown in FIG. 42. Proximal wick 234 may be used as an alternative embodiment to distal wick 134. Proximal wick 234 is configured to fit within atomizer housing 232. As can be seen in FIGS. 41-43, proximal wick 234 comprises two cylinders of different diameters, and a cone or pointed end 234-1. A chamfered surface transitions from the smaller diameter of the distal end of proximal wick 234 to a larger diameter at the proximal end of proximal wick 234. The cylinder at the distal end terminates with a pointed end 234-1. This pointed end 234-1 is the end of proximal wick 234 that is in direct contact with a substance to be vaporized. This pointed end 234-1 may also break a seal on cartridge 150 to allow the substance to be vaporized to come in direct contact with proximal wick 234. The proximal end of proximal wick 234 is typically in contact with proximal wick 136. However, at least a part of proximal wick 136 and proximal wick 234 are separated by an air gap. When distal wick 134 and proximal wick 236 are used together, this air gap is formed between proximal wick 234 and proximal wick 136 by stand offs 136-3 as shown in FIG. 37.

Figure 44:
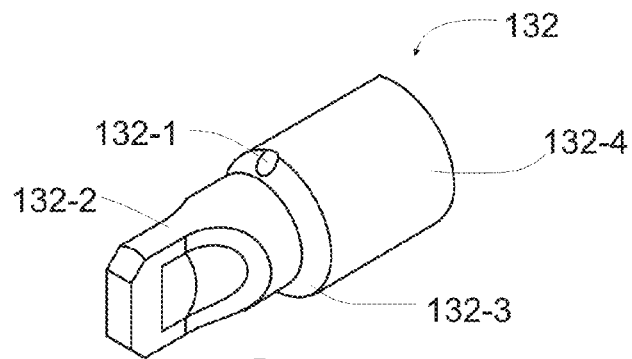
FIG. 44 is a perspective view of an atomizer housing of a personal vaporizer unit.
Figure 45:
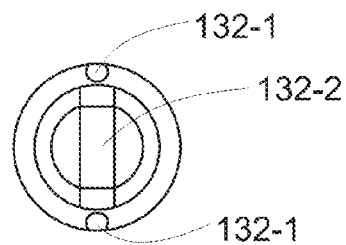
FIG. 45 is a distal end view of the atomizer housing of FIG. 44.
Figure 46:
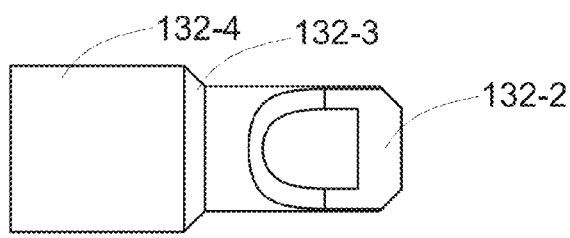
FIG. 46 is a side view of the atomizer housing of FIG. 44.
Figure 47:
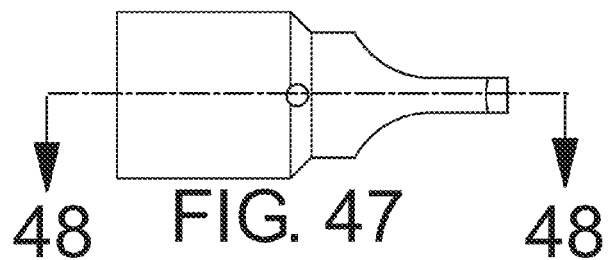
FIG. 47 is a top view of the atomizer housing of FIG. 44.
Figure 48:
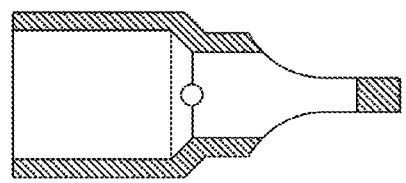
FIG. 48 is a cross-section of the atomizer housing along the cut line shown in FIG. 47.

FIG. 44 is a perspective view of an atomizer housing of a personal vaporizer unit. FIG. 45 is a distal end view of the atomizer housing of FIG. 44. FIG. 46 is a side view of the atomizer housing of FIG. 44. FIG. 47 is a top view of the atomizer housing of FIG. 44. FIG. 48 is a cross-section of the atomizer housing along the cut line shown in FIG. 47. Atomizer housing 132 is configured to fit within main shell 102. As can be seen in FIGS. 44-48, atomizer housing 132 comprises roughly two cylinders of different diameters. A chamfered surface 132-3 transitions from the smaller diameter of the distal end of atomizer housing 132 to a larger diameter at the proximal end of atomizer housing 132. The larger diameter at the proximal end of atomizer housing 132 is configured to be press fit into light pipe sleeve 140. The cylinder at the distal end terminates with a spade shaped tip 132-2. This spade shaped tip 132-2 may break a seal on cartridge 150 to allow the substance to be vaporized to come in direct contact with distal wick 134. Other shaped tips are possible (e.g., needle or spear shaped).

Chamfered surface 132-3 has one or more holes 132-1. These holes allow air to pass, via suction, through atomizer housing 132 into distal wick 134. This suction may be supplied by the user of personal vaporizer 100 sucking or inhaling on mouthpiece cover 114 and/or mouthpiece 116. The air that is sucked into distal wick 134 enters distal wick 134 on or near the chamfered surface between the two cylinders of distal wick 134. The air that is sucked into distal wick 134 displaces some of the substance being vaporized that has been absorbed by distal wick 134 causing it to be atomized as it exits distal wick 134 into the air gap formed between distal wick 134 and proximal wick 136. The heating element disposed around proximal wick 136 may then vaporize at least some of the atomized substance. In an embodiment, one or more holes 132-1 may range in diameter between 0.02 and 0.0625 inches.

In an embodiment, placing holes 132-1 at the leading edge of the chamfered surface places a set volume of the substance to be vaporized in the path of incoming air. This incoming air has nowhere to go but through the large diameter (or "head") end of the distal end wick 134. When the air enters this area in distal end wick 134 it displaces the substance to be vaporized that is suspended in distal end wick 134 towards an air cavity between distal end wick 134 and proximal end wick 136. When the displaced substance to be vaporized reaches the surface of distal end wick 134, it is forced out of the wick by the incoming air and the negative pressure of the cavity. This produces an atomized cloud of the substance to be vaporized. In an embodiment, the diameter of the head of distal end wick 134 may be varied and be smaller than the diameter of the proximal end wick 136. This allows for a tuned volume of air to bypass proximal end wick 136 and directly enter the cavity between distal wick 134 and distal wick 136 without first passing through distal wick 136.

Figure 49:
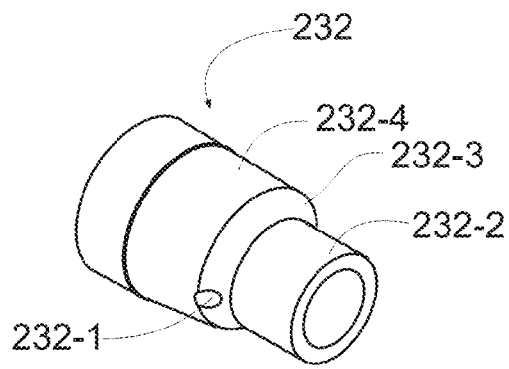
FIG. 49 is a perspective view of an atomizer housing of a personal vaporizer unit.
Figure 50:
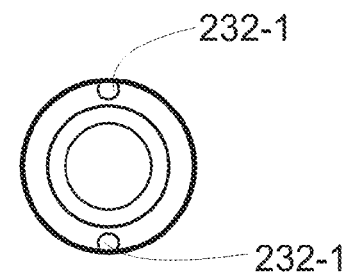
FIG. 50 is a distal end view of the atomizer housing of FIG. 49.
Figure 51:
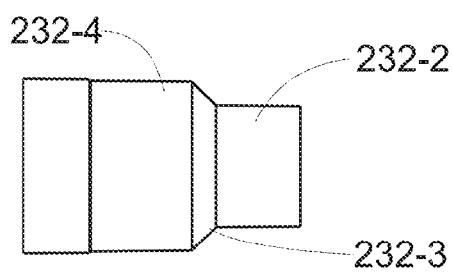
FIG. 51 is a side view of the atomizer housing of FIG. 49.
Figure 52:
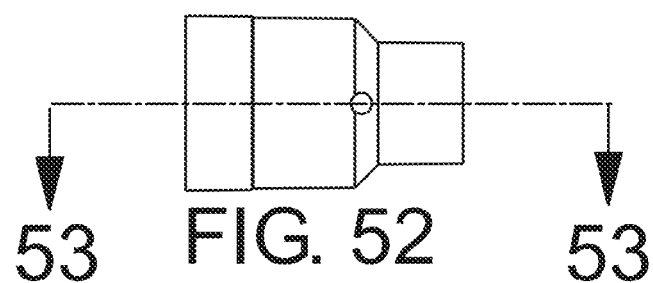
FIG. 52 is a top view of the atomizer housing of FIG. 49.
Figure 53:
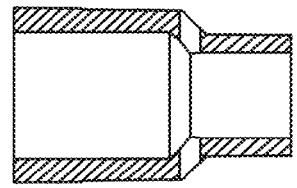
FIG. 53 is a cross-section of the atomizer housing along the cut line shown in FIG. 52.
Figure 59:
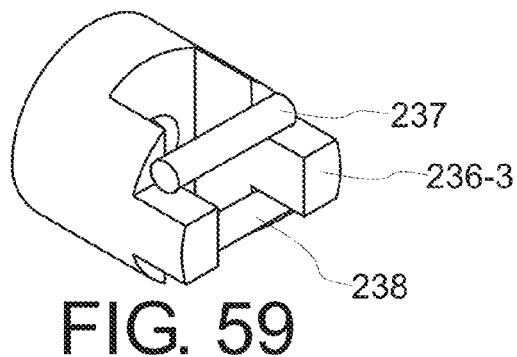
FIG. 59 is a perspective view of the proximal end wick and wire guides of FIGS. 54-58.
Figure 59A:
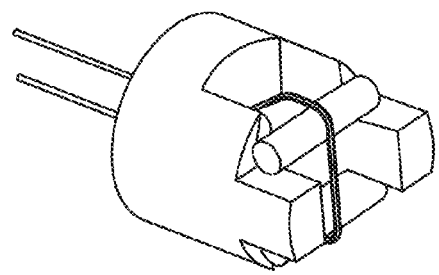
FIG. 59A is a perspective view showing a heating element disposed through the proximal end wick and around the wire guides of FIGS. 54-58.
Figure 59B:
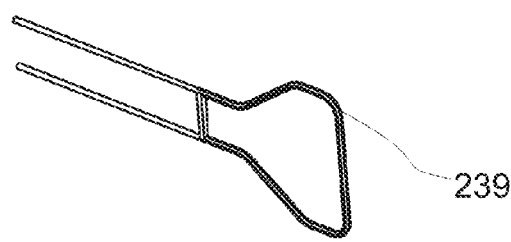
FIG. 59B is a perspective view of the heating element of a personal vaporizer unit.
Figure 60:
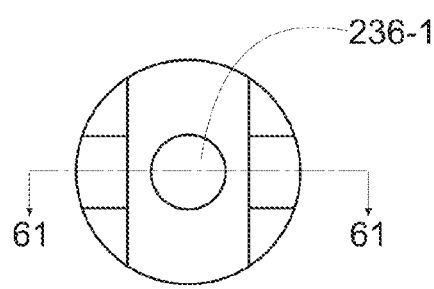
FIG. 60 is a distal end view of the wick element of FIGS. 54-58.
Figure 61:
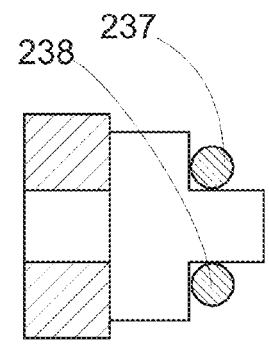
FIG. 61 is a cross-section of the wick element and wire guides along the cut line shown in FIG. 60.
Figure 62:
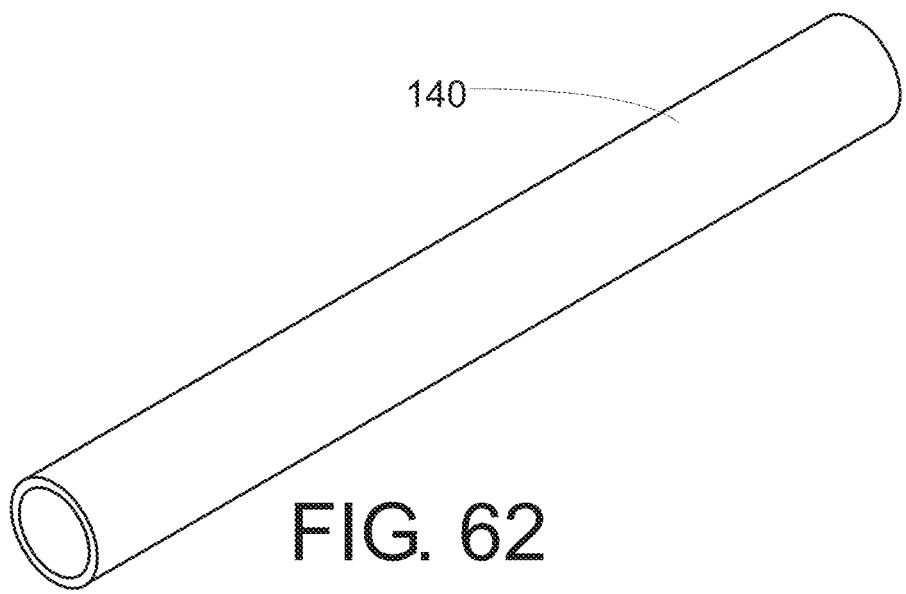
FIG. 62 is a perspective view of a light pipe sleeve of a personal vaporizer unit.
Figure 63:
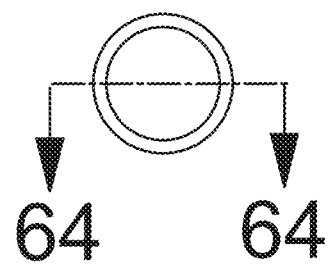
FIG. 63 is an end view of the light pipe sleeve of FIG. 62.
Figure 64:
FIG. 64 is a cross-section of the light pipe sleeve along the cut line shown in FIG. 63.

FIG. 49 is a perspective view of an atomizer housing of a personal vaporizer unit. FIG. 50 is a distal end view of the atomizer housing of FIG. 49. FIG. 51 is a side view of the atomizer housing of FIG. 49. FIG. 52 is a top view of the atomizer housing of FIG. 49. FIG. 53 is a cross-section of the atomizer housing along the cut line shown in FIG. 52. Atomizer housing 232 is an alternative embodiment, for use with proximal wick 234, to atomizer house 132. Atomizer housing 232 is configured to fit within main shell 102 and light pipe sleeve 140. As can be seen in FIGS. 49-53, atomizer housing 232 comprises roughly two cylinders of different diameters. A chamfered surface 232-3 transitions from the smaller diameter of the distal end of atomizer housing 232 to a larger diameter at the proximal end of atomizer housing 232. The larger diameter at the proximal end of atomizer housing 232 is configured to be press fit into light pipe sleeve 140. The cylinder at the distal end terminates with an open cylinder tip 232-2. This open cylinder tip 232-2 allows the pointed end 234-1 of proximal wick 234 to break a seal on cartridge 150 to allow the substance to be vaporized to come in direct contact with proximal wick 234.

Chamfered surface 232-3 has one or more holes 232-1. These holes allow air to pass, via suction, through atomizer housing 232 into proximal wick 234. The air that is sucked into proximal wick 234 enters proximal wick 234 on or near the chamfered surface between the two cylinders of proximal wick 234. The air that is sucked into proximal wick 234 displaces some of the substance being vaporized that has been absorbed by proximal wick 234 causing it to be atomized as it exits proximal wick 234 into the air gap formed between proximal wick 234 and proximal wick 136. The heating element disposed around proximal wick 136 may then vaporize at least some of the atomized substance being vaporized. In an embodiment, one or more holes 232-1 may range in diameter between 0.02 and 0.0625 inches.

In an embodiment, placing holes 232-1 at the leading edge of the chamfered surface places a set volume of the substance to be vaporized in the path of incoming air. This incoming air has nowhere to go but through the head of the distal end wick 234. When the air enters this area in distal end wick 234 it displaces the substance to be vaporized that is suspended in distal end wick 234 towards an air cavity between distal end wick 234 and proximal end wick 236. When the displaced substance to be vaporized reaches the surface of distal end wick 232, it is forced out of the wick by the incoming air and the negative pressure of the cavity. This produces an atomized cloud of the substance to be vaporized. In an embodiment, the diameter of the head of distal end wick 234 may be varied and be smaller than the diameter of the proximal end wick 236. This allows for a tuned volume of air to bypass distal wick 236 and directly enter the cavity between proximal wick 234 and distal wick 236 without first passing through distal wick 236.

FIG. 54 is a perspective view of an atomizer housing and wicks of a personal vaporizer unit. FIG. 55 is an exploded view of the atomizer housing, wire guides, and wicks of FIG. 54. FIG. 56 is a side view of the atomizer housing and wicks of FIG. 54. FIG. 57 is a distal end view of the atomizer housing and wicks of FIG. 54. FIG. 58 is a cross-section of the atomizer housing and wicks along the cut line shown in FIG. 57. The atomizer housing and wicks shown in FIGS. 54-58 is an alternative embodiment for use with proximal wick 236. The embodiment shown in FIGS. 54-58 use atomizer housing 232, proximal wick 234, proximal wick 236, wire guide 237, and wire guide 238. Proximal wick 236 is configured to fit within atomizer housing 232. As can be seen in FIGS. 54-58, proximal wick 236 includes internal wire passageway 236-1. This wire passageway 236-1 allows a conductor or a heating element (not shown) to be positioned through proximal wick 236 (via internal wire passageway 236-1). The conductor or heating element may be positioned around wire guide 237 and wire guide 238. Thus, a conductor or heating element may run the through wire passageway 236-1, around wire guides 237 and 238, and then back through wire passageway 236-1 to return to approximately its point of origin. The heating element may, when personal vaporizer unit 100 is activated, heat proximal wick 236 in order to facilitate vaporization of a substance.

FIG. 59 is a perspective view of the proximal end wick assembly of FIGS. 54-58. FIG. 59A is a perspective view showing a heating element disposed through the proximal end wick and around the wire guides of FIGS. 54-58. FIG. 59B is a perspective view of the heating element of a personal vaporizer unit. FIG. 60 is a distal end view of the wick element and wire guides of FIGS. 54-58. FIG. 61 is a cross-section of the wick element and wire guides along the cut line shown in FIG. 60. As can be seen in FIG. 59A, a conductor or heating element 239 may run through wire passageway 236-1, around wire guides 237 and 238, and then back through wire passageway 236-1 to return to approximately its point of origin.

In an embodiment, distal wicks 134, 234, and proximal wicks 136, 236, may be made of, or comprise, for example a porous ceramic. Distal wicks 134, 234, and proximal wicks 136, 236, may be made of, or comprise aluminum oxide, silicon carbide, magnesia partial stabilized zirconia, yttria tetragonal zirconia polycrystal, porous metal (e.g., steel, aluminum, platinum, titanium, and the like), ceramic coated porous metal, woven metal, spun metal, metal wool (e.g., steel wool), porous polymer, porous coated polymer, porous silica (i.e., glass), and/or porous Pyrex. Distal wicks 134, 234, and proximal wicks 136, 236, may be made of or comprise other materials that can absorb a substance to be vaporized.

The conductor or heating element that is disposed through proximal wick 136 or 236 may be made of, or comprise, for example: nickel chromium, iron chromium aluminum, stainless steel, gold, platinum, tungsten molybdenum, or a piezoelectric material. The conductor or heating element that is disposed through proximal wick 136 can be made of, or comprise, other materials that become heated when an electrical current is passed through them.

FIG. 62 is a perspective view of a light pipe sleeve of a personal vaporizer unit. FIG. 63 is an end view of the light pipe sleeve of FIG. 62. FIG. 64 is a cross-section of the light pipe sleeve along the cut line shown in FIG. 63. Light pipe sleeve 140 is configured to be disposed within main shell 102. Light pipe sleeve 140 is also configured to hold cartridge 150 and atomizer housing 132 or 232. As discussed previously, light pipe sleeve 140 is configured to conduct light entering the proximal end of light pipe sleeve 140 (e.g., from LEDs 125-127) to the distal end of light pipe sleeve 140. Typically, the light exiting the distal end of light pipe sleeve 140 will be visible from the exterior of personal vaporizer 100. The light exiting the distal end of light pipe sleeve 140 may be diffused by cartridge 150. The light exiting the distal end of light pipe sleeve 140 may illuminate characters and/or symbols drawn, printed, written, or embossed, etc., in an end of cartridge 150. In an embodiment, light exiting light pipe sleeve 140 may illuminate a logo, characters and/or symbols cut through outer main shell 102. In an embodiment, light pipe sleeve 140 is made of, or comprises, a translucent acrylic plastic.

FIG. 65 is a perspective view of a cartridge of a personal vaporizer unit. FIG. 66 is a proximal end view of the cartridge of FIG. 65. FIG. 67 is a side view of the cartridge of FIG. 65. FIG. 68 is a top view of the cartridge of FIG. 65. FIG. 69 is a cross-section of the cartridge along the cut line shown in FIG. 66. As shown in FIGS. 65-69, cartridge 150 comprises a hollow cylinder section with at least one exterior flat surface 158. The flat surface 158 forms, when cartridge 150 is inserted into the distal end of personal vaporizer unit 100, an open space between the exterior surface of the cartridge and an interior surface of light pipe sleeve 140. This space defines a passage for air to be drawn from outside personal vaporizer unit 100, through personal vaporizer unit 100 to be inhaled by the user along with the vaporized substance. This space also helps define the volume of air drawn into personal vaporizer unit 100. By defining the volume of air typically drawn into the unit, different mixtures of vaporized substance to air may be produced.

The hollow portion of cartridge 150 is configured as a reservoir to hold the substance to be vaporized by personal vaporizer unit 100. The hollow portion of cartridge 150 holds the substance to be vaporized in direct contact with distal wick 134 or 234. This allows distal wick 134 or 234 to become saturated with the substance to be vaporized. The area of distal wick 134 or 234 that is in direct contact with the substance to be vaporized may be varied in order to deliver different doses of the substance to be vaporized. For example, cartridges 150 with differing diameter hollow portions may be used to deliver different doses of the substance to be vaporized to the user.

Cartridge 150 may be configured to confine the substance to be vaporized by a cap or seal (not shown) on the proximal end. This cap or seal may be punctured by the end of atomizer housing 132, or the pointed end 234-1 of proximal wick 234.

When inserted into personal vaporizer unit 100, cartridge standoffs 157 define an air passage between the end of light pipe sleeve 140 and main shell 102. This air passage allows air to reach the air passage defined by flat surface 158.

The hollow portion of cartridge 150 also includes one or more channels 154. The end of these channels are exposed to air received via the air passage(s) defined by flat surface 158. These channels allow air to enter the hollow portion of cartridge 150 as the substance contained in cartridge 150 is drawn into a distal wick 134 or 234. Allowing air to enter the hollow portion of cartridge 150 as the substance contained in cartridge 150 is removed prevents a vacuum from forming inside cartridge 150. This vacuum could prevent the substance contained in cartridge 150 from being absorbed into distal wick 134 or 234.

In an embodiment, cartridge 150 may be at least partly translucent. Thus cartridge 150 may act as a light diffuser so that light emitted by one or more of LEDs 125-127 is visible external to personal vaporizer unit 100.

Figure 70:
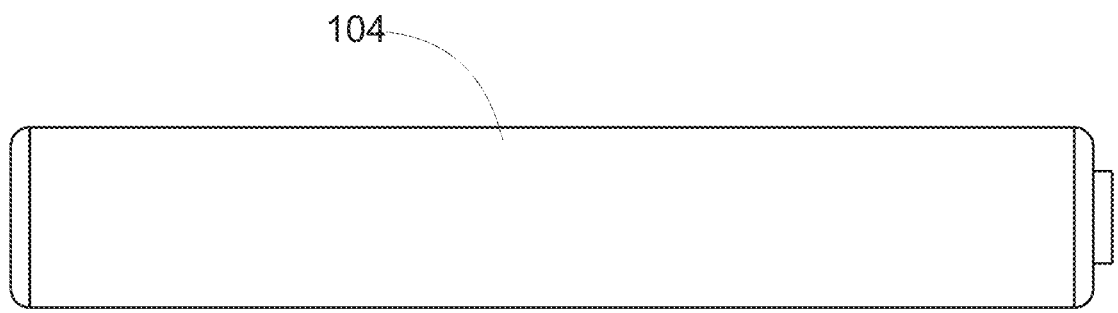
FIG. 70 is a side view of a battery of a personal vaporizer unit.
Figure 71:
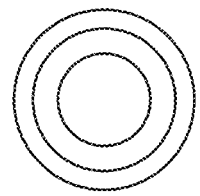
FIG. 71 is an end view of the battery of FIG. 70.
Figure 72:
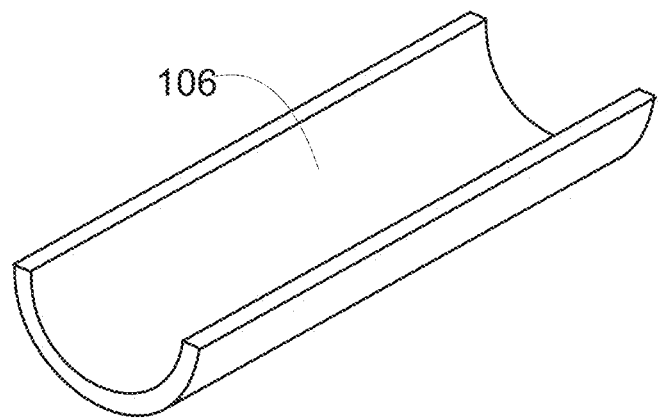
FIG. 72 is a perspective view of a battery support of a personal vaporizer unit.

FIG. 70 is a side view of a battery of a personal vaporizer unit. FIG. 71 is an end view of the battery of FIG. 70. FIG. 72 is a perspective view of a battery support of a personal vaporizer unit. As can be seen in FIG. 72, battery support 106 does not form a complete cylinder that completely surrounds battery 104. This missing portion of a cylinder forms a passageway that allows air and the vaporized substance to pass by the battery from the atomizer assembly to the mouthpiece 116 so that it may be inhaled by the user.

Figure 73:
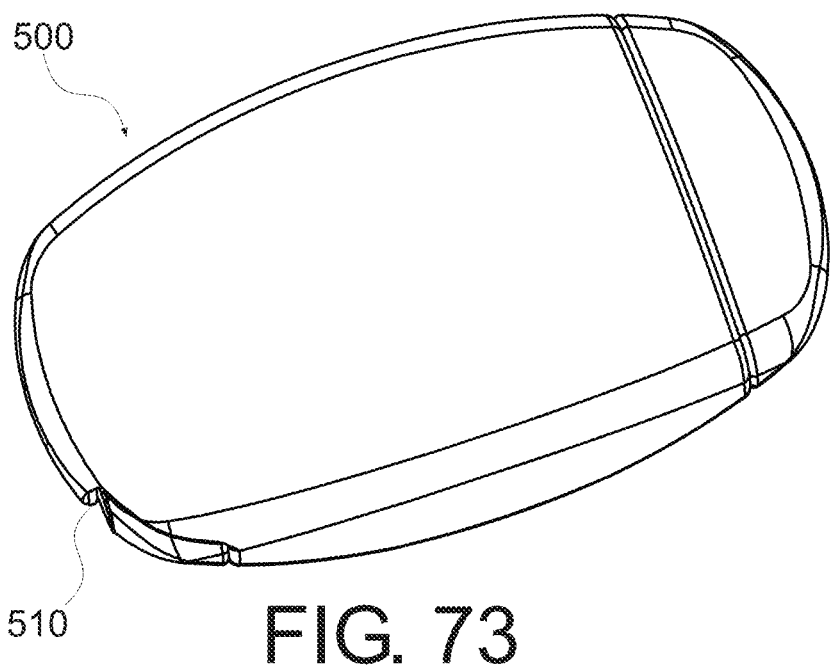
FIG. 73 is a perspective view of a personal vaporizer unit case.
Figure 74:
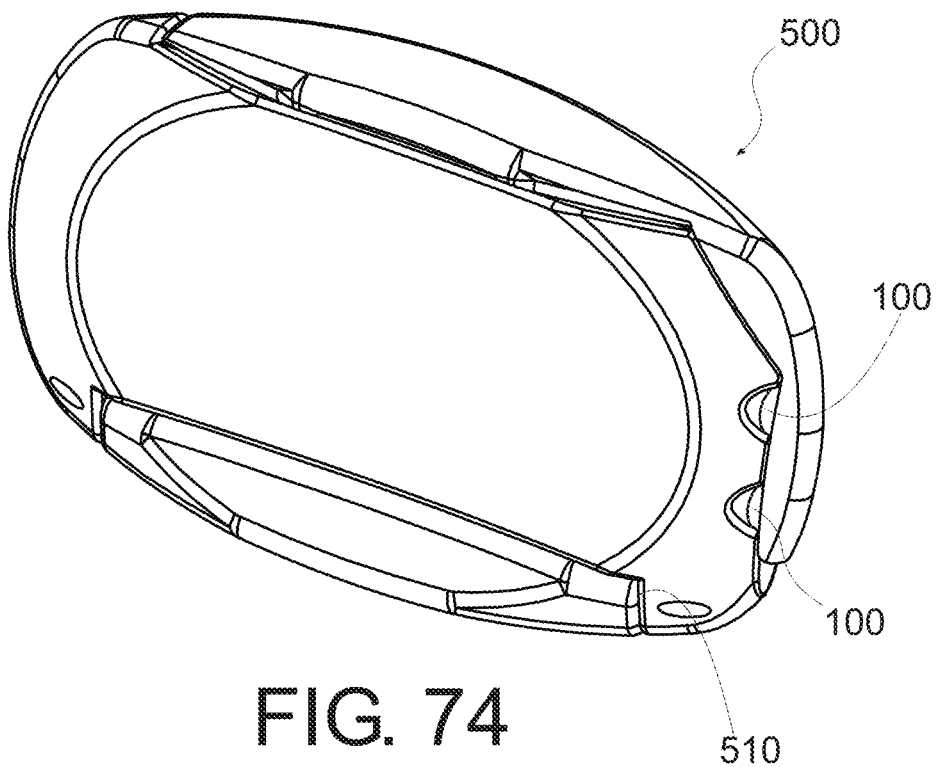
FIG. 74 is a perspective view of a personal vaporizer unit case.

FIG. 73 is a top perspective view of a personal vaporizer unit case. FIG. 74 is a bottom perspective view of a personal vaporizer unit case. Personal vaporizer case 500 is configured to hold one or more personal vaporizer units 100. Personal vaporizer case 500 includes a connector 510 to interface to a computer. This connector allows case 500 to transfer data from personal vaporizer unit 100 to a computer via connecter 510. Case 500 may also transfer data from personal vaporizer unit 100 via a wireless interface. This wireless interface may comprise an infrared (IR) transmitter, a Bluetooth interface, an 802.11 specified interface, and/or communicate with a cellular telephone network. Data from a personal vaporizer unit 100 may be associated with an identification number stored by personal vaporizer unit 100. Data from personal vaporizer unit 100 may be transmitted via the wireless interface in association with the identification number.

Personal vaporizer case 500 includes a battery that may hold charge that is used to recharge a personal vaporizer unit 100. Recharging of personal vaporizer unit 100 may be managed by a charge controller that is part of case 500.

When case 500 is holding a personal vaporizer unit 100, at least a portion of the personal vaporizer unit 100 is visible from the outside of case 500 to allow a light emitted by personal vaporizer unit 100 to provide a visual indication of a state of personal vaporizer unit 500. This visual indication is visible outside of case 500.

Personal vaporizer unit 100 is activated by a change in impedance between two conductive surfaces. In an embodiment, these two conductive surfaces are part of main shell 102 and mouthpiece 116. These two conductive surfaces may also be used by case 500 to charge battery 104. These two conductive surfaces may also be used by case 500 to read data out of personal vaporizer unit 100.

In an embodiment, when a user puts personal vaporizer unit 100 in his/her mouth and provides "suction," air is drawn into personal vaporizer unit 100 though a gap between the end of main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 132, cartridge 150, and light pipe sleeve 140. Air travels to distal wick 134 via one or more holes 132-1, in chamfered surface(s) 132-3. Air travels to distal wick 234 via one or more holes 232-1, in chamfered surface(s) 232-3. Air is also allowed to enter cartridge 150 via one or more channels 154. This air entering cartridge 150 via channels 154 "back fills" for the substance being vaporized which enters distal wick 134. The substance being vaporized is held in direct contact with distal wick 134 or 234 by cartridge 150. The substance being vaporized is absorbed by and may saturate distal wick 134 or 234 and proximal wick 136 or 236.

The incoming air drawn through holes 132-1 displaces from saturated distal wick 134 the substance being vaporized. The displaced substance being vaporized is pulled from wick elements 134 into a cavity between distal wick 134 and 136. This cavity may also contain a heating element that has been heated to between 150-200° C. The displaced substance being vaporized is pulled from wick elements 134 in small (e.g., atomized) droplets. These atomized droplets are vaporized by the heating element.

In an embodiment, when a user puts personal vaporizer unit 100 in his/her mouth and provides "suction," air is drawn into personal vaporizer unit 100 though a gap between the end of main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 232, cartridge 150, and light pipe sleeve 140. Air travels to proximal wick 234 via one or more holes 232-1, in chamfered surface(s) 232-1. Air is also allowed to enter cartridge 150 via one or more channels 154. This air entering cartridge 150 via channels 154 "back fills" for the substance being vaporized which enters proximal wick 234. The substance being vaporized is held in direct contact with proximal wick 234 by cartridge 150. The substance being vaporized is absorbed by and may saturate distal wick 243 and proximal wick 236.

The incoming air drawn through holes 232-1 displaces from saturated proximal wick 234 the substance being vaporized. The displaced substance being vaporized is pulled from wick elements 234 into a cavity between wick distal wick 234 and proximal wick 236. This cavity may also contain a heating element that has been heated to between 150-200° C. The displaced substance being vaporized is pulled from distal wick 234 in small (e.g., atomized) droplets. These atomized droplets are vaporized by the heating element.

In both of the previous two embodiments, the vaporized substance and air are drawn down a galley adjacent to battery 104, through mouthpiece insulator 112, mouthpiece 116, and mouthpiece cover 114. After exiting personal vaporizer unit 100, the vapors may be inhaled by a user.

Figure 76:
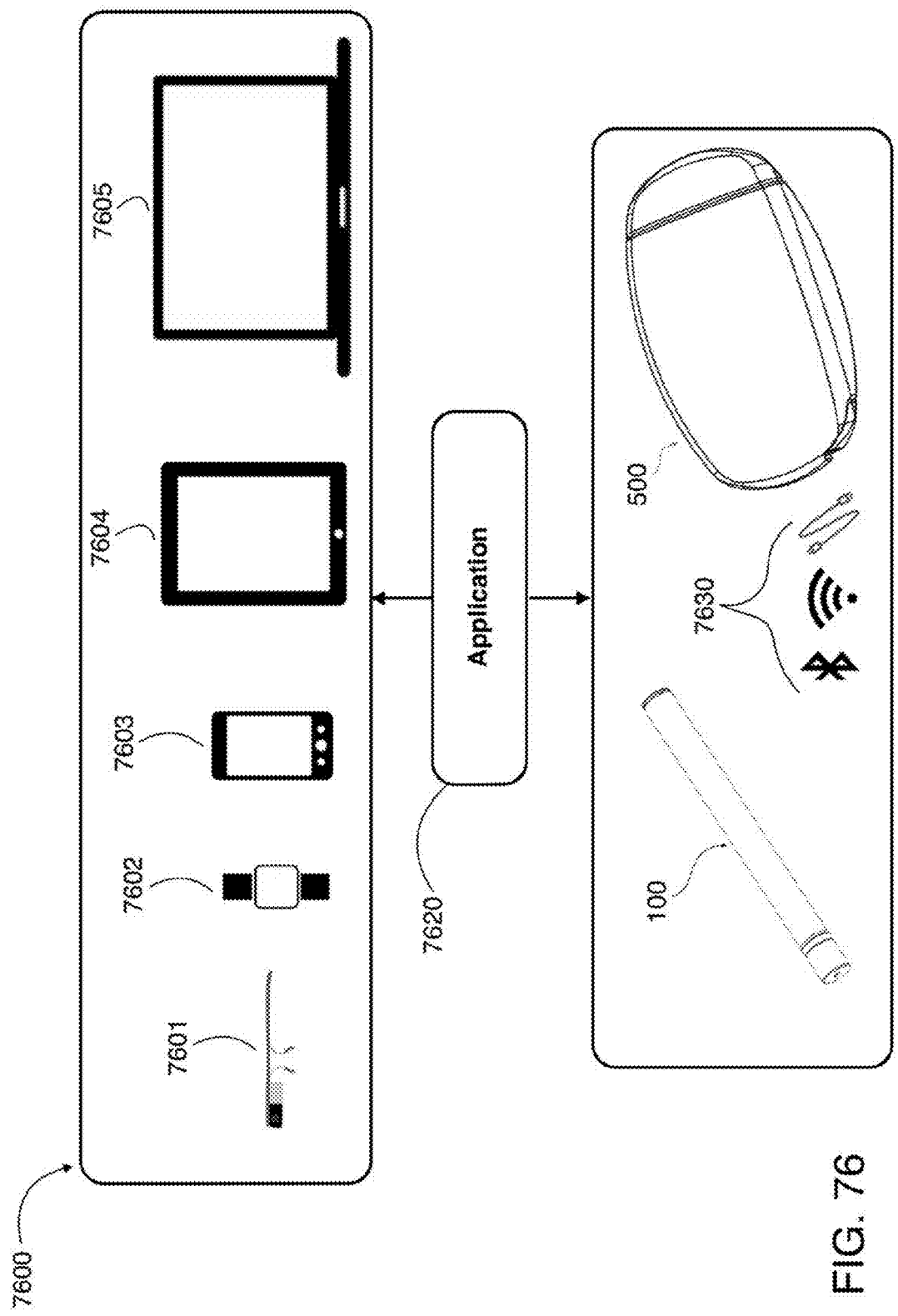
FIG. 76 illustrates a system including a personal vaporizer unit.

FIG. 76 illustrates a system including a personal vaporizer unit. In FIG. 76, system 7600 includes at least one personal digital device 7610, a personal vaporizer unit (PVU) 100, case 500, and an associated application 7620. Examples of personal digital devices 7610 are illustrated in FIG. 76 as wearable devices 7601, smart watch 7602, smart phone 7603, tablet computer 7604, and computer 7605. Application 7620 is operatively coupled to interface PVU 100 and/or case 500 with a personal digital device 7610. PVU 100 and/or case 500 may be operatively coupled to a personal digital device 7610 using wireless and/or wired communication 7630. PVU 100 and/or case 500 may be operatively coupled to each other using wireless and/or wired communication 7630.

A personal digital device 7610 is capable of sharing data with PVU 100 and/or case 500 through both wired methods such as data cables, or through wireless methods such as WiFi, Bluetooth, cellular networks, IR or similar technologies. Personal digital devices 7610 may use software (collectively or commonly referred to as applications or "apps") that provide a graphical user interface (GUI)—e.g., application 7620. A GUI may provide a convenient way for the user to interact with application 7620. Application 7620 may facilitate the transferring of data from PVU 100 and/or case 500 to the personal digital device 7610. Application 7620 may facilitate the transferring of data to PVU 100 and/or case 500 from the personal digital device 7610.

Figure 77:
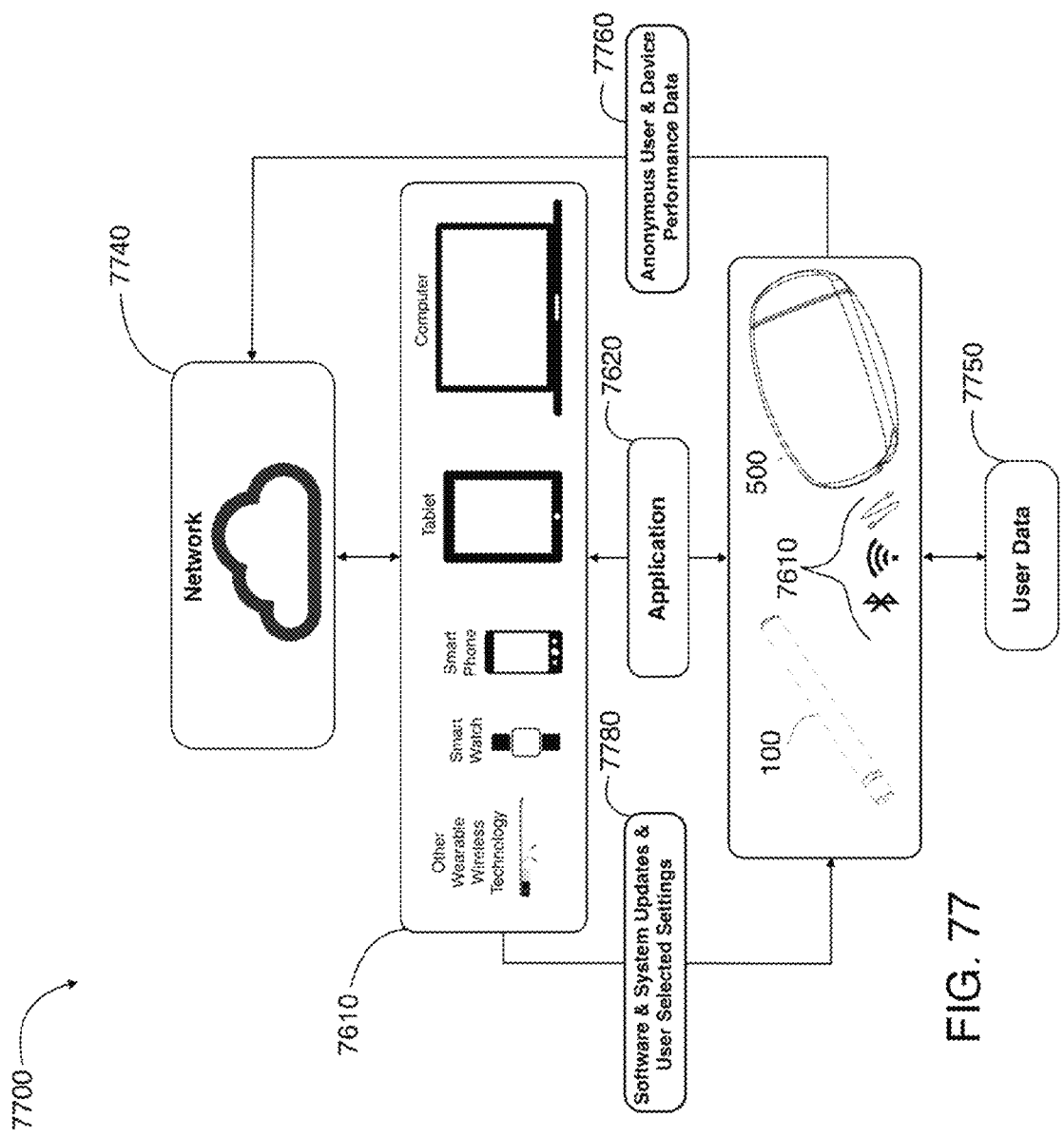
FIG. 77 is an illustration of data flows in a system including a personal vaporizer unit.

FIG. 77 is an illustration of data flows in a system including a personal vaporizer unit. In FIG. 76, system 7700 includes at least one personal digital device 7610, a personal vaporizer unit (PVU) 100, case 500, an associated application 7620, network 7740, and user data 7750. Examples of personal digital devices 7610 are illustrated in FIG. 77 as wearable devices 7601, smart watch 7602, smart phone 7603, tablet computer 7604, and computer 7605. Application 7620 is operatively coupled to interface PVU 100 and/or case 500 with a personal digital device 7610. PVU 100 and/or case 500 may be operatively coupled to a personal digital device 7610 using wireless and/or wired communication 7630. PVU 100 and/or case 500 may be operatively coupled to a personal digital device 7610 using wireless and/or wired communication 7630 via network 7740. User data 7750 may be operatively coupled to a personal digital device 7610 using wireless and/or wired communication 7630 via PVU 100 and/or case 500 and network 7740. PVU 100 and/or case 500 may be operatively coupled to each other using wireless and/or wired communication 7630.

In an embodiment, of PVU 100 and/or case 500 may interact in a network directly by using of onboard wired and wireless data transmitting methods. PVU 100 and/or case 500 may interact in a network indirectly through the use of wired and wireless connection methods that interfacing via an application 7620 running on a personal digital device 7610. Some data (e.g., anonymous user and device performance data 7760) may be shared directly to network 7740 without the use of personal digital device 7610. Some data may be shared with to network 7740 through application 7620 running on a personal digital device 7610. The types of data shared directly both in relation to data transmitted and data received depends on the configuration of PVU 100, case 500, and/or application 7620. Personal digital device 7610 may not be required for the transmission of data to network 7740 or receipt of data from network 7740 (e.g., software and system updates, user selected settings 7780). Personal digital device 7610 can provide a desirable and common platform (e.g., GUI) for interfacing with the end user.

Figure 78:
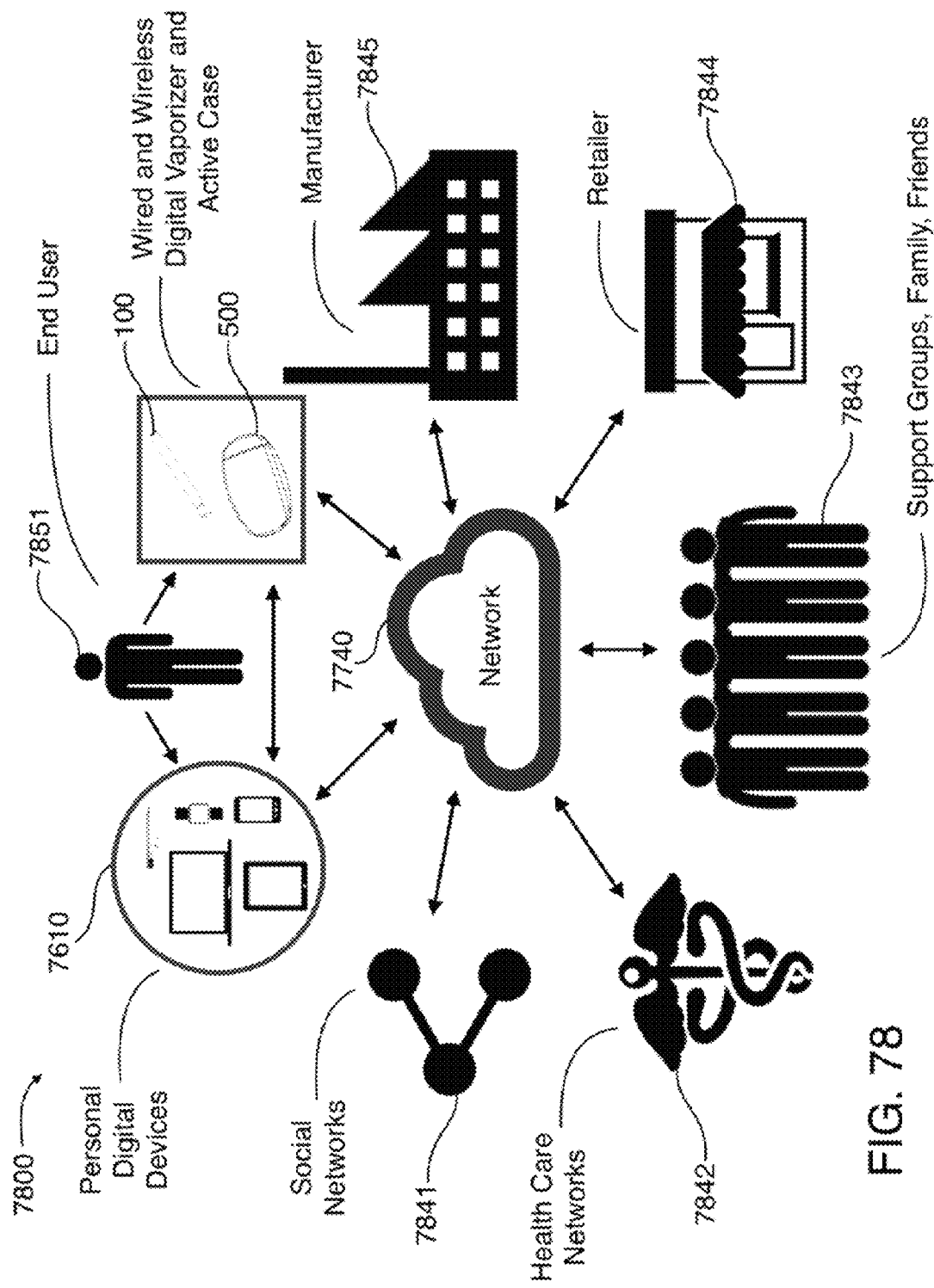
FIG. 78 is an illustration of networks interfacing with a personal vaporizer unit.

FIG. 78 is an illustration of networks interfacing with a personal vaporizer unit. In FIG. 8, system 7800 comprises PVU 100, case 500, network 7740, end user 7851, personal digital device 7610, social network 7841, health care network 7842, social/support group 7843, retailer 7844, and manufacturer 7845. Each of social network 7841, health care network 7842, social/support group 7843, retailer 7844, and manufacturer 7845 can be operatively coupled to PVU 100 and/or case 500. Each of social network 7841, health care network 7842, social/support group 7843, retailer 7844, and manufacturer 7845 can be operatively coupled to PVU 100 and/or case 500 via network 7740. PVU 100 and/or case 500 can be operatively coupled to personal digital device 7610 (or each other) without using network 7740. PVU 100 and/or case 500 can be operatively coupled to personal digital device 7610 (or each other) via network 7740.

In an embodiment, some PVU 100 and/or case 500 data can be sent and received directly to and from network 7740. Some PVU 100 and/or case 500 data can be sent and received directly to and from network 7740 for further communication with social network 7841, health care network 7842, social/support group 7843, retailer 7844, and/or manufacturer 7845. Some data can be shared with the end user's personal digital device 7610 through the use of an application (e.g., application 7620) and then subsequently shared with via network 7740. The end users personal digital device 7610 can also be used to receive data from social network 7841, health care network 7842, social/support group 7843, retailer 7844, and/or manufacturer 7845. This data may be further shared with PVU 100 and/or case 500. Different entities may contribute to network 7740 data flow including end user 7851, PVU 100 and/or case 500, personal digital device 7610, social network 7841, health care network 7842, social/support group 7843, retailer 7844, and/or manufacturer 7845, and others, may each contribute to data that is shared in system 7800.

Figure 79:
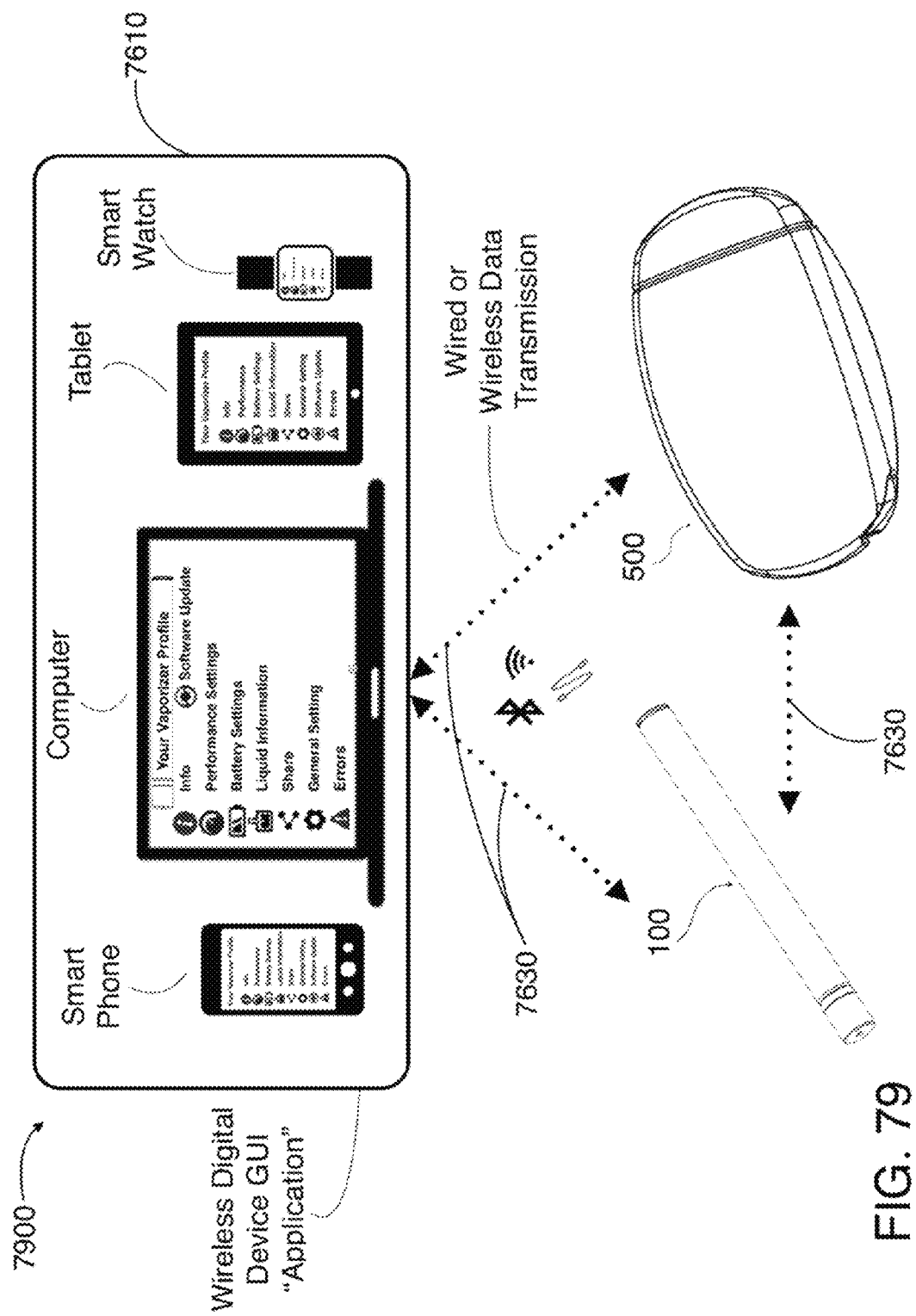
FIG. 79 is an illustration of a data communication system.

FIG. 79 is an illustration of a data communication system. In FIG. 79, communication system 7900 includes personal digital device 7610, PVU 100, and case 500. PVU 100 may be operatively coupled to personal digital device 7610 using wireless and/or wired communication 7630. Case 500 may be operatively coupled to personal digital device 7610 using wireless and/or wired communication 7630. PVU 100 may be operatively coupled to case 500 using wireless and/or wired communication 7630.

In an embodiment, an application (e.g., application 7620) running on personal digital device 7610 provides an interface for the end user to engage and interact with functions related to communication of data to and from PVU 100 and/or case 500. In an embodiment, a user can control some aspects of the data transmission and data receiving to and from PVU 100 and/or case 500. Some data can be communicated as a background operation such that the end user does not have to initiate or authorize the data communication process.

Background processes of data communication can occur whenever a respective PVU 100 and/or case 500 is operatively coupled to the end users personal digital device 7610 (either through wireless or wired methods.) Various icons and text elements may inform the user of various ways that PVU 100 and/or case 500 settings can be adjusted or configured by the user. Various icons and text elements can provide a means for the user to see information about PVU 100 and/or case 500—such as battery information and similar device status. Various icons and text elements can provide a means for the user to update PVU 100 and/or case 500 internal software (a.k.a., firmware). Various icons and text elements can provide a means for the user to set security and/or authorization features of PVU 100 and/or case 500— such as setting a PIN code to activate the device or the use of personal biometric information as a means of authentication. Various icons and text elements can provide a means to configure foreground data sharing and related settings.

Figure 80:
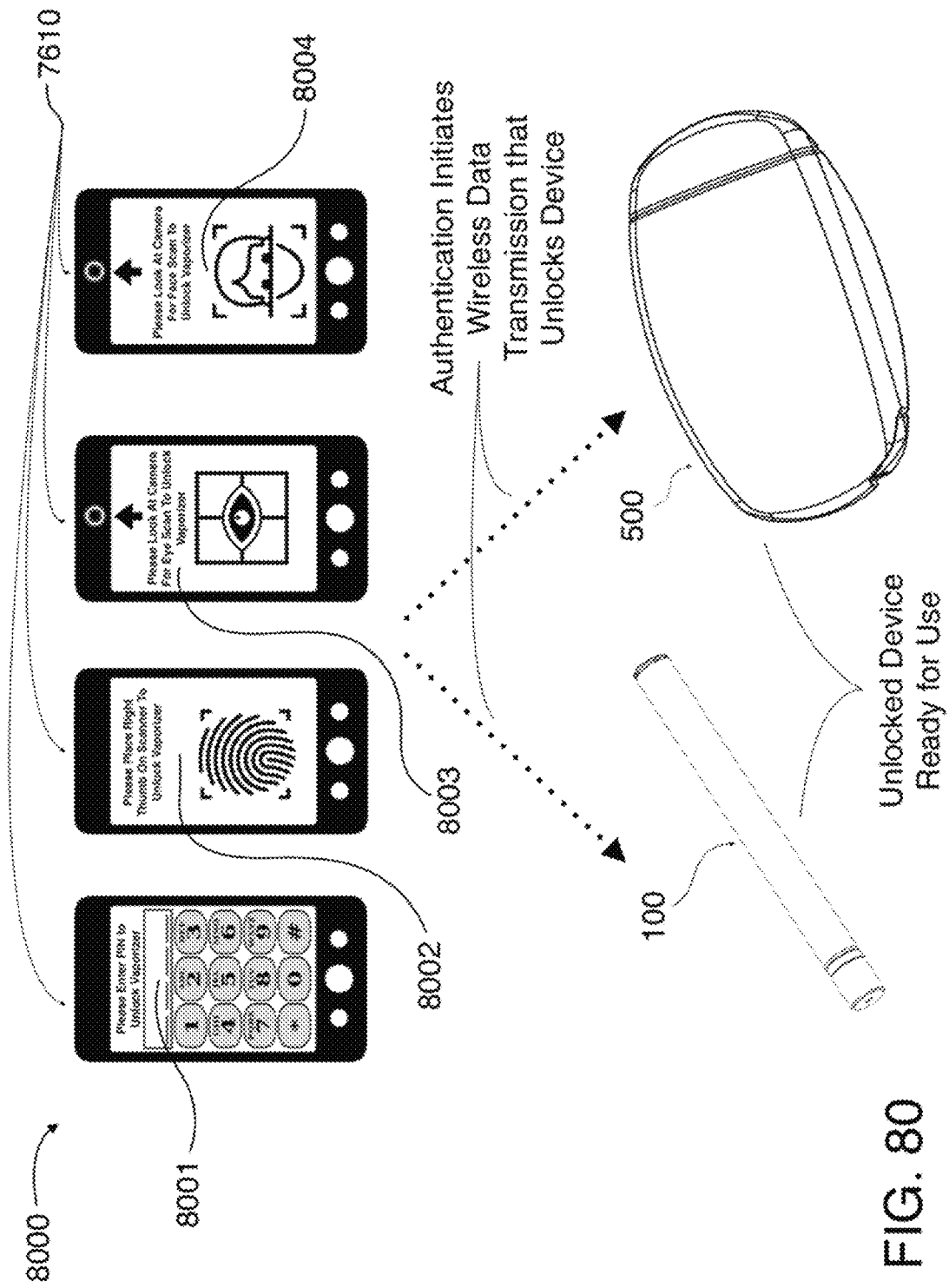
FIG. 80 illustrates a personal vaporizer authorization system.

FIG. 80 illustrates a personal vaporizer authorization system. In FIG. 80, authorization system includes personal digital device 7610, PVU 100, and case 500. Personal digital device 7610 can be operatively coupled to PVU 100. Personal digital device 7610 can be operatively coupled to case 500. Personal digital device 7610 is illustrated running authentication software. This authentication software may include, for example, PIN based authentication 8001, fingerprint based authentication 8002, iris scan based authentication 8003, and facial recognition based authentication 8004. When authentication software 8001-8003 determines the criteria for authorization have been met (e.g., correct PIN input, matched fingerprint, etc.), the authorization software can control personal digital device 7610 to send a wireless data transmission that unlocks PVU 100 and/or case 500.

The authentication process can be embodied as a feature of an application (e.g., application 7620) that is installed and running on personal digital device 7610. In FIG. 80, personal digital device 7610 is illustrated as a smart phone. However, it should be understood that personal digital device 7610 may be digital devices not illustrated in FIG. 80. Personal digital device 7610 has the capability of communicating data through the use of wired or wireless methods and has an operating system capable of running application(s).

In an embodiment, PVU 100 and/or case 500 may be rendered inactive after a period of inactivity. This is similar to a computer going into "sleep mode" when there is no usage detected for a predetermined and preset period of time. In order for PVU 100 and/or case 500 to be activated, and thereby be capable of being used by the user for the purpose of generating vapor, the user must be authenticated to insure that the device is being utilized by the intended end user, and to prevent unauthorized use, or accidental, or unintended activation of the device, or use of the device by an individual not of legal age to ingest the active component—such as nicotine. PIN based authentication 8001 process uses a user selected PIN code to authenticate the end use. Fingerprint based authentication 8002 process the user fingerprint to authenticate the end user. Iris scan based authentication 8003 process uses an eye or iris scan, or the like, to authenticate the end user. Facial recognition based authentication 8004 uses a face scan or image processing algorithm to authenticate the end user. Iris scan based authentication 8003 and facial recognition based authentication 8004 are easier to use if the user's personal digital device has a forward facing (on the same surface as the primary touch screen interface or similar) camera.

Figure 81:
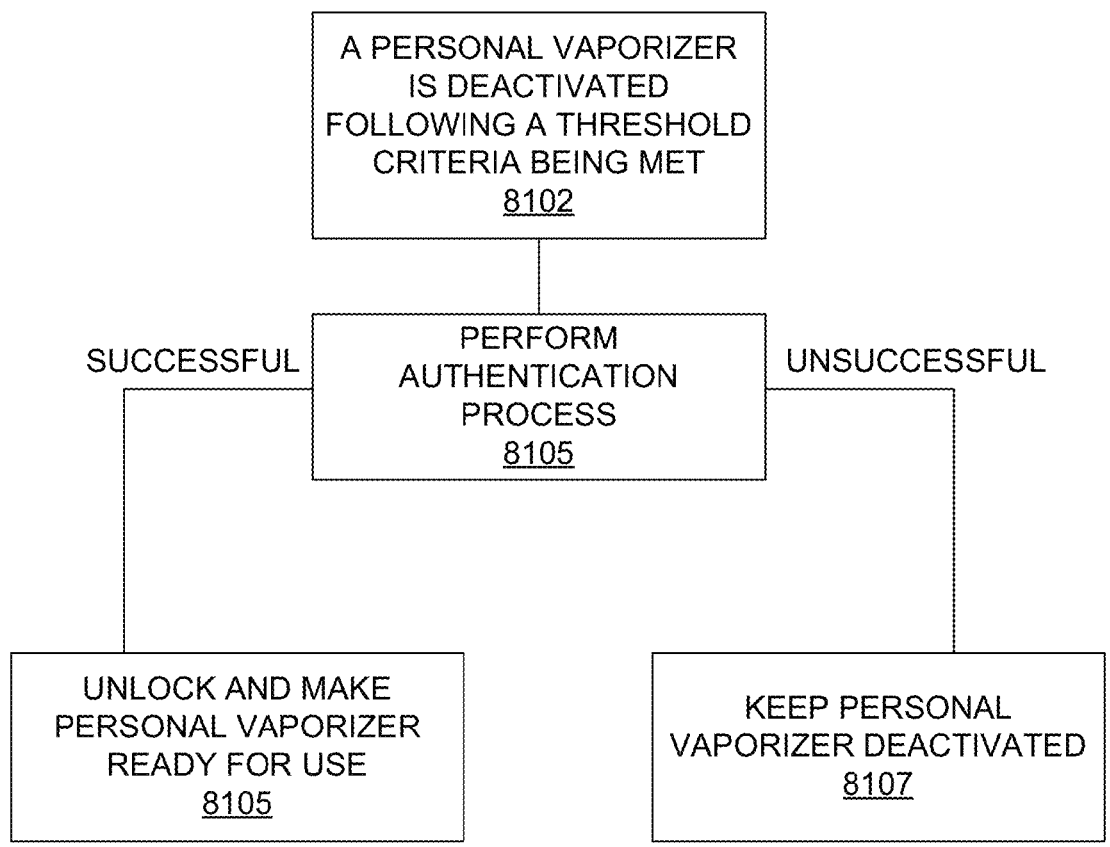
FIG. 81 is a flowchart illustrating a method of activating a personal vaporizer.

FIG. 81 is a flowchart illustrating a method of activating a personal vaporizer. The steps illustrated in FIG. 81 may be performed by one or more elements of system 7600, system 7700, system 7800, communication system 7900, and/or authorization system 8000. A personal vaporizer is deactivated following a threshold criteria being met (8102). For example, PVU 100 and/or case 500 may be rendered inactive after a period of inactivity. The period of inactivity may be preset. The period of inactivity may be a configurable parameter of PVU 100 and/or case 500. A user activated an authentication application on a personal digital wireless device (8103). For example, a user may run application 7620 on personal digital device 7610. Application 7620 may include functionality to unlock or activate PVU 100 and/or case 500. Application 7620 may include functionality to unlock or activate PVU 100 and/or case 500 using PIN based authentication 8001, fingerprint based authentication 8002, iris scan based authentication 8003, and/or facial recognition based authentication 8004.

An authentication process is performed (8105). If the authentication process is unsuccessful the personal vaporizer remains deactivated (8106). If the authentication process is successful the personal vaporizer is unlocked and made ready for use (8107).

In an embodiment, personal vaporizer unit 100 (and circuitry on PC-board 123, in particular) may perform onboard data gathering, data analysis, and/or the data transmission methods described herein. PVU 100 may interface with digital consumer technology products such as smart phones, tablet computers, lap top/netbook/desktop computers, wearable wireless technologies such as "smart watches," and other wearable technology such as Google "Glass," or similar through the use of programming, software, firmware, GUI, wireless communication, wired communication, and/or software commonly referred to as application(s) or "apps." Likewise, in an embodiment, case 500 may perform data gathering, data analysis, and/or the data transmission methods described herein. Case 500 may interface with digital consumer technology products such as smart phones, tablet computers, lap top/netbook/desktop computers, wearable wireless technologies such as "smart watches," and other wearable technology such as Google "Glass," or similar through the use of programming, software, firmware, GUI, wireless communication, wired communication, and/or software running on these devices (commonly referred to as application(s) or "apps.")

Wired means can be used to interface PVU 100 and/or case 500 to digital consumer technology products for the purpose of the transmission and exchange of data to/from PVU 100 or case 500 from/to the digital consumer technology products (and thereby also interfacing with apps running on the digital consumer technology products.) Wireless means can be used to interface PVU 100 and/or case 500 to digital consumer technology products for the purpose of the transmission and exchange of data to/from PVU 100 or case 500 from/to the digital a wireless interface. PVU 100 and/or case 500 may use a wireless means/interface that includes one or more of an infrared (IR) transmitter, a Bluetooth interface, an 802.11 specified interface, and/or communications with a cellular telephone network in order to communicate with consumer technology products (and thereby also interfacing with apps running on the digital consumer technology products.).

In an embodiment, PVU 100 and/or case 500 can interface (i.e., communicate) with digital consumer technology products and with apps as a way of relaying information and data to add additional functionality to PVU 100. This additional functionality may include (but is not limited to): (a) setting and/or specifying a desired number of activations cycles over a period of time; (b) setting and/or specifying reminders, alarms, or similar to notify the user; (c) setting and/or specifying a desired dose(s) for delivery of active substance(s) per inhalation; (d) setting and/or specifying a desired total delivered dose active substance(s) over a period of time—such as a total daily dose; (e) setting and/or specifying power settings of PVU 100 to modulate the vapor and/or aerosol strength, vapor and/or aerosol density, vapor and/or aerosol volume, vapor and/or aerosol flavor, vapor and/or aerosol temperature, and/or similar vapor and aerosol characteristics of the vapor or aerosol generated by the PVU 100; (f) setting and/or specifying power settings of PVU 100 to modulate, adjust, configure or similar the settings of the device as they relate to battery life and/or performance; (g) setting and/or specifying configurations of PVU 100 related to the liquid components and formulation; (h) setting and/or specifying ambient temperature based environmental configurations; (i) setting and/or specifying humidity based environmental configurations; (j) setting and/or specifying altitude based environmental configurations; (k) setting and/or specifying temporal (i.e., time) based configurations; (l) setting and/or specifying parameters to minimize, maximize, and or modulate the functional effects of the taste and/or flavor component of the vapor product; (m) setting and/or specifying functional effect parameters to minimize or maximize the functional effects related to pharmacodynamics and pharmacokinetics of an active ingredient or drug component of the vapor or aerosol product; (n) receiving and/or providing to a user, PVU 100 and/or case 500 alerts and notifications; (o) receiving and/or providing to a user, PVU 100 alerts and notifications related to recharging (e.g., whether a battery 104 needs to be recharged); (p) receiving and/or providing to a user, case 500 alerts and notifications related to recharging; (q) receiving and/or providing to a user, PVU 100 alerts and notifications related to charge status (e.g., whether a battery 104 is fully or partially charged); (r) receiving and/or providing to a user, case 500 alerts and notifications related to charge status; (s) receiving and/or providing to a user, PVU 100 alerts and notifications related to liquid cartridge usage status—such as a number of usages or inhalations taken from a cartridge; (t) receiving and/or providing to a user, PVU 100 alerts and notifications related to liquid cartridge remaining status—such as a number of usages or inhalations remaining in a cartridge; (u) receiving and/or providing to a user, PVU 100 alerts and notifications related to time-based liquid cartridge usage status—such as number of usages or inhalations taken over a preset or predetermined period of time, for example number of usages or inhalations taken per day; (v) receiving and/or providing to a user, PVU 100 alerts and notifications related to liquid cartridge contents—such as active component(s), strength, dosage (or similar), flavor profile (or similar), and general formulation (or similar); (w) receiving and/or providing to a user, PVU 100 alerts and notifications related to liquid cartridge, liquid cartridge assembly, or similar, requiring replacement; (x) receiving and/or providing to a user, PVU 100 alerts and notifications related to preset times for usage of PVU 100; and, (y) receiving and/or providing to a user, PVU 100 heating element alerts and notifications status or "health"—such as number of cycles performed, and/or number of cycles remaining before suggested and/or required replacement of a heating element or heating element assembly.

In an embodiment, the power settings of PVU 100 may be set and/or specified to modulate or configure the activation energy delivered to the heating element(s) as well as modulating or configuring the parameters of the heating element(s) being energized in relation to the time to peak activation or "warm up" or "ramp" and or the time of maximum or peak activation, and or the time of the heating element being deactivated or the "cool down" to effect and modulate vapor and/or aerosol strength, vapor and/or aerosol density, vapor and/or aerosol volume, vapor and/or aerosol flavor, vapor and/or aerosol temperature, and/or similar vapor and aerosol characteristics of the vapor or aerosol generated by the PVU 100. In an embodiment, the power settings of PVU 100 may be set and/or specified such that the user can make setting adjustments to PVU 100 to maximize battery life. In this case, PVU 100 will resultantly operate at lower energy output to preserve the maximum number of cycles that be sustained per battery 104 charge cycle. Conversely the power settings of PVU 100 may be set and/or specified such that the user can maximize performance in relation to the energy output of the device per cycle.

In an embodiment, the liquid related settings of PVU 100 can be based on information about the liquid components and/or formulation, or similar such that the information relating to the liquid to be vaporized or aerosolized. The liquid related settings of PVU 100 can have predetermined as well as user configurable settings to modulate, configure, adjust or otherwise configure the device activation parameters. In an embodiment, settings related to user specific environmental configurations can be made such that PVU 100 optimizes heating element activation and activation parameters to optimize performance based on ambient temperature, humidity, and/or altitude. For example, PVU 100 may have configurations such as cold weather or warm weather settings, humidity settings, and/or altitude settings.

In an embodiment, PVU 100 can be configured (programmed) with time based settings. For example, user specific temporal configurations such as the user preferring higher active component delivery per inhalation at specific times of the day. PVU 100 can be configured such that PCU 100 delivers dosages of an active component based on the time of day. For example, PVU 100 can be configured such that such that the dosage delivered to the user is highest, or at maximum value (or similar) in the morning and tapers down to a lower delivered dose per inhalation, or minimum value (or similar) at the end of the evening. The user can program these settings (and others described herein) based on personal preference.

In an embodiment, taste and/or flavor related settings of PVU 100 can minimize, maximize, and or modulate the functional effects of the taste and/or flavor component of the vapor product. For example, PVU 100 can be configured to activate in such a way that the flavor delivered from the vapor or aerosol is minimized, maximized, or modulated over the period of an inhalation. Some components of the liquid being vaporized that may contribute to the flavor characteristics of the vapor or aerosol may be more profound, more prevalent, or more substantial when PCU 100 is activated with higher temperature ranges being generated by the heating element than when lower temperature ranges are being generated by the heating element (within the range of temperatures that the heating element may operate in order to generate a vapor or aerosol for inhalation by the user.) For example the user may set PVU 100 to perform for maximal, minimal, moderate, or another interim value of flavor for the vapor or aerosol product. PVU 100 can modulate the heating element activation cycle accordingly.

In an embodiment, functional effect related setting of PVU 100 can minimize, maximize, or modulate the functional effects related to pharmacodynamics and pharmacokinetics of an active ingredient or drug component of the vapor or aerosol product. For example, PVU 100 can be configured to activate in such a way that the active component or drug delivered from the vapor or aerosol is minimized or maximized in terms of target tissue or organ delivery. Active components or drug(s) in a liquid formulation being vaporized can be absorbed into the blood stream at different rates depending on the target tissue or organ.

Active component(s) or drug(s) in a vapor having a small particle size of less than 10 microns may be readily absorbed into systemic circulation through the pulmonary vasculature. However active component(s) or drug(s) in a vapor having a small particle size of greater than 10 microns may be absorbed more preferentially through the mucosal surface of the oral and pharyngeal cavities. Mucosal absorption is slower to reach the systemic circulation than delivery of a drug (or similar) to the systemic circulation through the pulmonary vasculature.

A user may be using PVU 100 for the delivery of nicotine as the active or drug component in the vapor or aerosol. It may be desirable for (or by) the user to have an option for more rapid delivery of the nicotine to the bloodstream—such as after a period of time of not having nicotine (when that the user's urge or craving is likely to be elevated.) Alternatively, at times it may be desirable for (or by) the user to have a slower absorption of nicotine into the blood stream such as at times when: (i) the users craving or urge is low, (ii) when the user wants to have a more prolonged period of time before they have the urge or craving for nicotine—such as prior to going to sleep, or an event where they will be unable to use the device for dosing or administration of the nicotine. PVU settings relating to the activation of the device and the temperature of the heating element and heating element activation characteristics may be modulated such that, for example, at lower temperature activation the particle size of the drug component is larger than at times of a higher temperature activation of the heating element. Thus, by modulating the input of thermal or heat energy inputted into the vaporization chamber by the heating element to volatize or vaporize the liquid containing the active component(s) or drug(s) the characteristics of the vapor or aerosol in relation to the particle size of the active component(s) or drug(s) can be wholly or partially modulated by the user. These settings can also be used by the end user or healthcare provider (or similar) to reduce dependence on the active component(s) or drug(s)—such as nicotine. These settings can also be used, for example, by initially using the device configured to maximize pulmonary deliver of the nicotine and then transition to device settings that maximize mucosal delivery of the nicotine as a means to facilitate a reduction in nicotine dependence. This transition can also be used in conjunction with nicotine dosage reduction as a means of reducing or mitigating the users nicotine dependence or addiction.

In an embodiment, an app may receive alerts and notifications associated with PVU 100 and/or case 500. These alerts and notifications can include, for example: battery life status, battery condition data (such as number of battery cycles), battery "health" (such that the user can be notified, as desired, to the current and "real time" overall condition of the PCU 100 and/or case 500's internal battery(s).

In an embodiment, PVU 100, case 500, and/or an associated application (app) running on a digital consumer technology product may share data with a manufacturer, manufacturer affiliate, or other entity (retailer, healthcare provider, supplier, marketing entity, etc.) Case 500 may share data via an associated application. PVU 100 may share data via case 500 and/or directly to an associated application (for further sharing with another entity).

PVU 100, case 500, and/or an associated application can gather, receive, logging, store, transmit, extrapolate, and/or the like, anonymous or user specific usage data—such as frequency of use. PVU 100, case 500, and/or an associated application can gather, receive, logging, store, transmit, extrapolate, and/or the like, user specific usage data such as activation cycle characteristics such as duration of activations and user specified activation settings (if applicable.) PVU 100, case 500, and/or an associated application can gather, receive, logging, store, transmit, extrapolate, and/or the like, user specific demographic information. PVU 100, case 500, and/or an associated application can gather, receive, logging, store, transmit, extrapolate, and/or the like, user specific socioeconomic information. PVU 100, case 500, and/or an associated application can gather, receive, logging, store, transmit, extrapolate, and/or the like, user specific f information. PVU 100, case 500, and/or an associated application can gather, receive, logging, store, transmit, extrapolate, and/or the like, user specific feedback information. PVU 100, case 500, and/or an associated application can gather, receive, logging, store, transmit, extrapolate, and/or the like, user specific demographic information. PVU 100, case 500, and/or an associated application can gather, receive, logging, store, transmit, extrapolate, and/or the like, user specific feedback information through the use of surveys, polls, and the like, and/or data analytics.

PVU 100, case 500, and/or an associated application can gather, receive, logging, store, transmit, extrapolate, and/or the like, anonymous and/or user specific usage and/or reliability data such as device errors or malfunctions. PVU 100, case 500, and/or an associated application can gather, receive, logging, store, transmit, extrapolate, and/or the like, user specific usage and/or reliability data such as requests for warranty services, repairs, and or replacements, etc. PVU 100, case 500, and/or an associated application can gather, receive, logging, store, transmit, extrapolate, and/or the like, user specific customer satisfaction data such as requests for technical support. PVU 100, case 500, and/or an associated application can gather, receive, logging, store, transmit, extrapolate, and/or the like, user specific sales lead data such as requests for product information. PVU 100, case 500, and/or an associated application can gather, receive, logging, store, transmit, extrapolate, and/or the like, user specific usability data such as requests for usage instructions. PVU 100, case 500, and/or an associated application can gather, receive, logging, store, transmit, extrapolate, and/or the like, user specific information such as requests for information on product features or functions. PVU 100, case 500, and/or an associated application can gather, receive, logging, store, transmit, extrapolate, and/or the like, user specific marketing data such as requests for information on purchasing PVU 100 or case 500 and/or acquiring PVU 100 or case 500 by way of a prescription from a physician or healthcare provider.

PVU 100, case 500, and/or an associated application can gather, receive, logging, store, transmit, extrapolate, and/or the like, PVU 100 data indicating misuse or abuse of PVU 100. PVU 100, case 500, and/or an associated application can gather, receive, logging, store, transmit, extrapolate, and/or the like, PVU 100 and case 500 data and/or data transmission features that can be used to locate PVU 100 and/or case 500. PVU 100, case 500, and/or an associated application can gather, receive, logging, store, transmit, extrapolate, and/or the like, PVU 100 and case 500 data and/or data transmission features that can be used to locate PVU 100 and/or case 500 if PVU 100 or case 500 is lost or stolen. PVU 100, case 500, via an associated application, can gather, receive, logging, store, transmit, extrapolate, and/or the like, notifications regarding product recalls or similar issues and/or inform the user of such recalls or issues. PVU 100, case 500, via an associated application, can gather, receive, logging, store, transmit, extrapolate, data sharing, and/or the like, notifications manufacturer terms and conditions (e.g., cartridge manufacturer) and/or inform the user of such terms and conditions, and/or receive approval of such terms and conditions from the user.

PVU 100, case 500, via an associated application, can gather, receive, logging, store, transmit, extrapolate, data share, and/or the like, data from a network that may be used to identify, contact, or connect with other users of PVU 100. PVU 100, case 500, via an associated application, can gather, receive, logging, store, transmit, extrapolate, data share, and/or the like, data from a network that may be used to identify, contact, or connect with other users of PVU 100 wherein the network comprises a wireless communication link. PVU 100 and/or case 500 may select and/or authorize the sharing of all or some of the data gathered, received, logged, stored, transmitted, extrapolated, shared, or the like by the PVU 100 and/or case 500, or gathered directly from the user through the use of applications associated with PVU 100 and/or case 500. PVU 100 and/or case 500 may select and/or authorize the sharing, via a network, of all or some of the data gathered, received, logged, stored, transmitted, extrapolated, shared, or the like by the PVU 100 and/or case 500, or gathered directly from the user through the use of applications associated with PVU 100 and/or case 500. The network may comprise social media. The social media membership may comprise a user's family. The social media membership may comprise a user's friends. The social media membership may comprise a support group or similar (e.g., quit smoking group). The social media membership may comprise a third party service, company, organization (e.g., church), other users of PVU 100, or the like.

PVU 100, case 500, and/or an associated application can gather, receive, logging, store, transmit, extrapolate, and/or the like, data useful to perform software configuration of the device and or the device application(s). PVU 100, case 500, and/or an associated application can gather, receive, logging, store, transmit, extrapolate, and/or the like, data useful or required to perform software configuration of the PVU 100, case 500, and/or the associated application(s). PVU 100, case 500, and/or an associated application can gather, receive, logging, store, transmit, extrapolate, and/or the like, data useful or required to perform software configuration of the PVU 100, case 500, and/or the associated application(s) where the software is configured by the manufacturer or manufacturers subsidiary or representatives or third party or similar. PVU 100, case 500, and/or an associated application can gather, receive, logging, store, transmit, extrapolate, and/or the like, data useful or required to perform third party software configuration of PVU 100, case 500, and/or the associated application(s). PVU 100, case 500, and/or an associated application can gather, receive, logging, store, transmit, extrapolate, and/or the like, data useful or required to perform firmware updates of PVU 100, case 500, and/or the associated application(s). PVU 100, case 500, and/or an associated application can provide for the notification of the user via PVU 100, case 500, and/or an associated application that a firmware or similar updates to PVU 100, case 500, and/or an associated application is available and or required as a means of trouble shooting the device or remediating a problem or issue with PVU 100, case 500, and/or an associated application which is preventing some aspect of intended or proper function(s) of PVU 100, case 500, and/or an associated application. PVU 100, case 500, and/or an associated application can provide for the notification of the user via PVU 100, case 500, and/or an associated application that a firmware or similar updates to PVU 100, case 500, and/or an associated application is available and or required as a means of means of providing additional functions relating to or intended to improved PVU 100 or case 500 performance, enhance user experience, or similarly improve some aspect of intended or proper function(s) of PVU 100, case 500, and/or an associated application.

PVU 100, case 500, and/or an associated application can share data gathered by PVU 100, case 500, or gathered directly from the user through the use of the application with the user's healthcare provider. PVU 100, case 500, and/or an associated application can share data gathered by PVU 100, case 500, or gathered directly from the user through the use of the application with the user's healthcare network. PVU 100, case 500, and/or an associated application can share data gathered by PVU 100, case 500, or gathered directly from the user through the use of the application with the user's insurance provider. PVU 100, case 500, and/or an associated application can share data gathered by PVU 100, case 500, or gathered directly from the user through the use of the application with the user's pharmacy and/or prescription drug provider, or the like. PVU 100, case 500, and/or an associated application can depersonalized or otherwise made anonymous data gathered by PVU 100, case 500, or gathered directly from the user so that the depersonalized data can be shared used for purposes such as research, analysis, publication, or similar purposes.

PVU 100, case 500, and/or an associated application can provide for the notification of the user via PVU 100, case 500, and/or the associated application of the availability of a prescription issued or written for the end user being ready for pick-up, delivery, shipment to the user or similar of a prescription component intended for delivery to the patient by PVU 100. For example, a pharmacy could send a notification to the user, via PVU 100, case 500, and/or an associated application, such as to notify the user that their prescription for PVU 100 or device components (e.g., cartridges or liquids) is available for the user to pick up from the pharmacy. PVU 100, case 500, and/or an associated application can allow for healthcare providers, networks, agents, authorized third parties or similar to send alerts, messages, surveys, or similar to the user via PVU 100, case 500, and/or the associated application. PVU 100, case 500, and/or an associated application can allow for healthcare providers, networks, agents, authorized third parties or similar to access data that is generated as a result of surveys, or similar through PVU 100, case 500, and/or the associated application.

PVU 100, case 500, and/or an associated application can authorize (i.e., allow) a healthcare provider to configure, adjust, modulate, and/or manipulate PVU 100 settings. PVU 100, case 500, and/or an associated application can authorize a healthcare provider to configure, adjust, modulate, and/or manipulate PVU 100 settings which the user is not authorized to change, alter, reconfigure or change the settings, configurations, etc. made by the healthcare provider. PVU 100, case 500, and/or an associated application can authorize a representative or agent of the healthcare provider to configure, adjust, modulate, and/or manipulate PVU 100 settings which the user is not authorized to change, alter, reconfigure or change the settings, configurations, etc. made by the representative or agent of the healthcare provider.

PVU 100, case 500, and/or an associated application can share user specific information, such as end user ownership of products relating to the device, device components, device accessories or similar data, gathered by PVU 100, case 500, or gathered directly from the user through the use of the application. PVU 100, case 500, and/or an associated application can share user specific information, user specific information such as end user purchasing of products relating to the device, device components, device accessories or similar data, gathered by PVU 100, case 500, or gathered directly from the user through the use of the application. PVU 100, case 500, and/or an associated application can provide for the notification of the user via PVU 100, case 500, and/or the associated application of notifications from retailer(s) or similar regarding product promotions. PVU 100, case 500, and/or an associated application can provide for the notification of the user via PVU 100, case 500, and/or the associated application similar of notifications from retailer(s) or similar regarding product availability. PVU 100, case 500, and/or an associated application can provide for the notification of the user via PVU 100, case 500, and/or the associated application similar of notifications from retailer(s) or similar regarding release of new product or accessories.

PVU 100, case 500, and/or an associated application can use demographic or similar location services to find retail locations in geographic proximity of the user. PVU 100, case 500, and/or an associated application can gather, receive, logging, store, transmit, extrapolate, and/or the like, data relating to device purchasing, device accessories purchasing, vaporizer liquid and associated packaging or assembly purchasing, frequency of purchasing, point of sale, discounts applied by user when purchasing, and related or similar information. PVU 100, case 500, and/or an associated application can gather, receive, logging, store, transmit, extrapolate, and/or the like, data relating to device purchasing, device accessories purchasing, vaporizer liquid and associated packaging or assembly purchasing, frequency of purchasing, point of sale, discounts applied, and related or similar information.

PVU 100, case 500, and/or an associated application can provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar. PVU 100, case 500, and/or an associated application can provide for the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

PVU 100, case 500, and/or an associated application can render PVU 100 inactive and unable to be used. PVU 100, case 500, and/or an associated application can render PVU 100 inactive and unable to be used if a malfunction or similar has occurred. PVU 100, case 500, and/or an associated application can render PVU 100 inactive and unable to be used until the authorized user enters a Personal Identification Number (PIN) using the application which then activates PVU 100. PVU 100, case 500, and/or an associated application can render PVU 100 inactive and unable to be used until the authorized user has a biometric identifier that when recognized or confirmed or verified or similar, using the application or case 500, activates PVU 100. PVU 100, case 500, and/or an associated application can render PVU 100 inactive and unable to be used until the authorized user uses a fingerprint as a biometric identifier that when recognized or confirmed or verified or similar, using the application or case 500, activates PVU 100. PVU 100, case 500, and/or an associated application can render PVU 100 inactive and unable to be used until the authorized user uses an eye, or iris, or similar scan, as a biometric identifier that when recognized or confirmed or verified or similar, using the application or case 500, activates PVU 100. PVU 100, case 500, and/or an associated application can render PVU 100 inactive and unable to be used until the authorized user is recognized or confirmed or verified or similar, using facial recognition, the application or case 500, activates PVU 100.

Unauthorized use of PVU 100, case 500, and/or an associated application can be prevented by using PIN or unique biometric identifier to enable PVU 100, case 500, and/or an associated application. PVU 100, case 500, and/or an associated application can share data relating to the attempted unauthorized use of PVU 100. PVU 100, case 500, and/or an associated application can share data over a network to authorize the user and activate PVU 100. PVU 100, case 500, and/or an associated application can share data such that biometric authentication can be performed through the use of a network. PVU 100, case 500, and/or an associated application can use time or duration of time that passes after use before PVU 100 is rendered inactive and authentication is required to authorize PVU 100.

PVU 100, case 500, and/or an associated application can save device data and personal settings for individual users so that more than one user may use PVU 100 and/or case 500. PVU 100, case 500, and/or an associated application can save device data and personal settings to be saved for individual users where the settings for device data and personal settings for different users can be applied to PVU 100 and/or case 500 and the intended user through the application and the user may select their saved configurations for PVU 100 and/or case 500 and the respective device will operate under that user selected configuration. PVU 100, case 500, and/or an associated application can have the ability for the user or users to have one or more of user settings and/or configurations that are saved and can be selected by users. PVU 100, case 500, and/or an associated application can have the ability to allow saved user settings and personal settings or configurations to be shared by the user through the application and/or an associated network. PVU 100, case 500, and/or an associated application can allow other user settings and/or configurations to be shared with the user through the application or an associated network.

PVU 100, case 500, and/or an associated application can have the ability to facilitate, prompt, or the like, a user to rate (such as through common methods such a 1-10 where "10" is the best, or 1-5 "stars" where "5" stars is the best) their user configurations. PVU 100, case 500, and/or an associated application can have the ability to facilitate, prompt, or the like, the user to rate other user configurations. PVU 100, case 500, and/or an associated application can have the ability to share and access a data base of user configurations that may or may not have ratings and be able to access the user configurations through the application and download user configurations for use in the users own device. PVU 100, case 500, and/or an associated application can have the ability to share and access a data base of user configurations that may or may not have ratings and a be able to access the user configurations through the application and upload their user configurations for use in other users devices.

PVU 100, case 500, and/or an associated application can share user data with the manufacturer, manufacturers subsidiaries, manufactures agents, or a third party for the purpose of generating user profiles based on user specific usage data, demographic data, socioeconomic data or similar. PVU 100, case 500, and/or an associated application can have the ability to utilize user data shared with the manufacturer, manufacturers subsidiaries, manufactures agents, or a third party to determine specific user profiles.

PVU 100, case 500, and/or an associated application can allow, facilitate, authorize, confirm or similar the sharing of data between the associated application and other application(s) that may be installed or a component of the user's personal digital device. PVU 100, case 500, and/or an associated application can share information and/or data with a social media application. PVU 100, case 500, and/or an associated application can share information and/or data with email service, email provider, email hosting, or similar application. PVU 100, case 500, and/or an associated application can share information and/or data with text message, SMS, or similar application. PVU 100, case 500, and/or an associated application can share information and/or data with a location based services application. PVU 100, case 500, and/or an associated application can share information and/or data with a map or mapping, navigation, location or similar application. PVU 100, case 500, and/or an associated application can share information and/or data with healthcare, healthcare provider, healthcare services, healthcare network or similar application. PVU 100, case 500, and/or an associated application can share information and/or data with pharmacy, or pharmacy type service provider or similar application. PVU 100, case 500, and/or an associated application can share information and/or data with a weather, or weather forecasting, or weather reporting, or similar application. PVU 100, case 500, and/or an associated application can share information and/or data with the device manufacturers application. PVU 100, case 500, and/or an associated application can share information and/or data with a research or research orientated application. PVU 100, case 500, and/or an associated application can share information and/or data with a PVU 100 and/or case 500 retailer or similar consumer device application.

PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of addressing problems with device performance or function. PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of addressing problems with device application(s). PVU 100, case 500, and/or an associated application can have the ability to authorize or allow data gathering, receiving, logging, storing, transmission, extrapolation or similar for the purpose of the device or device application sending error codes or error reports to the manufacturer, manufacturers subsidiaries, manufactures agents, or a third party for the purpose of extrapolating data metrics that relate to device malfunctioning. PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of gathering, receiving, logging, storing, transmission, extrapolation or similar data that may relate to manufacturing, or quality control or similar issues or potential problems related to the device, device components, or liquid being used in the device. PVU 100, case 500, and/or an associated application can have the ability to gather, receive, log, store, transmit, extrapolate, or similar, data for the purpose of troubleshooting device issues or problems. PVU 100, case 500, and/or an associated application can have the ability to gather, receive, log, store, transmit, extrapolate, or similar, data for the purpose of troubleshooting device issues or problems that may relate to user error.

PVU 100, case 500, and/or an associated application can have the ability to use methods of data transmission such as wireless and wired technologies. PVU 100, case 500, and/or an associated application can have the ability to use methods of data transmission such as wireless and wired technologies to perform one or more of the functions, capabilities, methods, abilities, etc., described herein. PVU 100, case 500, and/or an associated application can have the ability to use methods of data transmission such as wifi, Bluetooth, cellular, 3G, 4G, near field communication (NFC), or similar for the transmission of data to the users personal digital device. PVU 100, case 500, and/or an associated application can have the ability to use methods of data transmission such as wifi, Bluetooth, cellular, 3G, 4G, near field communication (NFC), or similar for the transmission of data to a network. PVU 100, case 500, and/or an associated application can have the ability to use methods of data transmission such as text messaging or SMS. PVU 100, case 500, and/or an associated application can have the ability to use methods of data transmission such as electronic mail or email. PVU 100, case 500, and/or an associated application can have the ability to use methods of data transmission such as notifications or push notifications to the user's digital device.

PVU 100, case 500, and/or an associated application can have means for user control of the functionality, features, configurations etc. of PVU 100, case 500, and/or an associated application through the use of various features of the application referred to as configurations or settings. These settings can include, but are not limited to exemplary general usage settings listed in Table 1.

TABLE 1

(a) Desired number of activations cycles over a period of time.
(b) Configuring and or setting reminders, alarms, or similar to notify the user.
(c) Desired dose delivery of active substance per inhalation.
(d) Desired total delivered dose over a period of time such as a total daily dose.
(e) Power settings of PVU 100 to modulate the vapor or aerosol strength, vapor or aerosol density, vapor or aerosol volume, vapor or aerosol flavor, vapor or aerosol temperature or similar vapor or aerosol characteristics of the vapor or aerosol generated by the device. The power settings could modulate or configure the activation energy delivered to the heating element(s) as well as modulating or configuring the parameters of the heating element(s) being energized in relation to the time to peak activation or "warm up" or "ramp" and or the time of maximum or peak activation, and or the time of the heating element being deactivated or the "cool down" to effect and modulate the vapor or aerosol strength, vapor or aerosol density, vapor or aerosol volume, vapor or aerosol flavor, vapor or aerosol temperature or similar characteristics of the vapor or aerosol generated by the device.

TABLE 1-continued (f) Power settings of PVU 100 to modulate, adjust, configure or similar the settings of the device as they relate to battery life and performance such that the user can make setting adjustment to the device to maximize battery life and the device will resultantly operate at lower energy output to preserve the maximum number of cycles that be sustained per battery charge cycle. Conversely the user could modulate, adjust, configure or similar the settings of the device to maximize performance in relation to the energy output of the device per cycle.

(g) Settings related to the liquid components and formulation or similar such that the information relating to the liquid to be vaporized or aerosolized can have predetermined as well as user configurable settings to modulate, configure, adjust or similar PVU 100 activation parameters.

(h) Settings related to user specific environmental configurations such as cold weather or warm weather settings such that the device optimizes heating element activation and activation parameters to optimize performance based on ambient temperature.

(i) Settings related to user specific environmental configurations such as high or low humidity settings such that PVU 100 optimizes heating element activation and activation parameters to optimize performance based on user locale humidity values or ranges.

(j) Settings related to user specific environmental configurations such as user locale altitude settings such that PVU 100 optimizes heating element activation and activation parameters to optimize performance based on end user altitude.

(k) Settings related to user specific temporal configurations such as the user preferring higher active component delivery per inhalation at specific times of the day. For example, PVU 100 can be configured such that it delivers higher dosage of active component related to a time of day such that the dosage delivered to the user is highest, or at maximum value or similar in the morning and tapers down to a lower delivered dose per inhalation, or minimum value, or similar at the end of the evening. This is an example of the configurability of PVU 100 and the user could program the settings based on personal preference.

(l) Settings related to modulating PVU 100 performance and activation parameters to minimize or maximize the functional effects of the taste or flavor component of the vapor product such that PVU 100 can be configured to activate in such a way that the flavor delivered from the vapor or aerosol is minimized or maximized. For example components of the liquid being vaporized that may contribute to the flavor characteristics of the vapor or aerosol may be more profound, or more prevalent, or more substantial when PVU 100 is activated with higher temperature ranges being generated by the heating element than when lower temperature ranges are being generated by the heating element within the range of temperatures that the heating element may operate within in order to generate a vapor or aerosol for inhalation by the user. For example the user may set PVU 100 to perform for maximal, minimal, moderate, or another interim value of flavor for the vapor or aerosol product and the heating element activation cycle will be modulated accordingly.

(m) Settings related to modulating PVU 100 performance and activation parameters to minimize or maximize the functional effects related to pharmacodynamics and pharmacokinetics of the active or drug component of the vapor or aerosol product such that PVU 100 can be configured to activate in such a way that the active component or drug delivered from the vapor or aerosol is minimized or maximized in terms of target tissue or organ delivery. For example active components or drug(s) in the liquid formulation being vaporized will be absorbed into the blood stream at different rates depending on the target tissue or organ. For example active component(s) or drug(s) in the vapor having small particle size of less than 10 microns may be readily absorbed into systemic circulation through the pulmonary vasculature, as is well documented in the literature. However active component(s) or drug(s) in the vapor having small particle size of greater than 10 microns may be absorbed more preferentially through the mucosal surface of the oral and pharyngeal cavities and mucosal absorption is slower to reach the systemic circulation then is the delivery of a drug or similar to the systemic circulation through the pulmonary vasculature. To continue the example, a user may be using PVU 100 for the delivery of nicotine as the active or drug component in the vapor or aerosol and it may be desirable for the user to have the option to have more rapid delivery of the nicotine to the bloodstream, such as after a period of time of not having nicotine such that the user's urge or craving is elevated. Alternatively, at times it may be desirable for the user to have a slower absorption of nicotine into the blood stream such as at times when the users craving or urge is low, or at times when the user wants to have a more prolonged period of time before they have the urge or craving for nicotine such as prior to going to sleep, or an event where they will be unable to use PVU 100 for dosing or administration of the nicotine. PVU 100 settings relating to the activation of the device and the temperature of the heating element and heating element activation characteristics may be modulated such that for example at lower temperature activation the particle size of the drug component is larger than when at higher temperature activation of the heating element. Thus by modulating the input of thermal or heat energy inputted into the vaporization chamber by the heating element to volatize or vaporize the liquid containing the active component(s) or drug(s) the TABLE 1-continued characteristics of the vapor or aerosol in relation to the particle size of the active component(s) or drug(s) can be wholly or partially modulated by the user. These settings could also be used by the end user or healthcare provider or similar to reduce dependence on the active component(s) or drug(s) such as nicotine, for example, by initially using PVU 100 configured to maximize pulmonary deliver of the nicotine and then transition to device settings that maximize mucosal delivery of the nicotine as a means to facilitate reducing nicotine dependence and could be used in conjunction with nicotine dosage reduction as a means of reducing or mitigating the users nicotine dependence or addiction.
(n) Device alerts and notifications such as battery life status and battery condition(s) data such as number of battery cycles and battery "health" such that the user can be notified as desired to the current meaning "real time" and overall condition of the devices internal battery, and the devices charging case internal battery.
(o) Device alerts and notifications such as the PVU 100 battery requiring recharging.
(p) Device alerts and notifications such as case 500 battery requiring recharging.
(q) Device alerts and notifications such as PVU 100 battery being fully charged.
(r) Device alerts and notifications such as case 500 battery being fully charged
(s) Device alerts and notifications such as liquid cartridge status, such as number of usages or inhalations taken and number or usages remaining.
(t) Device alerts and notifications such as liquid cartridge contents such as active component(s) and strength or dosage or similar, and flavor profile or similar, and general formulation.
(u) Device alerts and notifications such as liquid cartridge or liquid cartridge assembly or similar requiring replacement.
(v) Device alerts and notifications such as predetermined or preset times for usage of PVU 100.
(w) Device alerts and notifications such as device heating element status or "health" such as number of cycles performed and number of cycles remaining before suggested or required replacement of heating element or heating element assembly.

Settings can include, but are not limited to device manufacturer data sharing settings listed in Table 2.

TABLE 2

(a) Anonymous or user specific usage data such as frequency of use.
(b) Anonymous or user specific usage data such as activation cycle characteristics such as duration of activations and user specified activation settings if applicable.
(c) User specific data such as demographic information.
(d) User specific data such as socioeconomic information.
(e) User specific data such as user feedback through the use of surveys or similar.
(f) Anonymous or user specific usage data such device errors or malfunctions.
(g) User specific data such as requests for warranty services or repairs or replacements or similar.
(h) User specific data such as requests for technical support.
(i) User specific data such as requests for product information.
(j) User specific data such as requests for usage instructions.
(k) User specific data such as requests for information on product features or functions.
(l) User specific data such as requests for information on purchasing product or acquiring the product through a prescription from a physician or healthcare provider.
(m) Device data indicating misuse or abuse of the device.
(n) Device data and data transmission features used to locate the device if the device is lost or stolen.
(o) Notifications to the user through the device or application(s) relating to product recall(s) or similar issues.
(p) General data sharing to manufacture terms and conditions recognition and user agreement to said terms.

Settings can include, but are not limited to user, usage, system, device, and operational data settings listed in Table 3.

TABLE 3

(a) Settings relating to selecting and authorizing the sharing of all or some of the data gathered by the device or gathered directly from the user through the use of a application(s) to a network(s).
(b) Where network(s) may be social media.

TABLE 3-continued (c) Where network(s) may be comprised of the users family and or friends.
(d) Where network(s) may be comprised of a support group or similar.
(e) Settings relating to the use of the sharing of data over a network(s) that may be used to identify, contact, or connect with other users of the device.
(f) Where other network(s) may be a third party service, company, organization or similar.

Settings can include, but are not limited to software configuration and firmware updating settings listed in Table 4.

TABLE 4

(a) Settings relating to the sharing and transmission of data required or useful to perform software configuration of the device and or the device application(s).
(b) Settings relating to the sharing and transmission of data required to perform software configuration of the device and or the device application(s) where the software is configured by the manufacturer or manufacturers subsidiary or representatives or third party or similar.
(c) Settings relating to the sharing and transmission of data required to perform software configuration of the device and or the device application(s) where the software is configured by the a third party.
(d) Settings relating to the authorization for the sharing and transmission of data required to perform firmware or similar updates to the device and or application.
(e) Settings relating to the notification of the user through the device or application(s) that a firmware or similar updates to the device and or application(s) is available and or required.
(f) Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s).

Settings can include, but are not limited to healthcare system data sharing settings listed in Table 5.

TABLE 5

(a) Settings relating to the sharing of all or some of the data gathered by the device or gathered directly from the user through the use of application(s) to the users healthcare provider.
(b) Settings relating to the sharing of all or some of the data gathered by the device or gathered directly from the user through the use of application(s) to the users healthcare network.
(c) Settings relating to the sharing of all or some of the data gathered by the device or gathered directly from the user through the use of application(s) to the users insurance provider.
(d) Settings relating to the sharing of all or some of the data gathered by the device or gathered directly from the user through the use of application(s) to the users pharmacy or prescription drug provider or similar.
(e) Settings relating to the notification of the availability of a prescription issued or written for the end user being ready for pick-up, delivery, shipment to the user or similar of a prescription component intended for delivery to the patient by the device. For example, a pharmacy could send a notification to the user, through the device application, such as to notify the user that their prescription for the device or device components is available for the user to pick up from the pharmacy.
(f) Settings relating to the authorization of a healthcare provider to configure, adjust, modulate, manipulate or similar the device settings.
(g) Settings relating to the authorization of a healthcare provider to configure, adjust, modulate, manipulate or similar the device settings where the user is not authorized to change, alter, reconfigure or similar the settings, configurations, or similar made by the healthcare provider.
(h) Settings authorizing a representative or agent or similar of the healthcare provider to configure, adjust, modulate, manipulate or similar the device settings where the user is not authorized to change, alter, reconfigure or similar the settings, configurations, or similar made by the healthcare representative or agent or similar.
(i) Settings allowing for data shared with the healthcare provider or network to be depersonalized or otherwise made anonymous and used for other purposes such as research, analysis, publication, or similar purposes.
(j) Settings allowing for healthcare providers, networks, agents, authorized third parties or similar to send alerts, messages, surveys, or similar through the device application(s).
(k) Settings allowing for healthcare providers, networks, agents, authorized third parties or similar to access data that is generated as a result of surveys, or similar through the device application(s).

Settings can include, but are not limited to retailer and/or consumer facing data settings listed in Table 6.

TABLE 6

(a) Settings relating to the sharing user specific information such product, device, component, accessories or similar details.
(b) Settings relating to receiving notifications from retailer(s) or similar regarding product promotions.
(c) Settings relating to receiving notifications from retailer(s) or similar regarding product availability.
(d) Settings relating to receiving notifications from retailer(s) or similar regarding release of new product or accessories.
(e) Settings relating to using demographic or similar location services to find retail locations in geographic proximity of the user.
(f) Settings relating to the sharing of data that may be used for demographic, socioeconomic, or similar marketing or promotional activities.
(g) Settings relating to the gathering of data relating to device purchasing, device accessories purchasing, vaporizer liquid and associated packaging or assembly purchasing, frequency of purchasing, point of sale, discounts applied by user when purchasing, and related or similar information.
(h) Settings relating to the sharing of data relating to device purchasing, device accessories purchasing, vaporizer liquid and associated packaging or assembly purchasing, frequency of purchasing, point of sale, discounts applied, and related or similar information..

TABLE 6-continued (i) The use of the application to provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar.
(j) Settings relating to the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

Settings can include, but are not limited to device access settings listed in Table 7.

TABLE 7

(a) Settings relating to rendering the device inactive and unable to be used.
(b) Settings relating to rendering the device inactive and unable to be used where the authorized user has a Personal Identification Number (PIN) that when entered using the application activates the device.
(c) Settings relating to rendering the device inactive and unable to be used where the authorized user has a biometric identifier that when recognized or confirmed or verified or similar using the application activates the device.
(d) Settings relating to rendering the device inactive and unable to be used where the authorized user has a biometric identifier that when recognized or confirmed or verified using the application activates the device where the biometric identifier is a fingerprint.
(e) Settings relating to rendering the device inactive and unable to be used where the authorized user has a biometric identifier that when recognized or confirmed or verified using the application activates the device where the biometric identifier is an eye or iris or similar scan.
(f) Settings relating to rendering the device inactive and unable to be used where the authorized user has a biometric identifier that when recognized or confirmed or verified using the application activates the device where the biometric identifier is facial recognition.
(g) Settings where unauthorized use of the device is prevented by using PIN or unique biometric identifier.
(h) Settings relating to the sharing of data relating to the attempted unauthorized use of the device.
(i) Settings relating the sharing of data over a network to authorize the user and activate the device.
(j) Settings relating to sharing of data such that biometric authentication can be performed through the use of a network.
(k) Settings related to the time or duration of time that passes after use before the device is rendered inactive and authentication is required to authorize the device.
(l) Settings related the resetting or changing of user specific authentication information such as the PIN.

Settings can include, but are not limited multiple user settings listed in Table 8.

TABLE 8

(a) Settings relating to the sharing and transmission of data required or useful to perform software configuration of the device and or the device application(s).
(b) Settings relating to the sharing and transmission of data required to perform software configuration of the device and or the device application(s) where the software is configured by the manufacturer or manufacturers subsidiary or representatives or third party or similar.
(c) Settings relating to the sharing and transmission of data required to perform software configuration of the device and or the device application(s) where the software is configured by the a third party.

TABLE 8-continued (d) Settings relating to the authorization for the sharing and transmission of data required to perform firmware or similar updates to the device and or application.
(e) Settings relating to the notification of the user through the device or application(s) that a firmware or similar updates to the device and or application(s) is available and or required.
(f) Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s).

Settings can include, but are not limited to, defined usage profile settings listed in Table 9.

TABLE 9

(a) Settings related to the sharing of user data to the manufacturer, manufacturers subsidiaries, manufactures agents, or a third party for the purpose of generating user profiles based on user specific usage data, demographic data, socioeconomic data or similar.
(b) Where the use of user data shared with or sent to the manufacturer, manufacturers subsidiaries, manufactures agents, or a third party for the purpose of generating user profiles based on user specific usage data, demographic data, socioeconomic data or similar is utilized to determine specific user profiles.
(c) Where the user profiles are a group of setting configurations that correlate to a specific subset of users.
(d) Where a subset of users may be based of demographic data, socioeconomic, personal data gathered through the use of the application, device usage data or similar.
(e) Where user profiles may be specific to the subset of users and recommended device configuration base on user profile data could be available to the user of the device based on the users similarities to a subset of users.
(f) Where the user experience is optimized by using cumulative data from similar users to establish a default setting configuration for the device based on the users demographic data, socioeconomic data or similar.

Settings can include, but are not limited to setting related to integration with other applications listed in Table 10.

TABLE 10

(a) Settings to allow, facilitate, authorize, confirm or similar the sharing of data between the device application and other application(s) that may be installed or a component of the users personal digital device.
(b) Where other application(s) that the device application shares information with may be social media application(s).
(c) Where other application(s) that the device application shares information with may be email service, email provider, email hosting, or similar application(s).
(d) Where other application(s) that the device application shares information with may be text message, SMS, or similar application(s).
(e) Where other application(s) that the device application shares information with may be location services application(s).
(f) Where other application(s) that the device application shares information with may be map or mapping, navigation, location or similar application(s).
(g) Where other application(s) that the device application shares information with may be healthcare, healthcare provider, healthcare services, healthcare network or similar application(s).
(h) Where other application(s) that the device application shares information with may be pharmacy, or pharmacy type service provider or similar application(s).
(i) Where other application(s) that the device application shares information with may be weather, or weather forecasting, or weather reporting or similar application(s).
(j) Where other application(s) that the device application shares information with may be the device manufacturers application(s).

TABLE 10-continued (k) Where other application(s) that the device application shares information with may be research or research orientated application(s).
(l) Where other application(s) that the device application shares information with may be device retailer or similar consumer device application(s).

Settings can include, but are not limited to error code and troubleshooting settings listed in Table 11.

TABLE 11

(a) Settings relating to the authorization or allowance of data sharing for the purpose of the device or device application sending error codes or error reports to the manufacturer, manufacturers subsidiaries, manufactures agents, or a third party for the purpose of addressing problems with device performance or function.
(b) Settings relating to the authorization or allowance of data sharing for the purpose of the device or device application sending error codes or error reports to the manufacturer, manufacturers subsidiaries, manufactures agents, or a third party for the purpose of addressing problems with device application(s).
(c) Settings relating to the authorization or allowance of data sharing for the purpose of the device or device application sending error codes or error reports to the manufacturer, manufacturers subsidiaries, manufactures agents, or a third party for the purpose of extrapolating data metrics that relate to device malfunctioning.
(d) Settings relating to the authorization or allowance of data sharing for the purpose of the device or device application sending error codes or error reports to the manufacturer, manufacturers subsidiaries, manufactures agents, or a third party for the purpose of gathering data that may relate to manufacturing, or quality control or similar issues or potential problems related to the device, device components, or liquid being used in the device.
(e) Settings relating to the sharing of data for the purpose of troubleshooting device issues or problems.
(f) Settings relating to the sharing of data for the purpose of troubleshooting device issues or problems that may relate to user error.

Settings can include, but are not limited to settings related to methods of communication in Table 12.

TABLE 12

(a) Settings relating to the device or device application using methods of data transmission such as wireless and wired technologies.
(b) Settings relating to the device or device application using methods of data transmission such as wifi, Bluetooth, or similar for the transmission of data to the users personal digital device.
(c) Settings relating to the device or device application using methods of data transmission such as wired or wireless methods or similar for the transmission of data to a network.
(d) Settings relating to the device or device application using methods of data transmission such as text messaging or SMS.
(e) Settings relating to the device or device application using methods of data transmission such as electronic mail or email.
(f) Settings relating to the device or device application using methods of data transmission such as notifications or push notifications on the users digital device.

In an embodiment, an application associated with PVU 100 and/or case 500 can provide an authentication process to activate the device. The application can provide an authentication process to activate the device that verifies the user's age at or prior to establishing a unique identification profile for the end user to prevent unintended use or abuse of the device by minors. Demographic, socioeconomic, and device usage data can be used to establish a user profile. Pooled user profiles can be used to establish a starting configuration of device settings for a new user based on pooled data on usage and settings of similar users based wholly or partially on demographic, socioeconomic, and device usage data. The application can be used to provide information to the user on the operation of the device. The application can be used to provide the user with information on how to configure, adjust, modulate, modify, or similar the device settings.

The application can be used to provide information on trouble shooting the device in the event of a performance issue or malfunction. The application can be used to provide safety information relating to the device to the user. The application can be used to provide safety information relating to the maintenance, cleaning, or similar activities for the device. The application can be used to provide storage information for the device. The application can be used to provide information relating to the disposal or recycling of the device. The application can be used to provide information on the proper disassembly and assembly of the device. The application can be used to provide information such as the manufacturers, distributors, retailers, or similar website and or contact information. The application can be used to provide information such as a website URL or link for internet forums that may relate to the use, troubleshooting, user experience, user reviews or similar. The application can be used to provide safety information relating to the device to the user. The application can be used to provide information on available products, accessories, or similar that may be related to the device. The application can be used to provide a space for advertising consumer products or services that may be related to the device. The application can be used to provide functions relating to personal user goals for device usage and to track usage as it relates to the users defined goals and to prevent the data in the forms of charts, graphs, or similar.

Figure 75:
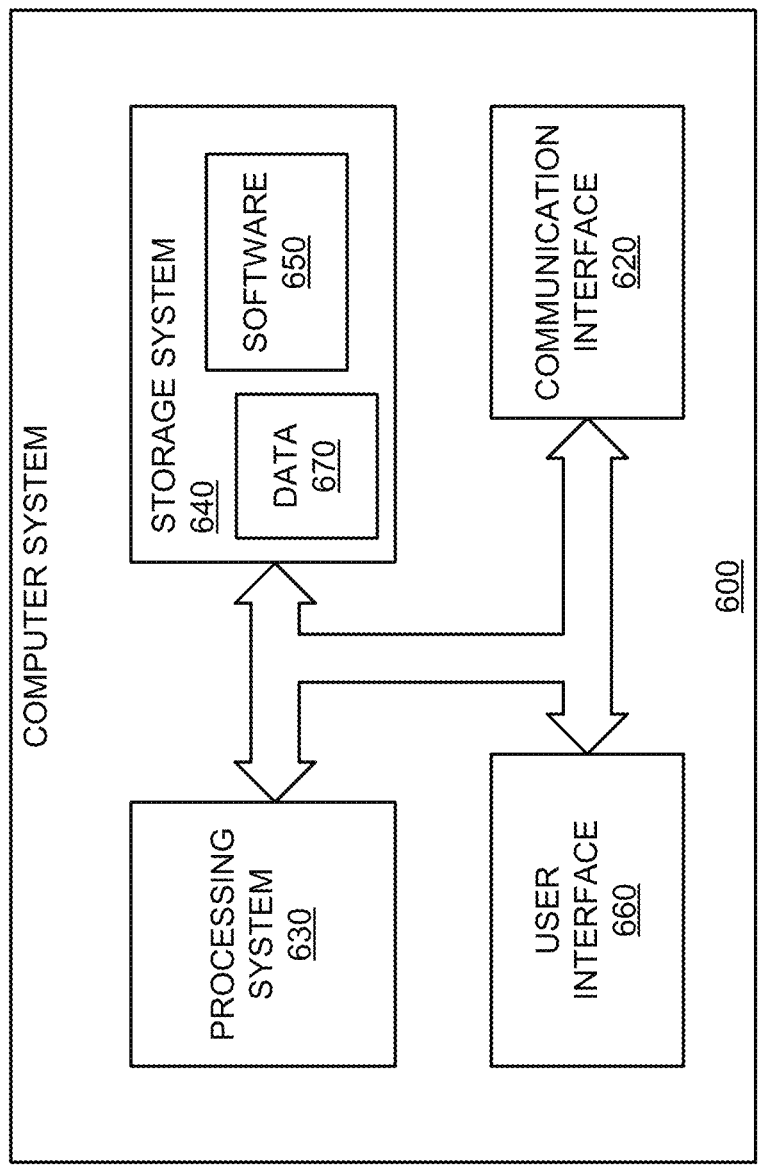
FIG. 75 is a block diagram of a computer system.

The systems, controller, and functions described above may be implemented with or executed by one or more computer systems. The methods described above may be stored on a computer readable medium. Personal vaporizer unit 100, case 500, system 7600, system 7700, system 7800, communication system 7900, and/or authorization system 8000 may be, comprise, or include computers systems. FIG. 75 illustrates a block diagram of a computer system. Computer system 600 includes communication interface 620, processing system 630, storage system 640, and user interface 660. Processing system 630 is operatively coupled to storage system 640. Storage system 640 stores software 650 and data 670. Processing system 630 is operatively coupled to communication interface 620 and user interface 660. Computer system 600 may comprise a programmed general-purpose computer. Computer system 600 may include a microprocessor. Computer system 600 may comprise programmable or special purpose circuitry. Computer system 600 may be distributed among multiple devices, processors, storage, and/or interfaces that together comprise elements 620-670.

Communication interface 620 may comprise a network interface, modem, port, bus, link, transceiver, or other communication device. Communication interface 620 may be distributed among multiple communication devices. Processing system 630 may comprise a microprocessor, microcontroller, logic circuit, or other processing device. Processing system 630 may be distributed among multiple processing devices. User interface 660 may comprise a keyboard, mouse, voice recognition interface, microphone and speakers, graphical display, touch screen, or other type of user interface device. User interface 660 may be distributed among multiple interface devices. Storage system 640 may comprise a disk, tape, integrated circuit, RAM, ROM, network storage, server, or other memory function. Storage system 640 may be a computer readable medium. Storage system 640 may be distributed among multiple memory devices.

Processing system 630 retrieves and executes software 650 from storage system 640. Processing system may retrieve and store data 670. Processing system may also retrieve and store data via communication interface 620. Processing system 650 may create or modify software 650 or data 670 to achieve a tangible result. Processing system 630 may control communication interface 620 or user interface 670 to achieve a tangible result. Processing system 630 may retrieve and execute remotely stored software via communication interface 620.

Software 650 and remotely stored software may comprise an operating system, utilities, drivers, networking software, and other software typically executed by a computer system. Software 650 may comprise an application program, applet, firmware, or other form of machine-readable processing instructions typically executed by a computer system. When executed by processing system 630, software 650 or remotely stored software may direct computer system 600 to operate as described herein.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A personal vaporizing unit system, comprising:
    a case having a cradle;
    a computer running an application to communicate data; and,
    a personal vaporizing unit that communicates said data with the computer, the personal vaporizing unit comprising:
        a microprocessor for recording performance data about said personal vaporizing unit that is provided to the computer and for receiving settings data about the personal vaporizing unit from the computer, wherein the settings data includes battery settings and settings modifying a flavor of a vapor product;
        a memory for storing said performance data and said settings data; and,
        a first contact and a second contact, said first contact and said second contact to form an electrical contact with said cradle adapted to hold the personal vaporizing unit when the personal vaporizing unit is held by said cradle, said first contact and said second contact conducting charge from said case to said personal vaporizing unit to charge said personal vaporizing unit, the case having a wireless interface to transfer said performance data and settings data between said application and said personal vaporizing unit.

2. The personal vaporizing system unit of claim 1, wherein said wireless interface comprises at least one of an 802.15 specified interface, an 802.11 specified interface, or a cellular telephone network.

3. The personal vaporizing unit system of claim 1, wherein said application configures at least one setting of said personal vaporizing unit using said data.

4. The personal vaporizing unit system of claim 1, wherein said application unlocks the personal vaporizing unit using said data.

5. The personal vaporizing unit system of claim 4, wherein said application receives a personal identification number or biometric information from a user to unlock the personal vaporizing unit.

6. The personal vaporizing unit system of claim 1 wherein said settings comprise updates for software on said personal vaporizing unit.

7. A personal vaporizing system comprising:
- a personal digital device;
- a personal vaporizing unit that communicates with the personal digital device, the personal vaporizing unit comprising:
  - a porous wick element;
  - a cartridge providing liquid to the porous wick element;
  - a heating element that vaporizes the provided liquid from the porous wick element, wherein the porous wick element transports the liquid from the cartridge to the heating element;
  - a processor for monitoring performance data and for receiving settings data about the personal vaporizing unit from the personal digital device, wherein the settings data includes battery settings and settings modifying a flavor of a vapor product;
  - a memory for storing the performance data and the settings data;
  - a network interface for communicating with the personal digital device or a network;
- wherein the personal digital device provides updates to the personal vaporizing unit that include the settings data and receives the performance data from the personal vaporizing unit.

8. The personal vaporizing system of claim 7 wherein the personal digital device comprises an application that communicates the updates and performance data with the personal vaporizing unit.

9. The personal vaporizing system of claim 8 wherein the application is an interface that displays the performance data.

10. The personal vaporizing system of claim 9 wherein the personal digital device comprises a smartphone with an application that provides the interface.

11. The personal vaporizing system of claim 7 further comprising:
- a case that receives and charges the personal vaporizing unit.

12. The personal vaporizing system of claim 11 wherein the case communicates with the personal digital device.

* * * * *